United States Patent
Everson et al.

(10) Patent No.: US 12,332,255 B2
(45) Date of Patent: *Jun. 17, 2025

(54) METHODS FOR MONITORING TREATMENT OF CHRONIC LIVER DISEASE

(71) Applicant: The Regents of the University of Colorado, Denver, CO (US)

(72) Inventors: Gregory Thomas Everson, Englewood, CO (US); Steve Mark Helmke, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/504,788

(22) Filed: Oct. 19, 2021

(65) Prior Publication Data
US 2022/0034915 A1    Feb. 3, 2022

Related U.S. Application Data

(60) Division of application No. 16/460,767, filed on Jul. 2, 2019, now Pat. No. 11,181,536, which is a
(Continued)

(51) Int. Cl.
*G01N 33/92* (2006.01)
*A61K 31/575* (2006.01)
(Continued)

(52) U.S. Cl.
CPC ........... *G01N 33/92* (2013.01); *A61K 31/575* (2013.01); *G16H 50/20* (2018.01); *G16H 50/30* (2018.01); *G01N 2800/085* (2013.01)

(58) Field of Classification Search
CPC .. G01N 33/92; G01N 2800/085; G16H 50/30; G16H 50/20; A61K 31/575
See application file for complete search history.

(56) References Cited

U.S. PATENT DOCUMENTS

| 4,207,308 A | 6/1980 | Spenney |
| 6,778,269 B2 | 8/2004 | Fink et al. |

(Continued)

FOREIGN PATENT DOCUMENTS

| AU | 2012262329 | 10/2014 |
| EP | 1150123 | 10/2001 |

(Continued)

OTHER PUBLICATIONS

Zimmermann et al., PLoS One, 2011, 6(6) e21381, pp. 1-10.*
(Continued)

*Primary Examiner* — Sean C. Barron
(74) *Attorney, Agent, or Firm* — Merchant & Gould, P.C.

(57) ABSTRACT

A Disease Severity Index (DSI) is provided for assessment of chronic liver disease in a patient using non-invasive liver function test results. A DSI was derived from non-invasive liver function test results based on hepatic blood flow. The DSI is used in methods for prediction of clinical outcomes, prediction of response to antiviral treatment, and assessment of progression of chronic liver diseases. Non-invasive methods to diagnose three distinct categories of patients with Primary Sclerosing Cholangitis (PSC) are provided. The methods can be used to diagnose PSC patients as Slow Progressors, Moderate Progressors and Rapid Progressors.

26 Claims, 18 Drawing Sheets

Related U.S. Application Data continuation of application No. 15/673,191, filed on Aug. 9, 2017, now Pat. No. 10,520,517, which is a continuation of application No. 14/729,987, filed on Jun. 3, 2015, now Pat. No. 9,759,731, which is a continuation of application No. 14/078,058, filed on Nov. 12, 2013, now Pat. No. 9,091,701.

(60) Provisional application No. 61/725,292, filed on Nov. 12, 2012.

(51) Int. Cl.
  *G16H 50/20* (2018.01)
  *G16H 50/30* (2018.01)

(56) References Cited

U.S. PATENT DOCUMENTS

| | | |
|---|---|---|
| 7,060,250 B2 | 6/2006 | McMurry et al. |
| 8,613,904 B2 | 12/2013 | Everson et al. |
| 8,778,299 B2 | 7/2014 | Everson |
| 8,961,925 B2 | 2/2015 | Everson et al. |
| 9,091,701 B2 | 7/2015 | Everson et al. |
| 9,417,230 B2 | 8/2016 | Everson |
| 9,759,731 B2 | 9/2017 | Everson et al. |
| 10,520,517 B2 | 12/2019 | Everson et al. |
| 11,181,536 B2 | 11/2021 | Everson et al. |
| 2006/0067881 A1 | 3/2006 | Groman et al. |
| 2006/0251576 A1 | 11/2006 | Hellerstein |
| 2008/0279766 A1 | 11/2008 | Everson et al. |
| 2010/0055734 A1 | 3/2010 | Everson |
| 2012/0329161 A1 | 12/2012 | Everson et al. |
| 2014/0067276 A1 | 3/2014 | Everson et al. |
| 2014/0147875 A1 | 5/2014 | Everson et al. |
| 2014/0326926 A1 | 11/2014 | Everson et al. |
| 2015/0204842 A1 | 7/2015 | Everson et al. |
| 2015/0268255 A1 | 9/2015 | Everson et al. |
| 2016/0305930 A1 | 10/2016 | Everson et al. |

FOREIGN PATENT DOCUMENTS

| | | |
|---|---|---|
| JP | 2003532899 | 11/2003 |
| JP | 2004507740 | 3/2004 |
| JP | 2010502979 | 1/2010 |
| WO | 2/16949 | 2/2002 |
| WO | 2008/029145 | 3/2008 |
| WO | 2012/166802 | 12/2012 |
| WO | 2014/075082 | 5/2014 |

OTHER PUBLICATIONS

I.R. Mackay. Chronic Hepatitis: Effect of Prolonged Suppressive Treatment and Comparison of Azathioprine With Prednisolone. Q J Med, 1968, 37(147):379-392. (Year: 1968).*
Wallack et al. Non-Invasive Measurement of the Portal Circulation Using Cholates Quantifies Disease Severity in Primary Sclerosing Cholangitis Gas. 2012, 142: S911. (Year: 2012).*
Zimmermann et al. Interleukin-8 Is Activated in Patients with Chronic Liver Diseases and Associated with Hepatic Macrophage Accumulation in Human Liver Fibrosis. PLoS One, 2011, 6(6) e21381, pp. 1-10. (Year: 2011).*
Afdhal et al., "Advances in Hepatology—Fibroscan (Transient Elastography) for the Measurement of Liver Fibrosis"; Sec. Ed. Schiff, Gastroenterology & Hepatology; 8(9):605-607 (Sep. 2012).
Bio Predictive, "Technical Recommendations for FibroTest and FibroMax assays"; A Guide for biologists and laboratories, V. 1.17, 28 pgs (Oct. 20, 2014).
Chronic Hepatitis Data Sheet, Merck, Sharp & Dohme, Corp., 1 page (2010-2011).
Dax et al., "HPLC-Continuous-Flow Fast Atom Bombardment Mass Spectrometry (HPLC-CFFAB)—a Convenient Method for the Analysis of Bile Acids in Bile and Serum"; Chromatographia, 40(11/12):674-679 (Jun. 1995).
Decompensated Cirrhosis Data Sheet, U.S. Department of Veterans Affairs, 1 page (2011).
DeMark, "A method for the accurate measurement of isotope ratios of chenodeoxycholic and cholic acids in serum"; J Lipid Res, 23:204-210 (1982).
Denaro et al., "The effect of liver disease on urine caffeine metabolite ratios"; Clinical Pharmacology and Therapeutics, 59:624-635 (1996).
Di Bisceglie, "Prolonged therapy of advanced chronic hepatitis C with low-dose peginterferon"; N Engl J Med, 359 (23):2429-2441 (Dec. 4, 2008).
Eichelbaum, "Simultaneous Determination of the intravenous and Oral Pharmacokinetic Parameters of D,L-Verapamil Using Stable Isotope-Labelled Verapamil"; Eur J Clin Pharmacol, 19:133-137 (1981).
European Search Report for Application No. 10815965.8 mailed Apr. 17, 2013.
Everson et al., "Quantitative Tests (QLFTS) Detect Impaired Hepatic Function in a High Proportion of Chronic Hepatitis C Patients With Fibrosis or Compensated Cirrhosis and may Predict Risk of Cirrhosis, Splenomegaly, and Varices"; Hepatology, 38:304-305 (2003).
Everson et al., "Qualitative Tests (QLFTS) Detect Impaired Hepatic Function in a High Proportion of Patients with Chronic HCV and Firbrosis or Cirrhosis and May Predict Risk of Cirrhosis, Splenomegaly and Varices", presentation at the 54th Annual Meeting of the American Association for the Stady of Liver Diseases, (Oct. 2003).
Everson et al., "Portal-systemic shunting in patients with fibrosis or cirrhosis due to chronic hepatitis C: the minimal model for measuring cholate clearances and shunt", Alimentary Pharmacology & Therapeutics, 26:401-410 (2007).
Everson et al., "The spectrum of hepatic functional impairment in compensated chronic hepatitis C: results from the Hepatitis C Anti-viral Long-term Treatment against Cirrhosis Trial"; Alimentary Pharmacology & Therapeutics, 27:798-809 (2008).
Everson et al., "Hepatic Impairment Measured by Quantitative Tests of Liver Function (QLFTs) Predicts Clinical Outcome in Patients with Advanced Fibrosis: Results from the Hepatitis C Anti-viral Long-term Treatment against Cirrhosis (HALT-C) trial"; Hepatology 50(4 Suppl.):1057A, Abstract 1627 (2009).
Everson et al. "Quantitative tests of liver function measure hepatic improvement after sustained virological response: results from the HALT-C trial"; Alimentary Pharmacology & Therapeutics, 29:589-601(2009).
Everson et al., "Quantitative Liver Function Tests Improve the Prediction of Clinical Outcomes in Chronic Hepatitis C: Results from the Hepatitis C Antiviral Long-term Treatment Against Cirrhosis Trial"; Hepatology, 55(4):1019-1029 (Apr. 2012).
Everson et al., "Functional Elements Associated with Hepatic Regeneration in Living Donors After Right Hepatic Lobectomy," Liver Transplantation, vol. 19, No. pp. 292-304 (2013).
Exalenz Breathid® breath test device for the diagnosis of liver disease; Health Policy Advisory Committee on Technology—Technology Brief (Aug. 2012).
Examination Report for Australian Application No. 2013341378, mailed Jan. 17, 2017, 3 pages total.
Examination Report No. 1 from related Australian patent application 2012262329, mailed Jun. 23, 2014.
Extended European Search Report for EP 06734026.5, mailed Mar. 31, 2011.
Gilmore et al., "Plasma clearance of oral and intravenous cholic acid in subjects with and without chronic liver disease"; Gut, 21:123-127 (1980).
Golden et al., "Application of an enzyme-multiplied immunoassay technique for determination of caffeine elimination kinetics as a test of liver function in clinically normal dogs"; American Journal of Veterinary Research, 55(6):790-794 (Jun. 1994).
Guidance for Industry, Bioanalytical Method Validation, (May 2001).
Haque et al., "Hepatitis C antiviral long-term treatment against cirrhosis (HALT-C) trial"; Annals of Hepatology, 8 (1):78-79 (Jan.-Mar. 2009).

(56) References Cited

OTHER PUBLICATIONS

HCV Fibrosure™, Informational Sheet; Laboratory Corporation of America (2004).
Hechey et al., "Syntheses with stable isotopes: synthesis of deuterium and 13C labeled bile acids," Journal of Labelled Compounds, IX(4):703-719 (Oct.-Dec. 1973).
Helmke et al., "Slow, Moderate, and Rapid Progressors: Three Distinct Categories of Patients with Primary Sclerosing Cholangitis Detected by Functional Assessment using Cholate Testing," Hepatology, 56(4)(Suppl):1133A, Abstract No. 2027 (Oct. 2012).
Helmke et al., "Noninvasive assessment of liver function"; Liver—Current Opinion in Gastroenterology 31(3):1-10 (Feb. 31, 2015).
Herold et al., "Quantitative testing of liver function in patients with cirrhosis due to chronic hepatitis C to assess disease severity"; Liver, 21:26-30 (2001).
Hoofnagle, "Course and outcome of hepatitis C"; Hepatology, 36(5):S21 (Nov. 2002).
Hydzik et al., "Usefulness of 13C-methacetin breath test in liver function testing in Amanita phalloides poisoning: breast feeding woman case"; Clinical Toxicology, 46:1077-1082 (2008).
International Search Report for PCT/US06/03132, mailed Jul. 11, 2007.
International Search Report and Written Opinion for PCT/US10/47976, mailed Feb. 2, 2011.
International Search Report and Written Opinion cited in PCT/US2012/040008 mailed Sep. 6, 2012.
International Search Report and Written Opinion for PCT/US13/69708 mailed Feb. 10, 2014.
Invitation to Pay Additional Fees for PCT/US10/47676, dated Nov. 17, 2010.
Japanese Office Action mailed Aug. 28, 2017 in Japanese patent application No. 2015-542017 and English language translation, 8 pages total.
Kamath et al., "A Model to Predict Survival in Patients with End-Stage Liver Disease"; Hepatology, 33(2):464-470 (Feb. 2001).
Kern, "Normal Plasma Cholesterol in an 88-year-old Man Who Eats 25 Eggs a Day"; New England J Medicine, 324:896-899 (1991).
Koster et al., "Recent Developments in On-line SPE for HPLC and LC-MS in Bioanalysis"; Guide to LC-MS, 3 pp. (Dec. 2001).
Krumbiegel et al., "[15N]methacetin urine test: a method to study the development of hepatic detoxification capacity"; Eur J Pediatr., 149(6):393-395 (Mar. 1990).
Lalazar et al., "A continuous 13C methacetin breath test for noninvasive assessment of intrahepatic inflammation and fibrosis in patients with chronic HCV infection and normal ALT"; Journal of Viral Hepatitis 15(10):716-28 (Oct. 2008).
Mackay, Q J Med., 1968, 37(147):379-392.
Martucci, "Deconvolutional Analysis on Clearance Curves of Simultaneously Administered Oral and Intravenous Doses of 2,2,4,4-2H Cholate and 24-13C Cholate: Minimal Model to Determine First-Pass Hepatic Extraction of Cholate in Humans"; Research paper, University of Colorado Health Sciences Center (Aug. 2004).
Medrzejewski et al., "Plasma Clearance of Cholic Acid in Patients With Chronic Diseases of the Liver"; Polski Tygodnik Lekarski, 45(16-18):335-337, Abstract Only, 1 page. (Apr. 16-30, 1990).
Miescher et al., "Portal-systemic spill-over of bile acids: a study of mechanisms using ursodeoxycholic acid"; European J of Clinical Investigation; 13:439-445 (1983).
Nguyen et al., "Diagnostic and Therapeutic Advances in Hepatology-Noninvasive Assessment of Liver Fibrosis"; Hepatology; 2107-2110 (Jun. 2011).
Office Action for EP 12731209.8 dated Sep. 7, 2016, 4 pages total.
Queiroz et al., "Practical Tips on Preparing Plasma Samples for Drug Analysis Using SPME," LCGC North America, vol. 22, No. 10, 6 pages (Oct. 2004).
Ratziu et al., "Diagnostic value of biochemical markers (Fibro Test-FibroSURE) for the prediction of liver fibrosis in patients with non-alcoholic fatty liver disease"; BMC Gastroenterology; 6:6 (Feb. 14, 2006).
Rector et al., Renal sodium retention complicating alcoholic liver disease: Relation to portosystemic shunting and liver function Hepatology 12(3):455-459 (1990).
Renner et al., "Caffeine: A Model Compound for Measuring Liver Function", Hepatology 4(1):38-46 (1984).
Shah et al., "Comparison of Noninvasive Markers of Fibrosis in Patients With Nonalcoholic Fatty Liver Disease"; Clinical Gastroenterology and Hepatology; 7(10):1104-1112 (2009).
Shrestha et al., "Quantitative liver function tests define the functional severity of liver disease in early-state cirrhosis"; Liver Transplantation and Surgery 3(2):166-167, 172 (Mar. 1997).
Stellaard, et al., "Measurement of Bile Acid Kinetics in Human Serum Using Stable Isotope Labeled Chenodeoxycholic Acid and Capillary Gas Chromatograpy Electron Impact Mass Spectrometry," Biomedical Mass Spectrometry, 10 (3):187-191 (1983).
Stellaard, et al., "Simultaneous determination of cholic acid and chenodeoxycholic acid pool size and fractional turnover rates in human serum using 13C-labeled bile acids"; Journal of Lipid Research, 25:1313-1319 (1984).
Stellaard, "Simultaneous determination of pool sizes and fractional turnover rates, of deoxycholic acid, cholic acid and chenodeoxycholic acid in man by isotope dilution with 2H and 13C labels and serum sampling," Biomedical and Environmental Mass Spectrometry, vol. 14, pp. 609-611 (1987).
Supplementary European Search Report for Application No. 13853943.2 mailed May 23, 2016, 8 pages total.
Toyoda et al., Clin Gas and Hepatology, 2006, 4:1528-1536.
Wallack et al., "Non-invasive measurement of the portal circulation using cholates quantifies disease severity in primary sclerosing cholangitis", Gastroenterology, vol. 142, No. 5, suppl. 1, p. S911 (May 1, 2012).

* cited by examiner

METHODS FOR MONITORING TREATMENT OF CHRONIC LIVER DISEASE

CROSS-REFERENCES TO RELATED APPLICATIONS

This application is a Divisional of U.S. patent application Ser. No. 16/460,767, filed Jul. 2, 2019, now U.S. Pat. No. 11,181,536; which is a Continuation of U.S. patent application Ser. No. 15/673,191, filed Aug. 9, 2017, now U.S. Pat. No. 10,520,517; which is a Continuation of U.S. patent application Ser. No. 14/729,987, filed Jun. 3, 2015, now U.S. Pat. No. 9,759,731; which is a Continuation of U.S. patent application Ser. No. 14/078,058, filed Nov. 12, 2013, now U.S. Pat. No. 9,091,701, issued Jul. 28, 2015; which claims the benefit of U.S. Provisional Application No. 61/725,292, filed Nov. 12, 2012, the entire contents of each of which are incorporated herein by reference.

STATEMENT REGARDING FEDERALLY SPONSORED RESEARCH OR DEVELOPMENT

This invention was made with government support under Contract No. DK092327 awarded by the National Institutes of Health. The government has certain rights in the invention.

BACKGROUND OF THE INVENTION

Field of the Invention

A Disease Severity Index (DSI) useful in assessment of chronic liver disease in a patient is derived from one or more liver function test results based on hepatic blood flow. The DSI is used in methods for patient assessment in a number of chronic liver diseases. Non-invasive methods to diagnose three distinct categories of patients with Primary Sclerosing Cholangitis (PSC) are also provided. The methods can be used to diagnose PSC patients as Slow Progressors, Moderate Progressors and Rapid Progressors.

Description of the Related Art

Until now, fibrosis stage on liver biopsy was considered the gold standard as the surrogate for clinical outcomes in patients with chronic liver disease. Several studies have demonstrated that severity of fibrosis, but not steatosis, predicts future risk for clinical outcome. Unfortunately the accuracy of biopsy in staging of fibrosis is compromised by both sampling error and variation in histopathologic interpretation. In addition, biopsy is invasive, costly, not embraced by patients, and associated with significant risks, including risk of life-threatening complication or even death. Alternatives to liver biopsy are desirable.

Chronic liver disease. Estimates suggest that 30 million or more Americans may be affected by chronic liver disease. Chronic liver diseases (CLDs) include chronic hepatitis C (CHC), chronic hepatitis B, alcoholic liver disease, Alcoholic SteatoHepatitis (ASH), and Non-Alcoholic Fatty Liver Disease (NAFLD) which can progress from simple fatty liver called steatosis, which is relatively benign, to the more serious Non-Alcoholic SteatoHepatitis (NASH), autoimmune liver disease, cryptogenic cirrhosis, hemochromatosis, Wilson's disease, alpha-1-antitrypsin deficiency, primary sclerosing cholangitis (PSC) and other cholestatic liver diseases.

All liver diseases have common pathophysiologic characteristics with disease progression fueled by inflammation, accumulation of fibrosis, and alteration of the portal circulation. Tests involving non-invasive assessment of portal blood flow are desirable for patients having, or suspected of having, any chronic liver disease.

Primary Sclerosing Cholangitis. Primary sclerosing cholangitis (PSC) is a progressive liver disease that leads to liver damage and ultimately to liver failure. PSC exhibits inexorable progression but the rate of progression varies between patients. Chronic inflammation leads to hardening and scarring of the bile ducts. Liver transplant is the only known cure for PSC, but transplant is typically reserved for patients with severe liver damage. Patient care involves reducing signs and symptoms of complications of PSC. The hallmark of PSC pathophysiology is portal fibrosis leading to portal hypertension (PHTN) earlier in disease compared to other etiologies of liver disease.

Assessment of disease severity in PSC lacks a gold standard, as liver biopsy has significant sampling error and is no longer recommended. Hepatic Venous Pressure Gradient (HVPG) is invasive, expensive and impractical, and clinical models were really created to assess late-stage disease. Previously disclosed liver function tests SHUNT, Portal HFR and STAT were performed in PSC patients as disclosed in Everson et al., U.S. Ser. No. 13/484,083, filed May 30, 2012, which is incorporated herein by reference. Although these tests could delineate disease severity, there is still an unmet need for accurate non-invasive methods for diagnosing rate of progression of PSC.

Two known liver function tests, the Portal HFR (Portal hepatic filtration rate, FLOW) test and the SHUNT test, have been used to accurately measure portal blood flow and were previously validated using a large cohort of patients with chronic hepatitis C. The portal HFR and SHUNT tests for liver function in patients with chronic hepatitis C were disclosed in prior applications by the present inventors.

The portal HFR (FLOW) test, accurately measures the portal blood flow from a minimum of 5 blood samples taken over a period of 90 minutes after an oral dose of deuterated-cholate. The portal HFR (FLOW) test is disclosed in Everson, US 2010/0055734, Methods for Diagnosis and Intervention of Hepatic Disorders, filed Sep. 11, 2009, which is incorporated herein by reference.

The SHUNT test, comprises simultaneous administration of an intravenous dose of $^{13}$C-cholate and an oral dose of deuterated-cholate. The SHUNT test can be used to measure portal blood flow, and systemic hepatic blood flow and therefore determine the amount of portal-systemic shunting. The SHUNT test is disclosed in Everson et al., US2008/0279766, Methods for Diagnosis and Intervention of Hepatic Disorders, filed Jan. 26, 2006, which is incorporated herein by reference. A test for estimating portal blood flow is also applicable to other chronic liver diseases.

A third test called the STAT test is a screening method for estimating portal blood flow and hepatic function. The STAT test is disclosed in Everson et al., U.S. Ser. No. 13/484,083, filed May 30, 2012, which is incorporated herein by reference. The STAT test is intended for screening purposes and is used in conjunction with FLOW and SHUNT tests to monitor hepatic blood flow and hepatic function. For example, a patient with a STAT screening test result above a cut-off level is subjected to the more comprehensive portal HFR and SHUNT tests to monitor hepatic blood flow and hepatic function in the patient.

The portal HFR (FLOW), SHUNT and STAT tests are currently used for defining disease severity in patients with chronic hepatitis C and other chronic liver diseases. A variety of cut-offs have been established for use in tracking disease progression of specific diseases and assessment of response to treatments. However, no general index of severity with utility for any chronic liver disease has yet been developed.

The portal HFR and SHUNT tests are valuable tools for assessment of liver function for a number of clinical applications, for example, selection of patients with chronic hepatitis B who should receive antiviral therapy; selection of patients with chronic hepatitis C who should receive antiviral therapy; assessing the risk of hepatic decompensation in patients with hepatocellular carcinoma (HCC) being evaluated for hepatic resection; identifying a subgroup of patients on waiting list with low MELD (Model for End-stage Liver Disease score) who are at-risk for dying while waiting for an organ donor; as an endpoint in clinical trials; replacing liver biopsy in pediatric populations; tracking of allograft function; measuring return of function in living donors; and measuring functional impairment in cholestatic liver disease (PSC, Primary Sclerosing Cholangitis). Although various cut-offs for the FLOW and SHUNT tests have been developed for specific conditions, development of a Disease Severity Index (DSI) applicable to several clinical conditions in liver disease is clearly desirable.

SUMMARY OF THE INVENTION

In some embodiments, a Disease Severity Index (DSI) is provided for use in methods for monitoring chronic liver disease in a patient. The DSI is derived from liver function test results based on hepatic blood flow. The DSI is used in methods for monitoring treatment and assessment of disease severity in a number of chronic liver diseases.

In some embodiments, a method is provided for determining a disease severity index (DSI) value in a patient, the method comprising (a) obtaining one or more liver function test values in a patient having or at risk of a chronic liver disease, wherein the one or more liver function test values are obtained from one or more liver function tests selected from the group consisting of SHUNT, portal hepatic filtration rate (portal HFR), and systemic hepatic filtration rate (systemic HFR); and (b) employing a disease severity index equation (DSI equation) to obtain a DSI value in the patient, wherein the DSI equation comprises one or more terms and a constant to obtain the DSI value, wherein at least one term of the DSI equation independently represents a liver function test value in the patient, or a mathematically transformed liver function test value in the patient from step; and the at least one term of the DSI equation is multiplied by a coefficient specific to the liver function test.

In some embodiments, the method for determining a disease severity index (DSI) value in a patient further comprises comparing the DSI value in the patient to one or more DSI cut-off values, one or more normal healthy controls, or one or more DSI values within the patient over time. In some embodiments, the comparing the DSI value in the patient to one or more DSI cut-off values is indicative of at least one clinical outcome. In some embodiments, the clinical outcome is selected from the group consisting of Child-Turcotte-Pugh (CTP) increase, varices, encephalopathy, ascites, and liver related death.

In some embodiments, comparing the DSI value within the patient over time is used to monitor the effectiveness of a treatment of chronic liver disease in the patient, wherein a decrease in the DSI value in the patient over time is indicative of treatment effectiveness.

In some embodiments, comparing the DSI value in the patient over time is used to monitor the need for treatment of chronic liver disease in the patient, wherein an increase in the DSI value in the patient over time is indicative of a need for treatment in the patient.

In some embodiments, the DSI value in the patient is used to monitor the need for, or the effectiveness of, a treatment of chronic liver disease in the patient wherein the treatment is selected from the group consisting of antiviral treatment, antifibrotic treatment, antibiotics, immunosuppressive treatments, anti-cancer treatments, ursodeoxycholic acid, insulin sensitizing agents, interventional treatment, liver transplant, lifestyle changes, and dietary restrictions, low glycemic index diet, antioxidants, vitamin supplements, transjugular intrahepatic portosystemic shunt (TIPS), catheter-directed thrombolysis, balloon dilation and stent placement, balloon-dilation and drainage, weight loss, exercise, and avoidance of alcohol.

In some embodiments, comparing the DSI value within the patient over time is used to monitor status or disease progression of a chronic liver disease in the patient, wherein change in DSI value within the patient over time is used to inform the patient of status of the disease and risk for future clinical outcomes, wherein an increase in the DSI value within the patient over time is indicative of a worse prognosis, and a decrease in the DSI value within the patient over time is indicative of a better prognosis.

In some embodiments, at least one term of the DSI equation independently represents a mathematically transformed liver function test value in the patient from step wherein the mathematically transformed liver function test value in the patient is selected from a log, antilog, natural log, natural antilog, or inverse of the liver function test value in the patient.

In some embodiments, each term of the DSI equation independently represents a liver function test value in the patient, or a mathematically transformed liver function test value in the patient, and the at least one term of the DSI equation is multiplied by a coefficient specific to the liver function test.

In some embodiments, the disease severity index equation is $$DSI = 5.34\,(SHUNT) - 6.65\,(Log_e\,Portal\,HFR) - 8.57\,(Log_e\,Systemic\,HFR) + 44.66$$

where SHUNT is SHUNT test value in the patient (%), portal HFR is portal HFR test value in the patient as mL/min/kg, wherein kg is body weight of the patient, and systemic HFR is systemic HFR value in the patient as mL/min/kg, wherein kg is body weight of the patient, wherein the SHUNT, the portal HFR, and the systemic HFR test values in the patient were obtained on the same day.

In some embodiments, the disease severity index equation is $$DSI = 5.75\,(SHUNT) - 7.22\,(Log_e\,Portal\,HFR) - 8.45\,(Log_e\,Systemic\,HFR) + 50$$

where SHUNT is SHUNT test value in the patient (%), portal HFR is portal HFR test value in the patient as mL/min/kg, wherein kg is body weight of the patient, and systemic HFR is systemic HFR value in the patient as mL/min/kg, wherein kg is body weight of the patient, wherein the SHUNT, the portal HFR, and the systemic HFR test values in the patient were obtained on the same day.

In some embodiments, the DSI value in the patient is used to assess chronic liver disease in the patient selected from chronic hepatitis C, non-alcoholic fatty liver disease or primary sclerosing cholangitis.

In some embodiments, the disease severity index equation used to assess chronic liver disease in the patient is $$DSI=9.84 \text{ (SHUNT)}-12.36 \text{ LOG}e \text{ (portal HFR)}+50.5$$

where SHUNT is SHUNT test value in the patient (%) and portal HFR is portal HFR test value in the patient as mL/min/kg, wherein kg is body weight of the patient, wherein the SHUNT and the portal HFR test values in the patient were obtained on the same day. In some embodiments, the chronic liver disease is chronic hepatitis C.

In some embodiments, a SHUNT test value in the patient is used in the DSI equation, and the SHUNT test value is determined by a method comprising receiving a plurality of blood or serum samples collected from the patient having PSC, following oral administration of a dose of a first distinguishable cholate (dose$_{oral}$) to the patient and simultaneous intravenous co-administration of a dose of a second distinguishable cholate (dose$_{iv}$) to the patient, wherein the samples have been collected over intervals spanning a period of time after administration; quantifying the concentration of the first and the second distinguishable cholates in each sample; generating an individualized oral clearance curve from the concentration of the first distinguishable cholate in each sample comprising using a computer algorithm curve fitting to a model oral distinguishable cholate clearance curve and computing the area under the individualized oral clearance curve (AUCoral); generating an individualized intravenous clearance curve from the concentration of the second distinguishable cholate in each sample by use of a computer algorithm curve fitting to a model intravenous second distinguishable cholate clearance curve and computing the area under the individualized intravenous clearance curve (AUCiv); and calculating the shunt value in the patient using the formula:

$$AUC_{oral}/AUC_{iv} \times Dose_{iv}/Dose_{oral} \times 100\%.$$

In some embodiments, the SHUNT test employs a first distinguishable cholate is a first stable isotope labeled cholic acid and a second distinguishable cholate is a second stable isotope labeled cholic acid. In some embodiments, the first and second stable isotope labeled cholic acids are selected from 2,2,4,4-d4 cholate and 24-$^{13}$C-cholate. In some embodiments, the samples have been collected from the patient over intervals of from two to seven time points after administration. In some embodiments, the samples have been collected from the patient at 5, 20, 45, 60 and 90 minutes after administration. In some embodiments, the samples have been collected over intervals spanning a period of time from the time of administration to a time selected from about 45 minutes to about 180 minutes after administration. In some embodiments, the samples have been collected over intervals spanning a period of time of about 90 minutes or less after administration.

In some embodiments, a portal HFR value in the patient is used in the DSI equation, and the portal HFR value is determined by a method comprising the steps of receiving a plurality of blood or serum samples collected from a patient having or at risk of a chronic liver disease, following oral administration of a dose of a distinguishable cholate (dose$_{oral}$) to the patient, wherein the samples have been collected from the patient over intervals spanning a period of time after administration; measuring concentration of the distinguishable cholate in each sample; generating an individualized oral clearance curve from the concentration of the distinguishable cholate in each sample comprising using a computer algorithm curve fitting to a model distinguishable cholate clearance curve; computing the area under the individualized oral clearance curve (AUC)(mg/mL/min) and dividing the dose (in mg) by AUC of the orally administered stable isotope labeled cholic acid to obtain the oral cholate clearance in the patient; and dividing the oral cholate clearance by the weight of the patient in kg to obtain the portal HFR value in the patient (mL/min/kg).

In some embodiments, a systemic HFR value in the patient is used in the DSI equation and the systemic HFR value in the patient is determined by a method comprising the steps of receiving a plurality of blood or serum samples collected from a patient having or at risk of a chronic liver disease, following intravenous administration of a dose of a distinguishable cholate (closely) to the patient, wherein the samples have been collected from the patient over intervals spanning a period of time after administration; measuring concentration of the distinguishable cholate in each sample; generating an individualized intravenous clearance curve from the concentration of the distinguishable cholate in each sample comprising using a computer algorithm curve fitting to a model distinguishable cholate clearance curve; computing the area under the individualized intravenous clearance curve (AUC)(mg/mL/min) and dividing the dose (in mg) by AUC of the intravenously administered stable isotope labeled cholic acid to obtain the intravenous cholate clearance in the patient; and dividing the intravenous cholate clearance by the weight of the patient in kg to obtain the systemic HFR value in the patient (mL/min/kg).

In some embodiments, a method is provided for calculating a disease severity index (DSI) value for a patient suffering from a chronic liver disease, the method comprising obtaining serum samples from a patient suffering from a chronic liver disease, wherein the patient previously received oral administration of a first stable isotope cholate and simultaneously intravenous administration of a second stable isotope cholate, and wherein blood samples had been collected from the patient over an interval of less than 180 minutes following administration of the cholates; assaying the serum samples to calculate the portal hepatic filtration rate (portal HFR) as mL/min/kg, wherein kg is body weight of the patient, the systemic hepatic filtration rate (systemic HFR) as mL/min/kg wherein kg is body weight of the patient, and SHUNT as %; and calculating a DSI value for the patient by using an equation selected from:

$$DSI=9.84 \text{ (SHUNT)}-12.36 \text{ Log}_e \text{ (portal HFR)}+50.5;$$

$$DSI=5.75 \text{ (SHUNT)}-7.22 \text{ (Log}_e \text{ Portal HFR)}-8.45 \text{ (Log}_e \text{ Systemic HFR)}+50; \text{ or}$$

$$DSI=5.34 \text{ (SHUNT)}-6.65 \text{ (Log}_e \text{ Portal HFR)}-8.57 \text{ (Log}_e \text{ Systemic HFR)}+44.66.$$

In some embodiments, the DSI equation is $$DSI=5.75 \text{ (SHUNT)}-7.22 \text{ (Log}_e \text{ Portal HFR)}-8.45 \text{ (Log}_e \text{ Systemic HFR)}+50, \text{ and the}$$

DSI value is used for identifying increased risk for portal hypertension or decompensation in the chronic liver disease patient wherein a DSI≥18 indicates increased risk for portal hypertension (PHTN), and a DSI≥36 indicates an increased risk for decompensation. In some embodiments, the portal hypertension (PHTN) is defined as splemomegaly or varices, and decompensation is defined as ascites or variceal hemorrhage. In some embodiments, the chronic liver disease is primary sclerosing cholangitis.

In some embodiments, the DSI equation used for calculating a disease severity index (DSI) value for a patient suffering from a chronic liver disease is $$DSI=5.75 \text{ (SHUNT)}-7.22 \text{ (Log}_e \text{ Portal HFR)}-8.45 \text{ (Log}_e \text{ Systemic HFR)}+50,$$

and the DSI value is used for prediction of clinical outcomes in the chronic liver disease patient, wherein a DSI≥25 indicates an increased risk of clinical outcome in the patient. In some embodiments, the chronic liver disease is chronic hepatitis C. In some embodiments, the clinical outcome is selected from CTP progression, variceal hemorrhage, ascites, hepatic encephalopathy, or liver-related death.

In some embodiments, the patient is on the waiting list for liver transplant (LT), and the DSI equation is $$DSI=5.75 \text{ (SHUNT)}-7.22 \text{ (Log}_e \text{ Portal HFR)}-8.45 \text{ (Log}_e \text{ Systemic HFR)}+50,$$

wherein the DSI value is used for prioritizing the patient on the waiting list for LT, wherein the priority of the patient on the waiting list for LT is increased following an increase in the DSI value over time in the patient, or following a DSI value in the patient of greater than 40.

In some embodiments, the DSI equation is DSI=5.34 (SHUNT)−6.65 (Loge Portal HFR)−8.57 (Loge Systemic HFR)+44.66, and the DSI value is used for prediction of future clinical outcomes in a chronic liver disease patient, wherein a DSI>19 indicates an increased risk of clinical outcomes in the patient.

In some embodiments, a DSI equation is provided comprising two or more terms and a constant to obtain the DSI value, wherein at least one term of the DSI equation independently represents a liver function test value in the patient, or a mathematically transformed liver function test value in the patient from step; wherein the at least one term of the DSI equation is multiplied by a coefficient specific to the liver function test, and the DSI equation comprises one or more additional terms representing values from clinical biochemistry laboratory assays selected from the group consisting of serum albumin, alanine transaminase, aspartate transaminase, alkaline phosphatase, total bilirubin, direct bilirubin, gamma glutamyl transpeptidase, 5' Nucleotidase, PT-INR (prothrombin time-international normalized ratio), caffeine elimination, antipyrine clearance, galactose elimination capacity, formation of MEGX from lidocaine, methacetin-C13, and methionine-C13; and/or one or more additional terms representing clinical features selected from varices, ascites, or hepatic encephalopathy.

In some embodiments, a method is provided for diagnosing rate of progression of primary sclerosing cholangitis (PSC) in a patient, the method comprising: determining a SHUNT test value or a Portal HFR test value in a patient having PSC; employing the SHUNT test value or Portal HFR test value in an algorithm to provide an algorithm result, wherein the algorithm comprises a term representing the age of the patient in years at the time of the determining step; and comparing the algorithm result to a known cut-off value to diagnose the rate of progression of PSC in the patient. In some embodiments, a method is provided for diagnosing rate of progression of primary sclerosing cholangitis (PSC) in a patient, wherein if a SHUNT test value (in %) in the patient divided by the age of the patient is greater than 1.7; then the rate of progression of primary sclerosing cholangitis (PSC) in the patient is rapid, and the patient having PSC is diagnosed as a Rapid Progressor.

In some embodiments, a method is provided for diagnosing rate of progression of primary sclerosing cholangitis (PSC) in a patient, wherein if a SHUNT test value (in %) in the patient divided by the age of the patient is less than 1.7; and portal HFR (in mL/min/kg)+[0.35×age]>29; then the rate of progression of primary sclerosing cholangitis (PSC) in the patient is slow, and the patient having PSC is diagnosed as a Slow Progressor.

In some embodiments, a method is provided for diagnosing rate of progression of primary sclerosing cholangitis (PSC) in a patient, wherein if a SHUNT test value (in %) in the patient divided by the age of the patient is less than 1.7; and portal HFR (in mL/min/kg)+[0.35×age]<29; then the rate of progression of primary sclerosing cholangitis (PSC) in the patient is moderate, and the patient having PSC is diagnosed as a Moderate Progressor.

BRIEF DESCRIPTION OF THE DRAWINGS

FIG. 19, panel B shows hepatic functional improvement in SHUNT, portal HFR and DSI, from left to right, after SVR following retreatment of chronic HCV patients with PEG/RBV (peginterferon/ribavirin). More severe baseline impairment resulted in greater functional improvement after SVR when tested two years after baseline.

DETAILED DESCRIPTION OF THE INVENTION

The methods and tests disclosed herein are based on a new view of chronic liver disease, that it is the disruption of the portal blood flow, not fibrosis per se, that is deleterious and should be targeted for analysis of liver function.

Previously disclosed liver function tests, the Portal HFR (Portal hepatic filtration rate, FLOW) test and the SHUNT test, are used to accurately measure portal blood flow and were previously validated using a large cohort of patients with chronic hepatitis C. The portal HFR and SHUNT tests for liver function in patients with chronic hepatitis C were disclosed in prior applications by the present inventors.

Figure 3:
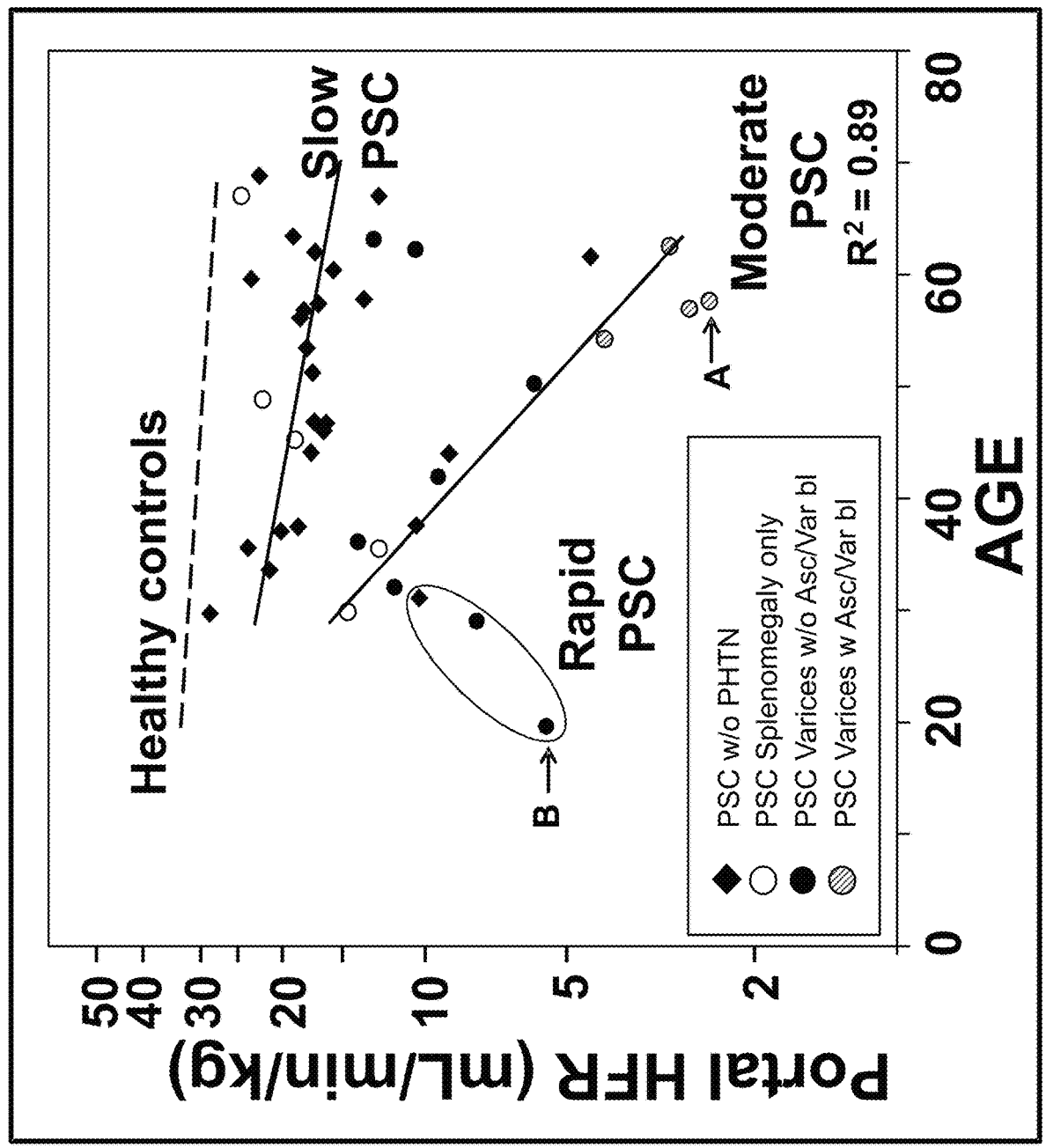
FIG. 3 shows Portal HFR vs. age in PSC patients. PHC patients could be segregated into distinct groups based on their Portal HFR test values and age at the time of testing.
Figure 4:
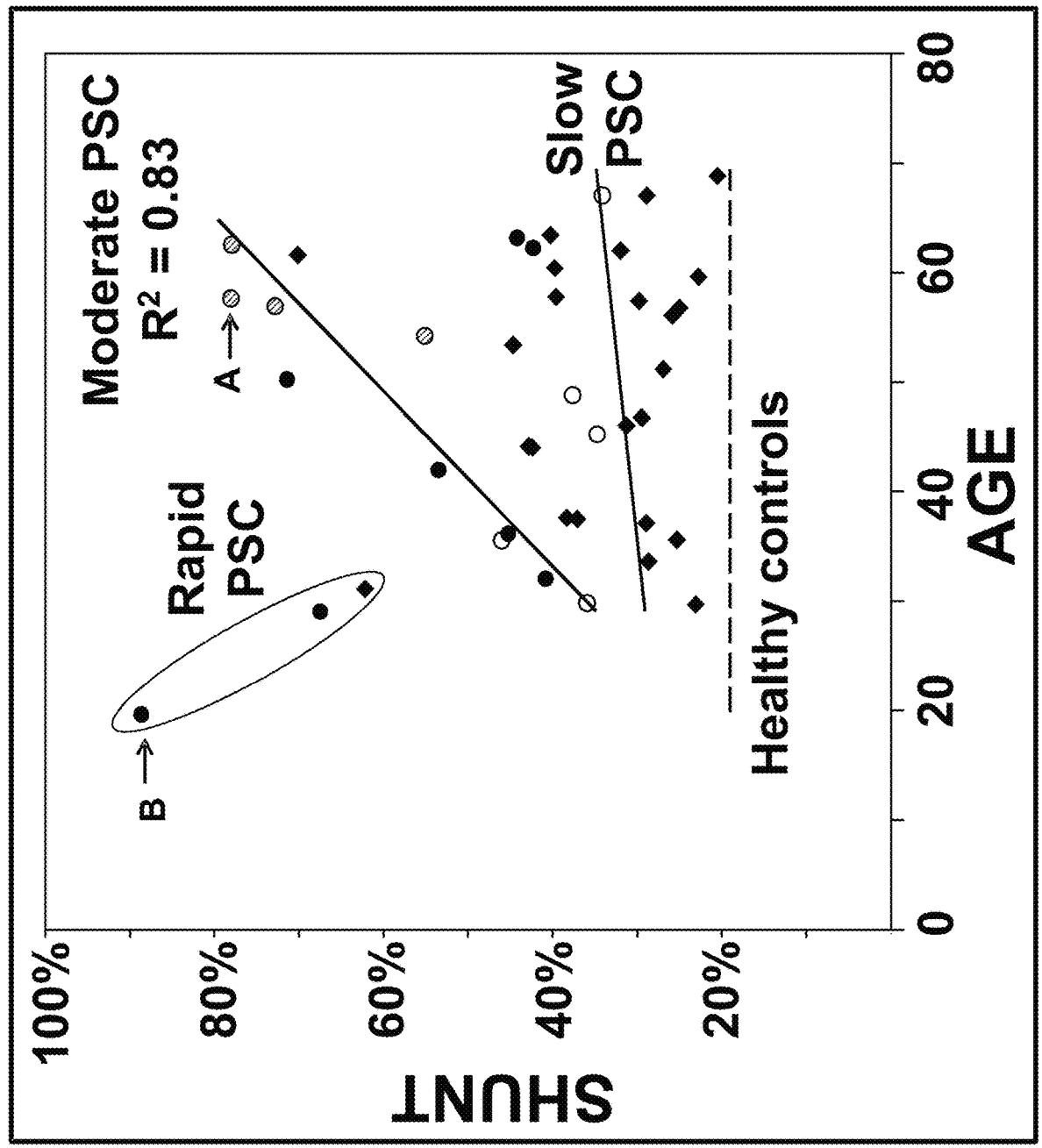
FIG. 4 shows PSC patients could be segregated into distinct groups based on their SHUNT test values vs. age at the time of testing.

In some embodiments, it has been surprisingly found that when either the portal HFR result or the SHUNT result was divided by age, the functional assessment was able to define categories of disease in PSC. PSC patients segregated into distinct groups based on their Portal HFR and SHUNT values and age at the time of testing. Slow PSC patients had only modest declines in function compared to controls. Moderate and rapid PSC patients exhibited more complications and at earlier ages. Slow, Moderate and Rapid Progressors could be differentiated by using either portal HFR divided by age (FIG. 3) or SHUNT divided by age (FIG. 4). To the best of the inventor's knowledge, this is the first time that functional assessment defined categories of disease in PSC.

Chronic liver diseases (CLDs) are all characterized by a similar pathophysiology with inflammation, cell death, and fibrosis leading to a progressive disruption of the hepatic microvasculature so a test to measure portal blood flow will work for assessment of all CLDs.

Almost all the other proposed tests to assess chronic liver disease have focused on fibrosis, either on serum biomarkers or the change in tissue elasticity (Mukherjee and Sorrell, 2006, Noninvasive tests for liver fibrosis. Semin Liver Dis. 26: 337-347; Manning and Afdhal, 2008. Diagnosis and quantitation of fibrosis. Gastroenterology. 134: 1670-1681; Poynard et al., 2008, Concordance in a world without a gold standard: A new non-invasive methodology for improving accuracy of fibrosis markers. PLoS One. 3: e3857).

Both fibrosis and microvasculature disruption do increase as disease progresses but they are not perfectly linked. This explains why patients with extreme fibrosis, cirrhosis, can remain stable as long as their portal flow is maintained above a critical threshold. It also explains why those patients with only moderate fibrosis but severely impaired flow can have serious complications. This new insight can change the whole focus of liver disease assessment. By targeting the portal flow physicians can easily detect early stage liver disease, accurately assess the status of their patients, and predict clinical outcomes. More effective treatments for liver disease can result from having research on new therapies and new drugs focus on improving and/or maintaining the portal flow.

Chronic Hepatitis C. Hepatitis C is an infectious disease affecting the liver and caused by the hepatitis C virus (HCV). HCV infection can go undetected for many years and is often asymptomatic. However, chronic infection can lead to scarring of the liver, cirrhosis and liver failure, liver cancer or life-threatening esophageal and gastric varices. Patients with cirrhosis or liver cancer may require a liver transplant, although the virus can reoccur after transplantation. Standard therapy includes peginterferon with ribavirin, and clinical trials involving further combination with bocepravir or telepravir are ongoing. Globally, about 180 million people are infected with HCV. Rosen, Chronic Hepatitis C Infection, N Engl J Med 2011; 364:2429-38.

There are a number of diagnostic tests available to detect HCV infection including HCV antibody enzyme immunoassay (ELISA), recombinant immunoblot assay, and HCV RNA polymerase chain reaction (PCR). However, chronic infections are typically asymptomatic and are most often discovered following investigation of elevated liver enzyme levels or during routine screening. Unfortunately, diagnostic testing cannot distinguish between acute and chronic cases. In addition, liver enzymes are poorly correlated with disease severity. Liver biopsies are used to determine the degree of liver damage present, but there are risks from the procedure. Better non-invasive tests for liver function have recently been developed.

Two known liver function tests, the Portal HFR (Portal hepatic filtration rate, FLOW) test and the SHUNT test, have been used to accurately measure portal blood flow and were previously validated using a large cohort of patients with chronic hepatitis C. The portal HFR and SHUNT tests for liver function in patients with chronic hepatitis C were disclosed in prior applications by the present inventors.

Nonalcoholic Fatty Liver Disease. Non-Alcoholic Fatty Liver Disease (NAFLD) (Browning et al., 2004, Prevalence of hepatic steatosis in an urban population in the United States: Impact of ethnicity. Hepatology. 40: 1387-1395) may affect up to one-third of the US population and this vast epidemic is mostly hidden because people are usually asymptomatic and have normal 'liver function tests'—clinical biochemistry laboratory blood assays such as serum albumin, alanine transaminase, aspartate transaminase, alkaline phosphatase, total bilirubin, direct bilirubin, and gamma glutamyl transpeptidase. The prevalence of NAFLD continues to rise along with the major risk factors which are obesity, metabolic syndrome, and insulin resistance. NAFLD can progress from simple fatty liver called steatosis, which is relatively benign, to the more serious NASH, Non-Alcoholic SteatoHepatitis. Hepatitis is inflammation of the liver and can also be caused by excessive drinking, as in Alcoholic SteatoHepatitis (ASH), or viral infection, i.e., Chronic Hepatitis C (CHC). All these chronic liver diseases (CLDs) are characterized by a similar patho-physiology with inflammation, cell death, and fibrosis leading to a progressive disruption of the hepatic microvasculature. About 5% of NAFLD patients will progress to cirrhosis (Adams et al., 2005, The natural history of nonalcoholic fatty liver disease: A population-based cohort study. Gastroenterology. 129: 113-121) and NAFLD will surpass CHC as the leading indication for liver transplantation.

Difficulties in Monitoring Patients with Chronic Liver Disease. Currently the only way to distinguish Non-Alcoholic SteatoHepatitis (NASH) from steatosis and to monitor NASH progression is through a needle biopsy, which assesses the grade of inflammatory activity and the stage of fibrosis. Biopsy is considered the gold standard despite suffering from numerous sources of inaccuracy and the risks of an invasive procedure. Patients must be sedated and a portion will experience bleeding and other complications (Janes and Lindor, 1993, Ann Intern Med. 118: 96-98; Seeff et al., 2010, Clin Gastroenterol Hepatol. 8: 877-883). The needle biopsy is a very small specimen of a very large organ and it is very difficult to obtain large enough pieces from enough locations for adequate sampling (Vuppalanchiet al., 2009, Clin Gastroenterol Hepatol. 7: 481-486; Bedossa et al., 2003, Hepatology. 38: 1449-1457; Regevet al., 2002, Am J Gastroenterol. 97: 2614-2618). Biopsy interpretation is subjective and depends on the expertise of the observer (Rousselet et al., 2005, Hepatology. 41: 257-264) and the size and number of tissue samples (Rousselet et al., 2005; Vuppalanchiet al., 2009). In describing the progression of fibrosis in CHC the 6 stage Ishak system (Ishak et al., 1995, J Hepatol. 22: 696-699) may be used, but more typical is a simpler 4 stage system (Knodell et al., 1981, Hepatology. 1: 431-435; Batts and Ludwig, 1995, Am J Surg Pathol. 19: 1409-1417; Scheuer, 1991, J Hepatol. 13: 372-374) such as Metavir (Group, TFMCS, 1994, Hepatology. 20: 15-20) which is very comparable to the 4 stage system used for NASH (Brunt et al.,1999, Am J Gastroenterol. 94: 2467-2474; Kleiner et al., 2005. Hepatology 41: 1313-1321). However, the heterogeneity of lesions in NASH decreases the accuracy (Ratziu et al., 2005, Gastroenterology. 128: 1898-1906). It is not practical to biopsy a third of the population especially since the method has an estimated error rate of 20% or greater. Other standard liver blood tests are not very useful. Liver enzymes such as ALT or AST may spike during activity flares, but often they are in the normal range due to the slow rate of progression. The liver's production of albumin or clotting factors only declines at the latest stages of CLD. Noninvasive means to distinguish NASH from steatosis and accurately monitor NASH progression are desirable.

Deficiencies of Other Non-invasive Test Methods. The need for non-invasive liver assessment has led to the commercialization of new methods by others including biomarker panels, metabolic breath tests, and transient elastography. Each of these other non-invasive test methods suffers from disadvantages.

Biomarker panels (Mukherjee and Sorrell, 2006, Noninvasive tests for liver fibrosis. Semin Liver Dis. 26:337-347; Shah et al., 2009, Comparison of noninvasive markers of fibrosis in patients with nonalcoholic fatty liver disease. Clin Gastroenterol Hepatol. 7:1104-1112) such as FIBROTEST® biochemical markers are not sensitive enough to detect either early stage CHC (Boursier et al., 2009. Improved diagnostic accuracy of blood tests for severe fibrosis and cirrhosis in chronic hepatitis c. Eur J Gastroenterol Hepatol. 21:28-38; Shaheen et al., 2007, "FIBROTEST and FIBROSCAN for the prediction of hepatitis c-related fibrosis: A systematic review of diagnostic test accuracy." Am J Gastroenterol. 102:2589-2600) or NASH (Ratziu et al., 2006, "Diagnostic value of biochemical markers (FIBROTEST-FIBROSURE) for the prediction of liver fibrosis in patients with non-alcoholic fatty liver disease." BMC Gastroenterol. 6:6; Angulo et al., 2007, The NAFLD fibrosis score: A noninvasive system that identifies liver fibrosis in patients with NAFLD. Hepatology. 45:846-854; Wong et al., 2010, Diagnosis of fibrosis and cirrhosis using liver stiffness measurement in nonalcoholic fatty liver disease. Hepatology. 51:454-462) or to track progression because circulating proteins/fragments can't report accurately on fine structure, the disruption of the microvasculature, and impairment of flow.

Metabolic breath tests are variable because they rely on cytochrome P450 (CYP) enzymes which vary according to gender, age, genetics, diet, medications and they are insensitive to early stage disease because the enzymes do not significantly decline until later stages. BreathID® has a methacetin metabolic test in FDA trials, but this method failed to detect early stage CHC in earlier studies (Braden et al., 2005. $^{13}$C-methacetin breath test as liver function test in patients with chronic hepatitis c virus infection. Aliment Pharmacol Ther. 21: 179-185).

FIBROSCAN® transient elastography, also in FDA trials, uses transient elastography to measure liver stiffness to estimate fibrosis (Del Poggio and Colombo, 2009. Is transient elastography a useful tool for screening liver disease? World J Gastroenterol. 15:1409-1414). This method is insensitive to early stage CLD (Del Poggio and Colombo, 2009, infra; Friedrich-Rust et al., 2008. Performance of transient elastography for the staging of liver fibrosis: A meta-analysis. Gastroenterology. 134:960-974) including CHC (Shaheen et al., 2007, infra, and Rossi et al., 2003. "Validation of the FIBROTEST biochemical markers score in assessing liver fibrosis in hepatitis c patients." Clin Chem, 49:450-454) or NASH (Wong et al., 2010, Diagnosis of fibrosis and cirrhosis using liver stiffness measurement in nonalcoholic fatty liver disease. Hepatology. 51:454-462) and is compromised by obesity, a major risk factor for NAFLD. More effective noninvasive means to distinguish NASH from steatosis and accurately monitor NASH progression are clearly needed.

The new focus on portal flow could revolutionize how chronic liver disease is staged and monitored. Biopsy would still be useful in the initial diagnosis to rule out auto-immune disease and inherited disorders but would not be used to assess patients' status or follow them over time. Impairment of portal flow would be used to guide management and determine when it would be appropriate to screen for varices and hepatocellular carcinoma. Portal flow would be a new more accurately determined endpoint for clinical trials.

Figure 1:
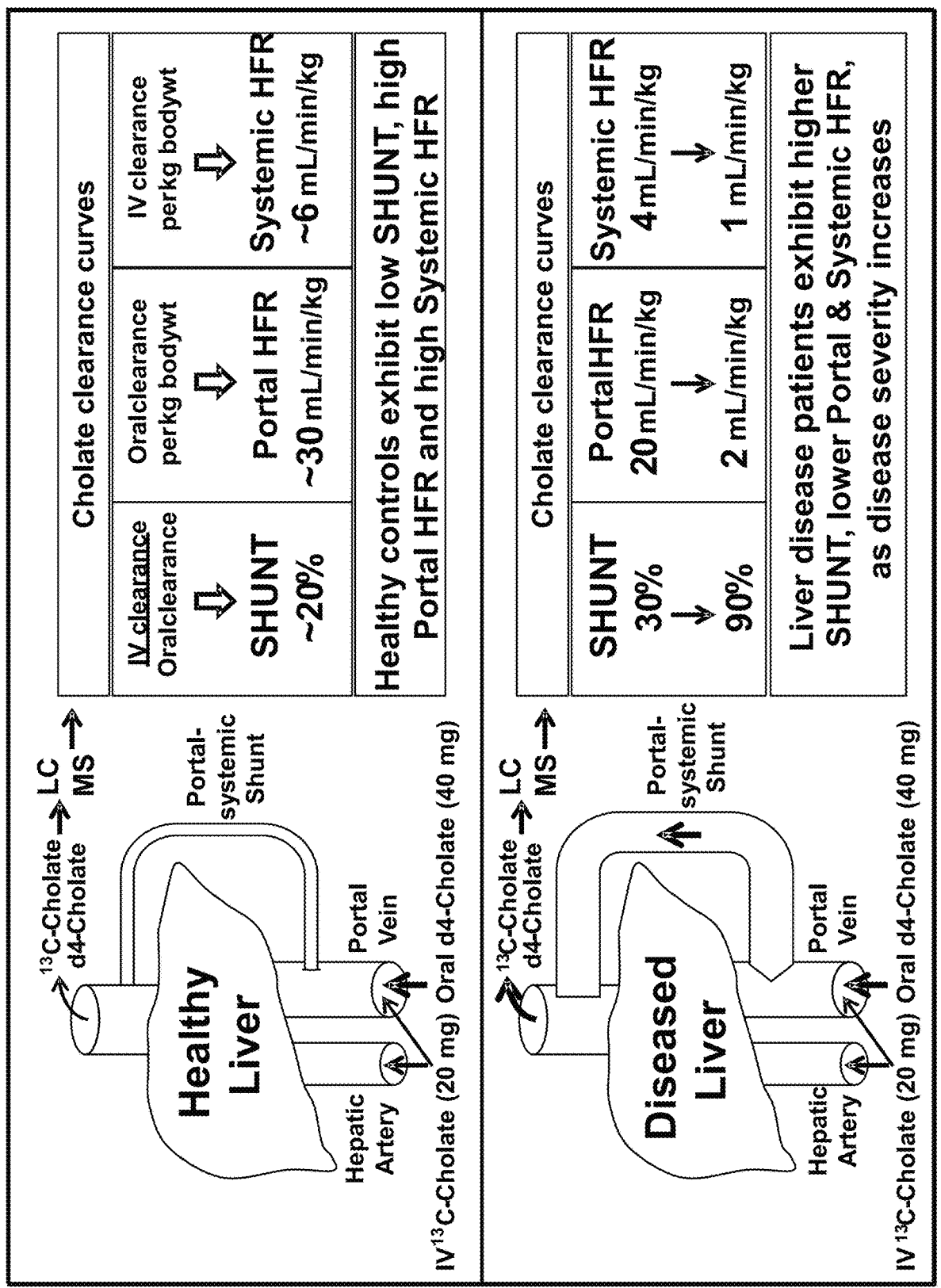
FIG. 1 shows a schematic of the Portal HFR and SHUNT tests. Healthy controls (upper panel) generally exhibit low SHUNT, high Portal HFR and high Systemic HFR; whereas subjects with liver disease (lower panel) such as PSC exhibit higher SHUNT, lower Portal HFR and lower Systemic HFR.

A schematic of the previously disclosed portal HFR and SHUNT tests is shown in FIG. 1. The oral cholate clearance (dose/area under oral clearance curve) is a measure of the effective portal blood flow. The oral clearance per kg body weight is used to determine the portal HFR. The IV cholate clearance (dose/area under IV clearance curve) is a measure of the total hepatic blood flow. The IV clearance per kg body weight determines the systemic HFR. The ratio of IV to oral clearances assesses the portal-systemic shunt fraction (SHUNT). In one aspect, the disclosure provides methods wherein the oral cholate clearance or portal HFR can be estimated from the oral cholate serum concentration at a single time point, for example, at 60 minutes after administration (STAT).

A schematic of the portal HFR and SHUNT tests is shown in FIG. 1. FIG. 1 shows that healthy controls (upper panel) generally exhibit low SHUNT, high portal HFR and high Systemic HFR; whereas subjects with liver disease (lower panel) such as PSC exhibit higher SHUNT, lower portal HFR and lower systemic HFR.

In health, the orally administered deuterated cholate is delivered to the liver via the portal circulation. Its clearance is a measure of the portal circulation—hence the designation Portal HFR. The intravenously administered $^{13}$C-cholate is delivered to the liver via both hepatic arterial and portal venous circulations—hence the designation Systemic HFR. SHUNT is a ratio of Systemic HFR to Portal HFR. The normal ranges for these tests are shown in the top panels.

With disease—SHUNT increases and both portal and systemic HFR decrease—as shown in the bottom panels.

For example, normal healthy controls typically exhibit SHUNT (IV cholate clearance/oral cholate clearance) of about 20%, portal HFR (oral cholate clearance per kg body weight) of about 30 mL/min/kg, and systemic HFR (intravenous cholate clearance per kg body weight) of about 6 mL/min/kg. Liver disease patients typically exhibit higher SHUNT values of between from about 30% to 90%. Liver disease patients typically exhibit lower portal HFR of from about 20 mL/min/kg to about 2 mL/min/kg. Liver disease patients typically exhibit lower systemic HFR of from about 4 mL/min/kg to about 1 mL/min/kg.

In the diseased liver, as more blood escapes extraction by intra- and extra-hepatic shunting to the systemic circulation, the SHUNT increases, HFR or portal flow decreases, and STAT increases. In a normal control subject, the effective portal blood flow (portal HFR, FLOW) is high in a healthy liver due to low vascular resistance. Portal-systemic shunting (SHUNT) is minimal. Oral cholate at 60 min (STAT) is low. For example, in a healthy control FLOW=37 mL min$^{-1}$ kg$^{-1}$, SHUNT=18% and STAT=0.2 µM. However, in a subject with liver disease, inflammation, fibrosis, and increased vascular resistance reduce the effective portal blood flow (FLOW). Portal-systemic shunting (SHUNT) is increased. Oral cholate at 60 min (STAT) is high. For example in a CHC F2 patient, FLOW=9 mL min$^{-1}$ kg$^{-1}$, SHUNT=35% and STAT=1.6 µM.

Portal HFR (FLOW) and SHUNT tests are used to determine portal blood flow and liver function, for example, in healthy controls and patients with chronic hepatitis C; these tests are disclosed in US 2010/0055734 and US2008/0279766, which are each incorporated herein by reference. The STAT test was developed as a screening test and is utilized to estimate portal blood flow and screen large populations for detection of patients with chronic liver disease, including chronic hepatitis C, PSC and NAFLD. The STAT test was developed to estimate portal blood flow and screen large populations for detection of patients with chronic liver disease, including chronic hepatitis C, PSC and NAFLD. The relationship of STAT to prior art methods of determining clearance of cholate from the portal circulation, specifically the FLOW and SHUNT tests, has been validated using a large cohort of patients with chronic hepatitis C. The STAT test is disclosed in U.S. Ser. No. 13/484,083, filed May 30, 2012, which is incorporated herein by reference.

In some embodiments, the portal HFR value in the patient is estimated from a STAT test value in the subject, wherein the STAT test value in the subject is obtained by a method comprising (a) receiving a single blood or serum sample collected from the subject having PSC, following oral administration of a dose of a distinguishable cholate compound (dose$_{oral}$) to the subject, wherein the sample has been collected from the subject at a specific time point within about 20-180 minutes after administration; (b) measuring concentration of the distinguishable cholate compound in the sample.

In some embodiments, the systemic HFR value in the patient is determined by a method comprising (a) receiving a plurality of blood or serum samples collected from a patient having or at risk of a chronic liver disease, following intravenous administration of a dose of a distinguishable cholate (dose$_{oral}$) to the patient, wherein the samples have been collected from the patient over intervals spanning a period of time after administration; (b) measuring concentration of the distinguishable cholate in each sample; (c) generating an individualized intravenous clearance curve from the concentration of the distinguishable cholate in each sample comprising using a computer algorithm curve fitting to a model distinguishable cholate clearance curve; (d) computing the area under the individualized oral clearance curve (AUC)(mg/mL/min) and dividing the dose (in mg) by AUC of the intravenously administered stable isotope labeled cholic acid to obtain the intravenous cholate clearance in the patient; and (e) dividing the intravenous cholate clearance by the weight of the patient in kg to obtain the portal HFR value in the patient (mL/min/kg).

In some embodiments, the single blood or serum sample in the STAT test is collected at one single time point selected from about 20. 25, 30, 35, 40, 45, 50, 55, 50, 65, 70, 75, 80, 85, 90, 95, 100, 105, 110, 115, 120, 125, 130, 135, 140, 145, 150, 155, 160, 165, 170, 175, or 180 minutes, or any time point in between, after oral administration of the distinguishable cholate compound.

In some embodiments, the single blood or serum sample in the STAT test is collected at one time point selected from about 45, about 60 or about 90 minutes after oral administration of the distinguishable cholate compound.

In some embodiments, the single blood or serum sample is collected at about 60 minutes after oral administration of the distinguishable cholate compound.

In some embodiments, the single blood or serum sample is collected at about 45 minutes after oral administration of the distinguishable cholate compound.

In some embodiments, the single blood or serum sample is collected at about 90 minutes after oral administration of the distinguishable cholate compound.

In some embodiments, the estimated hepatic blood flow (HBF) is calculated with the following equation:

HBF=(Cholate clearance after intravenous administration)/[1−(SHUNT/100))×(1−(Hematocrit %/100))]

Previously, human studies demonstrated the clinical utility of FLOW and SHUNT testing in CHC. A number of new liver tests have been proposed over the years but there have been few studies to directly compare their efficacy and actual clinical utility. A very large multicenter HALT-C trial was conducted whose main objective was to determine the efficacy of long term hepatitis C virus suppression but which also included an ancillary study to evaluate a battery of new quantitative liver function tests. (Everson et al., 2009. Quantitative tests of liver function measure hepatic improvement after sustained virological response: Results from the HALT-C trial. Aliment Pharmacol Ther. 29: 589-601). Nearly 300 patients with advanced (Ishak F2-6) but compensated CLD were tested. A recently completed Early CHC study compared these tests in 25 healthy controls and 23 early stage (Ishak F1-2) CHC patients in order to examine the entire spectrum of this CLD. The liver's metabolic capacity was assessed using caffeine, antipyrine, lidocaine, and galactose tests. All these activities were reduced in patients with cirrhosis, but none were different in early stage CHC patients compared to healthy controls. (Everson et al., 2008. The spectrum of hepatic functional impairment in compensated chronic hepatitis c: Results from the hepatitis c anti-viral long-term treatment against cirrhosis trial. Aliment Pharmacol Ther. 27: 798-809). These results suggest that metabolic capacity is maintained until there is significant loss of functional parenchyma in later stage CLD. In HALT-C the patients were tested serially every 2 years and followed to monitor outcomes. FLOW, using a cutoff of <9.5 ml/min/kg, was superior to the other tests in predicting clinical outcomes with the highest sensitivity, specificity, positive predictive value (PPV), negative predictive value (NPV) and the best performance by ROC analysis (Quantitative Liver Function Tests Improve the Prediction of Clinical Outcomes in Chronic Hepatitis C: Results from the HALT-C Trial, Everson et al, submitted to Gastroenterology). FLOW had a higher ROC c statistic (0.84) relative to SHUNT (0.79). The improvement after SVR was more significant for FLOW (p=0.0002) than for SHUNT (p=0.0003) (Everson et al., 2009, infra). In the Early CHC study, FLOW decreased from 34±14 ml/min/kg (mean±SD) in controls to 23±10 ml/min/kg in early CHC (p<0.002) but the increase in SHUNT (20±6% in controls vs, 31±14% in early CHC patients p<0.0002) was more statistically significant. None of the other tests could distinguish early stage CHC patients from healthy controls. These results suggest that SHUNT and FLOW outperform other functional tests in detecting early liver disease, tracking patients, and predicting clinical outcomes.

Disease Severity Index (DSI)

Although various direct cut-offs for the FLOW and SHUNT tests were previously developed for specific conditions, in some cases use of a Disease Severity Index (DSI) more clearly delineates patient categories in chronic liver disease.

The "Disease Severity Index" (DSI) employs a mathematical model designed for adaptation of a bioassay result (liver function test) to the assessment of disease severity of an individual patient. For example, a DSI equation is developed using liver function test results from a defined patient population and healthy controls. In some embodiments, a DSI equation is developed from a specific patient population. The DSI equation has one or more terms selected from SHUNT, Portal HFR, and/or Systemic HFR depending on type or severity of liver disease. In some embodiments, one or more DSI cut-offs are used for DSI comparison, depending on type of disease and severity of disease. In some embodiments, use of the DSI in a patient requires only a simple table look up.

In some embodiments, a method of determining disease severity index (DSI) in a patient with chronic liver disease comprises (a) obtaining one or more liver function test values in a patient having a chronic liver disease, wherein the one or more liver function test values are obtained from one or more liver function tests selected from the group consisting of SHUNT, Portal HFR and Systemic HFR; and (b) employing a disease severity index equation (DSI equation) comprising one or more terms and a constant to obtain the DSI; where at least one term of the DSI equation independently represents a liver function test value in the patient, or a mathematically transformed liver function test value in the patient; and the at least one term of the DSI equation is multiplied by a coefficient specific to the liver function test. In some embodiments, the mathematically transformed liver function test value in the patient is selected from a log, antilog, natural log, natural antilog, or inverse of the liver function test value in the patient. In some embodiments, each term of the DSI equation represents a liver function test value or a mathematically transformed liver function test value.

The constant and coefficient(s) of the DSI equation can vary with liver disease type and/or disease severity. In some embodiments, the constant and coefficients are interrelated so, for example, if all were divided by 10 then the DSI would go from 0-5, rather than 0-50, and healthy would be 1 instead of 10. In some embodiments, the constant is a positive number between 5 and 125. In some embodiments, the SHUNT coefficient is a number between 0 and positive 25. In some embodiments, the Portal HFR coefficient is a number between 0 and negative 25. In some embodiments, the Systemic HFR coefficient is a number between 0 and negative 25.

In some embodiments, the at least one term in the DSI equation is multiplied by a coefficient specific to each type of test, to obtain the DSI. In some embodiments, the DSI in the patient is compared to one or more DSI cut-off values indicative of at least one clinical outcome.

In some embodiments, the disclosure provides a method of determining disease severity index (DSI) in a patient with chronic liver disease, the method comprising (a) obtaining a SHUNT test value and a Portal HFR test value from a patient having a chronic liver disease; and (b) employing a disease severity equation comprising a first term for the SHUNT test value and a second term for the Portal HFR value to obtain the DSI.

In a specific embodiment, a DSI equation was developed by use of cholate testing that was performed at baseline in 224 chronic HCV patients (Ishak F2-F6) enrolled in the HALT-C clinical trial, characterized by CTP scores of 5 or 6 and no prior history of clinical complications.

Specifically, archive serum was re-analyzed to determine cholate clearance curves for systemic Hepatic Filtration Rate (HFR) from clearance of intravenously administered cholate, Portal HFR from orally administered cholate, and SHUNT from the ratio of clearances using an improved LCMS method validated to FDA guidelines. Patients were followed for clinical outcomes for up to 8.3 years (4.9±2.2 years, mean±SD). Clinical outcomes (n=54) were defined as CTP progression, variceal hemorrhage, ascites, hepatic encephalopathy, or liver-related death.

Derivation of a Disease Severity Index (DSI) was performed using univariate Cox univariate Cox proportional hazard regression analysis as shown in Example 10, Table 13. Ageneric equation was developed using SHUNT, portal HFR and systemic HFR from cholate testing.

$$DSI=A(SHUNT)+B(\log_e \text{ portal HFR})+C(\log_e \text{ systemic HFR})+D.$$

A DSI equation was developed based on prediction of first clinical outcome in the HALT-C cohort:

$$DSI=5.75 \text{ (SHUNT)}-7.22 \text{ (Log}_e \text{ Portal HFR)}-8.45 \text{ (Log}_e \text{ Systemic HFR)}+50.$$

Surprisingly, although this DSI equation was developed in a cohort of HCV patients, it has provided accurate assessment of disease severity in other chronic liver diseases primary sclerosing cholangitis (PSC) and non-alcoholic fatty liver disease (NAFLD), for example, as provided in, for example, Examples 9-13.

In some embodiments, a cholate test based DSI is used in a method to differentiate PSC patients from healthy controls, listed PSC patients from PSC patients not listed for liver transplant, and listed patients with varices from those without varices, as shown in Example 12.

In some embodiments, a DSI value in a PSC patient based on dual oral and intravenous cholate clearances may be superior to MELD score in assessing the risks for complications and priority for liver transplant in PSC.

In some embodiments, cholate testing and DSI is used in a method for identifying chronic liver disease patients at risk for portal hypertension and/or decompensation, where portal hypertension (PHTN) is defined as splenomegaly or varices, and decompensation is defined as ascites or variceal hemorrhage.

In some embodiments, the chronic liver disease is selected from chronic hepatitis C (CHC), chronic hepatitis B, alcoholic liver disease, Alcoholic SteatoHepatitis (ASH), and Non-Alcoholic Fatty Liver Disease (NAFLD) which can progress from simple fatty liver called steatosis, which is relatively benign, to the more serious Non-Alcoholic SteatoHepatitis (NASH), autoimmune liver disease, cryptogenic cirrhosis, hemochromatosis, Wilson's disease, alpha-1-antitrypsin deficiency, primary sclerosing cholangitis (PSC) and other cholestatic liver diseases.

In some embodiments, a method for determining a disease severity index (DSI) value in a patient is provided, the method comprising obtaining serum samples from a patient suffering from a chronic liver disease, wherein the patient previously received oral administration of a first stable isotope cholate and simultaneously intravenous administration of a second stable isotope cholate, and wherein blood samples had been collected from the patient over an interval of less than 180 minutes following administration of the cholates; assaying the serum samples to calculate the portal hepatic filtration rate (portal HFR) as mL/min/kg, wherein kg is body weight of the patient, the systemic hepatic filtration rate (systemic HFR) as mL/min/kg wherein kg is body weight of the patient, and SHUNT as %; and calculating a DSI value for the patient by using the equation:

$$DSI=5.75 \text{ (SHUNT)}-7.22 \text{ (Log}_e \text{ Portal HFR)}-8.45 \text{ (Log}_e \text{ Systemic HFR)}+50.$$

In some embodiments, the DSI value is used in a method for identifying increased risk for portal hypertension or decompensation in the chronic liver disease patient wherein a DSI greater than 18 indicates increased risk for portal hypertension (PHTN), and a DSI greater than 36 indicates an increased risk for decompensation, where portal hypertension (PHTN) is defined as splenomegaly or varices, and decompensation is defined as ascites or variceal hemorrhage.

In some embodiments, the DSI value is used in a method for prediction of clinical outcomes in the chronic liver disease patient, wherein a DSI>25 indicates an increased risk of clinical outcome in the patient. In some embodiments, the chronic liver disease is chronic hepatitis C and the clinical outcome is selected from CTP progression, variceal hemorrhage, ascites, hepatic encephalopathy, or liver-related death.

In some embodiments, the DSI value is used in a method for prediction of sustained virological response in a patient suffering from chronic hepatis B or chronic hepatitis C following antiviral treatment, wherein decrease in DSI value in the patient over time following antiviral treatment is indicative of sustained virological response.

In some embodiments, the DSI value in a patient having a chronic liver disease is used for prioritizing the patient on the waiting list for liver transplant (LT), comprising increasing the priority of the patient on the waiting list for LT following an increase in the DSI value over time in the patient, or following a DSI value of greater than 40 when the DSI value is obtained according to the equation:

$$DSI=5.75 \text{ (SHUNT)}-7.22 \text{ (Log}_e \text{ Portal HFR)}-8.45 \text{ (Log}_e \text{ Systemic HFR)}+50$$

where SHUNT is SHUNT test value in the patient (%), portal HFR is portal HFR test value in the patient as mL/min/kg, wherein kg is body weight of the patient, and systemic HFR is systemic HFR value in the patient as mL/min/kg, wherein kg is body weight of the patient, wherein the SHUNT and the portal HFR test values in the patient were obtained on the same day.

In some embodiments, the DSI value in a patient having a chronic liver disease is used in a method for prediction of future clinical outcome or identifying patients with medium/large varices, when the DSI value in the patient is obtained according to the equation:

$$DSI=5.34 \text{ SHUNT}-6.65 \text{ Loge Portal HFR}-8.57 \text{ Loge Systemic HFR}+44.66$$

wherein a DSI>19 indicates high risk of medium to large varices; DSI10-19 is indicative of low risk of medium/large varices; and DSI of 0-10 is indicative of healthy liver function; and a DSI>19 indicates high risk of clinical outcomes; DSI10-19 is indicative of low risk of clinical outcomes; and DSI of 0-10 is indicative of healthy liver function.

In some embodiments, the chronic liver disease is selected from chronic hepatitis C, non-alcoholic fatty liver disease (NAFLD), or primary sclerosing cholangitis (PSC).

In some embodiments, a method is provided for identifying increased risk for portal hypertension or decompensation in a chronic liver disease patient, the method comprising obtaining serum samples from a patient suffering from a chronic liver disease, wherein the patient previously received oral administration of a first stable isotope cholate and simultaneously intravenous administration of a second stable isotope cholate, and wherein blood samples had been collected from the patient over an interval of less than 180 minutes following administration of the cholates; assaying the serum samples to calculate the portal hepatic filtration rate (portal HFR) as mL/min/kg, wherein kg is body weight of the patient, the systemic hepatic filtration rate (systemic HFR) as mL/min/kg wherein kg is body weight of the patient, and SHUNT as %; calculating a DSI value for the patient by using the equation: DSI=5.75 (SHUNT)−7.22 ($Log_e$ Portal HFR)−8.45 ($Log_e$ Systemic HFR)+50, wherein a DSI greater than 18 indicates increased risk for portal hypertension (PHTN), and a DSI greater than 36 indicates an increased risk for decompensation.

In some embodiments, a method is provided for calculating a disease severity index (DSI) value for a patient, the method comprising obtaining serum samples from a patient suffering from or at risk of a chronic liver disease, wherein the patient previously received oral administration of a first stable isotope cholate and simultaneously intravenous administration of a second stable isotope cholate, and wherein blood samples had been collected from the patient over an interval of less than 180 minutes following administration of the cholates; assaying the serum samples to calculate the portal hepatic filtration rate (portal HFR) as mL/min/kg, wherein kg is body weight of the patient, the systemic hepatic filtration rate (systemic HFR) as mL/min/kg wherein kg is body weight of the patient, and SHUNT as %; calculating a DSI value for the patient by using the equation: DSI=5.75 (SHUNT)−7.22 ($Log_e$ Portal HFR)−8.45 ($Log_e$ Systemic HFR)+50.

In some embodiments, the SHUNT, systemic HFR, and portal HFR test values in the patient are obtained on the same day.

In some embodiments, cholate testing DSI is used for adjust the priority for liver transplantation for chronic liver disease patients on the waiting list.

In some embodiments, cholate testing DSI is used to adjust the priority for liver transplantation for chronic liver disease patients on the waiting list, wherein the chronic liver disease is chronic hepatitis C, NAFLD or primary sclerosing cholangitis (PSC).

In another specific embodiment, a DSI equation was developed using portal HFR and SHUNT test values from HCV patients:

DSI=9.84 (SHUNT)−12.36 LOGe (portal HFR)+50.5 where SHUNT is SHUNT test value in the patient and portal HFR is portal HFR test value in the patient. In some embodiments, the SHUNT and the portal HFR test values in the patient were obtained on the same day.

In some embodiments, a DSI equation has one or more additional terms representing a different clinical biochemistry laboratory blood assays such as serum albumin, alanine transaminase, aspartate transaminase, alkaline phosphatase, total bilirubin, direct bilirubin, gamma glutamyl transpeptidase, 5' Nucleotidase, PT-INR (prothrombin time-international normalized ratio), ascites, or hepatic encephalopathy. In other embodiments, the DSI equation has one or more additional terms representing a liver metabolic test result, where the test is selected from caffeine elimination, antipyrine clearance, galactose elimination capacity, and formation of MEGX from lidocaine.

In some embodiments, the DSI can be used for defining disease severity in patients with chronic liver disease, tracking disease progression and response to treatments; wherein the chronic liver disease is selected from chronic hepatitis C, primary sclerosing cholangitis (PSC), nonalcoholic fatty liver disease (NAFLD), chronic hepatitis B, alcoholic liver disease, autoimmune liver disease, cryptogenic cirrhosis, hemochromatosis, Wilson's disease, alpha-1-antitrypsin deficiency, and cholestatic liver diseases.

In some embodiments, DSI is used in a method for prediction of future clinical outcomes. In some embodiments, the clinical outcomes are selected from Child-Turcotte-Pugh (CTP) increase, varices, encephalopathy, ascites, and liver related death. At the optimum cutoffs, DSI surprisingly outperformed other standard test methods for prediction of future clinical outcomes, as shown in Example 9. Specifically, Example 9 provides evidence that DSI exhibited the highest sensitivity, specificity, positive predictive value (PPV), and negative predictive value (NPV) when compared to liver biopsy, platelet count and MELD.

In some embodiments, a DSI can be used for assessment of liver function for a number of specific clinical applications, for example, for prediction of response to an antiviral treatment in a patient with CHC, selection of patients with chronic hepatitis B who should receive antiviral therapy; assessing the risk of hepatic decompensation in patients with hepatocellular carcinoma (HCC) being evaluated for hepatic resection; identifying a subgroup of patients on waiting list with low MELD (Model for End-stage Liver Disease score) who are at-risk for dying while waiting for an organ donor; as an endpoint in clinical trials; replacing liver biopsy in pediatric populations; tracking of allograft function; measuring return of function in living donors; and measuring functional impairment in cholestatic liver disease (PSC, Primary Sclerosing Cholangitis).

In a specific embodiment, a DSI is used to predict the response to treatment, e.g., % of patients with CHC who will achieve SVR following treatment with PEG/RBV. In this specific embodiment, the DSI equation is DSI=9.84 (SHUNT)−12.36 LOGe (portal HFR)+50.5 where SHUNT is SHUNT test value in the patient and portal HFR is portal HFR test value in the patient. Applying the DSI equation to the group of patients gave a cut-off of 30, with no one above this cutoff able to achieve SVR. Of the patients with DSI of 25-30 there were 15% that achieved SVR. Of the patients with DSI of 20-25 there were 16% that achieved SVR. Of the patients with DSI of less than 20 there were 19% that achieved SVR. See Table 11.

Distinguishable Compound. In some embodiments, portal flow can be assessed utilizing any safely orally administered distinguishable compound with the following characteristics: 100% absorption following oral administration, high hepatic extraction (>70% in first pass through the liver of a healthy subject), and removal from the blood or plasma exclusively by the liver. The distinguishable compound for measurement of portal flow can be an endogenous compound or a xenobiotic.

In some embodiments, the distinguishable compound can be any labeled endogenous bile acid or bile acid conjugate; for example, the distinguishable compound can be a distinguishable cholate compound selected from any of the following labeled compounds: cholic acid, any glycine conjugate of cholic acid, any taurine conjugate of cholic acid; chenodeoxycholic acid, any glycine conjugate of chenodeoxycholic acid, any taurine conjugate of chenodeoxycholic acid; deoxycholic acid, any glycine conjugate of deoxycholic acid, any taurine conjugate of deoxycholic acid; or lithocholic acid, or any glycine conjugate or taurine conjugate thereof. In various aspects, any bile acid or bile acid conjugate may be in the form of a physiologically acceptable salt, e.g., the sodium salt of cholic acid. In one aspect, the term cholic acid refers to the sodium salt of cholic acid. Cholic acid (cholate) is the distinguishable cholate compound in some preferred embodiments. As used herein, the terms cholate compound, cholate and cholic acid are used interchangeably.

Xenobiotics that could be administered orally and also have high first pass hepatic elimination could include, but are not limited to, propanolol, nitroglycerin or derivative of nitroglycerin, or galactose and related compounds.

In some embodiments, the distinguishable compound is propranolol. Propranolol is a nonselective β blocker and has been shown to be effective for the prevention of variceal bleeding and rebleeding and is widely used as the pharmacotherapy for the treatment of portal hypertension in patients with cirrhosis. (Suk et al. 2007, Effect of propranolol on portal pressure and systemic hemodynamics in patients with liver cirrhosis and portal hypertension: a prospective study. Gut and Liver 1 (2): 159-164). Propranolol is almost entirely cleared by the liver. It has been demonstrated that total (+)-propranolol plasma clearance constitutes a good estimate of hepatic blood flow in patients with normal liver function. (Weiss et al., 1978 (+)-Propranolol clearance, an estimation of hepatic blood flow in man, Br. J. Clin. Pharmacol. 5: 457-460).

In other embodiments, the distinguishable compound is isosorbide 5-mononitrate. This compound can be administered orally and detected in plasma by HPLC-EIMS. (Sun et al., High performance liquid chromatography-electrospray ionization mass spectrometric determination of isosorbide 5-mononitrate in human plasma, J. Chromatogr. B Analyt. Technol. Biomed. Sci. 2007 Feb. 1; 846(1-2):323-8).

In some embodiments, the distinguishable compound is galactose. Galactose elimination capacity (GEC) has been used as an index of residual hepatic function. Galactose in the GEC test typically is administered intravenously at a dose of 0.5 mg/kg and venous samples taken every 5 min between 20 and 60 minutes. The clearance of galactose is decreased in individuals with chronic liver disease and cirrhosis. The fact that this carbohydrate has a high extraction ratio, however, makes the metabolism of galactose dependent on liver blood flow and hepatic functional mass. (Tygstrup N, Determination of the hepatic elimination capacity (Lm) of galactose by a single injection, Scand J Lab Clin invest, 18 Suppl 92, 1966, 118-126). The carbohydrate galactose is metabolized almost exclusively in the liver, and the elimination rate at blood concentrations high enough to yield near-saturated enzymatic conversion, the GEC is used as a quantitative measure of the metabolic capacity of the liver. One study has shown that among patients with a newly-diagnosed cirrhosis and a decreased GEC, the GEC was a strong predictor of mortality. (Jepsen et al, 2009, The galactose elimination capacity and mortality in 781 Danish patients with newly-diagnosed liver cirrhosis: a cohort study. BMC Gastroenterol. 2009, 9:50).

In certain embodiments, one or more differentiable isotopes are incorporated into the selected distinguishable compound in order to be utilized to assess hepatic function. The differentiable isotope can be either a radioactive or a stable isotope incorporated into the test compound. Stable ($^{13}C$, $^2H$, $^{15}N$, $^{18}O$) or radioactive isotopes ($^{14}C$, $^3H$, Tc-99m) can be used. Advantages of stable isotopes are the lack of exposure to radioactivity, natural abundance, and the specificity of the analyses used for test compound identification (mass determination by mass spectrometry). Stable isotopically labeled compounds are commercially available. For example, $^{13}C$- and $^2H$-labeled cholic acid compounds can be purchased from Sigma-Aldrich, CDN Isotopes and Cambridge Isotope Laboratories, Inc.

In some embodiments, the distinguishable compound for oral administration can be any distinguishable cholate compound that is distinguishable analytically from an endogenous cholic acid. In one aspect, the distinguishable cholate compound is selected from any isotopically labeled cholic acid compound known in the art. Distinguishable cholate compounds used in any one of these assays might be labeled with either stable ($^{13}C$, $^2H$, $^{18}O$) or radioactive ($^{14}C$, $^3H$) isotopes. Distinguishable cholate compounds can be purchased (for example CDN Isotopes Inc., Quebec, CA). In a preferred aspect, the distinguishable cholate is selected from any known safe, non-radioactive stable isotope of cholic acid. In one specific aspect, the distinguishable cholate compound is 2,2,4,4-$^2H$ cholic acid. In another specific aspect, the distinguishable cholate compound is 24-$^{13}C$ cholic acid.

In other embodiments, the distinguishable compound may be an unlabeled endogenous compound, such as unlabeled cholate. In the aspect using an unlabeled endogenous compound, the oral test dose is sufficiently great, for example 2.5-7.5 mg/kg cholate, for the resulting serum concentration to be distinguishable above the baseline serum concentration of that endogenous compound.

The platform for detecting and measuring the distinguishable compound in the blood sample from the subject is dependent on the type of administered distinguishable compound. For stable isotopes, the concentration of the distinguishable compound in a blood sample can be measured by, e.g. gas chromatography/mass spectroscopy (GC/MS) or liquid chromatography/mass spectroscopy (LC/MS). For radiolabeled test compounds, e.g., scintillation spectroscopy can be employed. For analysis of unlabeled compounds, e.g., autoanalyzers, luminescence, or ELISA can be employed. It is further contemplated that strip tests with a color developer sensitive directly or indirectly to the presence and quantity of test compound can be employed for use in a home test or a point of care test.

Portal Blood Flow

Portal blood flow has been found to be the key to liver assessment. The liver receives ~75% of its blood through the portal vein which brings in the nutrients for processing and deleterious compounds for detoxification. This low blood pressure system is sensitive to the earliest disruption of the microvasculature so that the early stages of CLD can be detected by decreased portal flow and increased shunting before any other physiological impacts. The high pressure hepatic systemic blood flow is decreased less and only later in the disease process. Unlike biopsy which samples only $1/50,000^{th}$ of the liver, the portal flow is a measure of the entire organ. As disease progresses there is increasing disruption of the microvasculature architecture and increasing impairment of portal flow which causes the major manifestations of advanced CLD. Impaired flow causes ascites, portal hypertension, and esophageal varices. Impaired flow causes increased shunting of toxins which leads to hepatic encephalopathy.

Cholate is a unique probe of the portal blood flow and the hepatic systemic flow. Many liver tests have attempted to use the clearance of oral or IV compounds but only cholate has succeeded in assessing early and late stage CLD. Other oral compounds are absorbed at various sites along the GI tract and do not target the portal circulation. Other compounds are taken up by nonspecific transporters. Oral cholate is specifically absorbed by the terminal ileum epithelial cells via the high affinity ileal $Na^+$-dependent bile salt transporter (ISBT) and is effluxed by MRP3 transporters directly into the portal blood flow (Trauner and Boyer, 2003, Bile salt transporters: Molecular characterization, function, and regulation. Physiol Rev. 83: 633-671). A different set of high affinity transporters including the $Na^+$/taurocholate cotransporter (NTCP) and organic anion transporting proteins (OATPs) then takes it up into hepatocytes with highly efficient first pass extraction (Trauner and Boyer, 2003, infra) so that any cholate that escapes extraction is a direct measure of the portal flow. Once intracellular, it is rapidly conjugated to glycine and taurine so that the unconjugated form does not then re-appear in the intrahepatic circulation, which would confuse the pharmacokinetics. Other unconjugated bile salts such as deoxycholate and chenodeoxycholate would behave similarly but they are much stronger solubilizing agents and would not be as safe to administer. Patient safety is ensured by using a stable isotope labeled endogenous compound avoiding the risks of xenobiotic or radiation exposure. All the proteins and systems involved are highly conserved and essential so that the pharmacokinetics of cholate are consistent between individuals and not affected by gender, age, or genetic makeup, or by diet or concomitant medications.

The portal blood flow can be non-invasively and accurately quantified by exploiting the unique physiology of the endogenous bile acid, cholate, which can be labeled, for example, with safe non-radioactive stable isotopes. Highly conserved enteric transporters (ISBT, MRP3) specifically target oral cholate to the portal circulation. Highly conserved hepatic transporters (NTCP, OATPs) clear cholate from the portal and systemic circulation. Therefore, noninvasive quantitative assessment of the portal circulation can be performed by administration to a patient of a distinguishable cholate compound and assessment of a level of the distinguishable cholate compound in blood samples drawn at various multiple time points to determine an oral clearance curve. The FLOW (portal HFR) test accurately measures the portal blood flow from a minimum of 5 blood samples taken over a period of 90 minutes after an oral dose of deuterated-cholate.

A major study of almost 300 CHC patients, portal flow measured by cholate testing was superior in predicting clinical outcomes to the current gold standard of fibrosis measured by biopsy (Everson et al, 2011). In the Early CHC study impairment of the portal flow and increased shunting measured by cholate testing was the earliest detectable pathophysiology. These results have led to a new understanding of CLD that it is the disruption of hepatic microvasculature and not fibrosis per se that is deleterious. This microvasculature disruption impairs the portal blood flow which can be non-invasively and accurately quantified by exploiting the unique physiology of the endogenous bile acid, cholate.

Portal-Systemic Shunting

As shown in FIG. 1, oral cholate is taken up by specific enteric transporters directly into the portal vein and removed by hepatic transporters in its first-pass through the liver. IV cholate distributes systemically and is extracted by both the hepatic artery and portal vein. In typical embodiments, concentrations of both oral and IV cholates are measured at 5 different times within 90 minutes of administration and clearances are calculated. The IV clearance over the oral clearance is the portal-systemic SHUNT fraction. The oral clearance per kilogram of body weight represents the Portal Hepatic Filtration Rate (Portal HFR, FLOW), or amount of portal blood delivery. STAT is the concentration of oral cholate at 60 minutes, and was shown to accurately estimate the portal HFR.

The SHUNT test non-invasively and accurately measures the portal blood flow following oral administration of a distinguishable cholate compound and also measures the systemic hepatic blood flow following intravenous co-administration of a second distinguishable cholate compound. Therefore the SHUNT test can be used to determine the amount of portal-systemic shunting. In some embodiments, an IV dose of $^{13}C$-cholate is administered concurrently with an oral dose of deuterated-cholate and a minimum of 5 blood samples taken over a period of 90 minutes after administration.

The dual cholate clearance SHUNT method yields 3 test results: Portal-systemic shunt fraction (SHUNT (%)); Portal Hepatic Filtration Rate (Portal HFR, which is also defined as FLOW in above discussions and examples, (mL/min/kg)) based on orally administered distinguishable cholate compound in the blood; and Systemic Hepatic Filtration rate (Systemic HFR, (mL/min/kg)), based on intravenously administered distinguishable cholate compound in the blood. Cholate-2,2,4,4-$d_4$ (40 mg) is given orally and taken up into the portal vein by specific enteric transporters. Cholate-24-$^{23}C$ (20 mg) is given IV and is taken up primarily through the hepatic artery from the systemic circulation. Specific hepatic transporters clear cholate from the portal and systemic circulation. For example, highly conserved hepatic transporters (NTCP, OATPs) clear cholate from the portal and systemic circulation.

Estimation of Portal Hepatic Filtration Rate

The STAT test is a simplified, non-invasive convenient test intended for screening purposes can reasonably estimate the portal blood flow from a single blood sample taken at a single time point, e.g., 60 minutes after oral administration of a distinguishable cholate compound, e.g., a deuterated cholate.

Comparison of portal HFR (FLOW), SHUNT and STAT tests.

A comparison of typical embodiments of SHUNT, FLOW and STAT tests is shown in Table 1 below.

TABLE 1

Liver Function Tests.

| Test Name | Test Compound | Route of Administration | Samples | What is Measured or Defined |
|---|---|---|---|---|
| SHUNT | $^{13}C$-cholate 4 D-$^2$H-cholate | Intravenous Oral | n = 5 over 90 min | Clearances and Shunt-comprehensive |

TABLE 1-continued

Liver Function Tests.

| Test Name | Test Compound | Route of Administration | Samples | What is Measured or Defined |
|---|---|---|---|---|
| FLOW | 4 D-$^2$H-cholate | Oral | n = 5 over 90 min | assessment of hepatic blood flow and hepatic function Portal circulation (portal hepatic filtration rate; Portal HFR) |
| STAT | 4 D-$^2$H-cholate | Oral | n = 1 at 60 min | Estimates FLOW and correlates with SHUNT |

Values for normal liver function were established in healthy controls in previous studies: the average SHUNT is 20%, average HFR (FLOW) is 30, and average STAT is 0.4.

In the diseased liver, as more blood escapes extraction by intra- and extra-hepatic shunting to the systemic circulation, the SHUNT increases (~30-90%), HFR (FLOW) or portal flow decreases (~20 to 2 mL/min/kg), and STAT increases (0.6 to 5 uM).

Definitions and Acronyms

As used herein, "a" or "an" may mean one or more than one of an item.

The term "about" when referring to any numerical parameter means +/−10% of the numerical value. For example, the phrase "about 60 minutes" refers to 60 minutes +/−6 minutes.

As used herein "clearance" may mean the removing of a substance from one place to another.

As used herein the terms, "patient", "subject" or "subjects" include but are not limited to humans, the term may also encompass other mammals, or domestic or exotic animals, for example, dogs, cats, ferrets, rabbits, pigs, horses, cattle, birds, or reptiles.

The acronym "HALT-C" refers to the Hepatitis C Antiviral Long-term Treatment against Cirrhosis trial. The HALT-C trial was a large, prospective, randomized, controlled trial of long-term low dose peg interferon therapy in patients with advanced hepatitis C who had not had a sustained virologic response to a previous course of interferon-based therapy. An NIH-sponsored Hepatitis C Antiviral Long-Term Treatment against Cirrhosis (HALT-C) Trial examined whether long-term use of antiviral therapy (maintenance treatment) would slow the progression of liver disease. In noncirrhotic patients who exhibited significant fibrosis, effective maintenance therapy was expected to slow or stop histological progression to cirrhosis as assessed by serial liver biopsies. However, tracking disease progression with biopsy carries risk of complication, possibly death. In addition, sampling error and variation of pathologic interpretation of liver biopsy limits the accuracy of histologic assessment and endpoints. The histologic endpoint is less reliable because advanced fibrosis already exists and changes in fibrosis related to treatment or disease progression cannot be detected. Thus, standard endpoints for effective response to maintenance therapy in cirrhotic patients are prevention of clinical decompensation (ascites, variceal hemorrhage, and encephalopathy) and stabilization of liver function as measured clinically by Childs-Turcotte-Pugh (CTP) score. However, clinical endpoints and CTP score were known to be insensitive parameters of disease progression. Dual isotope techniques employing distinguishable cholates were used in development of the SHUNT test and used in conjunction with the HALT-C trial.

The term "SHUNT test" refers to a previously disclosed QLFT (quantitative liver function test) used as a comprehensive assessment of hepatic blood flow and liver function. The SHUNT test is used to determine plasma clearance of orally and intravenously administered cholic acid in subjects with and without chronic liver disease. In the SHUNT test, at least 5 blood samples are analyzed which have been drawn from a patient at intervals over a period of at least about 90 minutes after oral and intravenous administration of differentiable cholates. Analysis of samples for stable isotopically labeled cholates is performed by, e.g., GC-MS, following sample derivitization, or LC-MS, without sample derivitization. The ratio of the AUCs of orally to intravenously administered cholic acid, corrected for administered doses, defines cholate shunt. The cholate shunt can be calculated using the formula: $AUC_{oral}/AUC_{iv} \times Dose_{iv}/Dose_{oral} \times 100\%$, wherein $AUC_{oral}$ is the area under the curve of the serum concentrations of the orally administered cholic acid and $AUG_{iv}$ is the area under the curve of the intravenously administered cholic acid. The SHUNT test is disclosed in Everson et al., US2008/0279766, Methods for Diagnosis and Intervention of Hepatic Disorders, filed Jan. 26, 2006, which is incorporated herein by reference. These studies demonstrated reduced clearance of cholate in patients who had either hepatocellular damage or portosystemic shunting. The "SHUNT test value" refers to a number (in %).

The SHUNT test allows measurement of first-pass hepatic elimination of bile acids from the portal circulation. Flow-dependent, first pass elimination of bile acids by the liver ranges from 60% for unconjugated dihydroxy, bile acids to 95% for glycine-conjugated cholate. Free cholate, used herein has a reported first-pass elimination of approximately 80% which agrees closely with previously observed first pass elimination in healthy controls of about 83%. After uptake by the liver, cholic acid is efficiently conjugated to either glycine or taurine and secreted into bile. Physicochemically cholic acid is easily separated from other bile acids and bile acid or cholic acid conjugates, using chromatographic methods.

The acronym "IV" or "iv" refers to intravenous.

The term "sustained virologic response" (SVR) is used to describe a desired response in a patient when hepatitis C virus is undetectable in the blood six months after finishing treatment. Conventional treatment using interferon and ribavirin doesn't necessarily eliminate, or clear, the hepatitis C virus. A sustained virologic response is associated with a very low incidence of relapse. SVR is used to evaluate new medicines and compare them with proven therapies.

The acronym "PO" refers to per oral.

The acronym "PHM" refers to perfused hepatic mass.

The acronym "SF" refers to shunt fraction, for example, as in cholate SF.

The acronym "ROC" refers to receiver operating characteristic. The ROC curve is a graphical plot which illustrates performance of a binary classifier system as its discrimination threshold is varied. It is created by plotting the fraction of true positives out of the positives (TPR=true positive rate) vs. the fraction of false positives out of the negatives (FPR=false positive rate), at various threshold settings. Sensitivity is the probability of a positive test result, or of a value above a threshold, among those with disease. Sensitivity is defined as the true positive rate (TPR): TPR=TP/P=TP/(TP+FN). False positive rate (FPR) is FPR=FP/N=FP/

(FP+FN). Accuracy (ACC) is defined as ACC=(TP+TN)/(P+N). Specificity is the probability of a negative test result, or a value below a threshold, among those without disease. Specificity (SPC), or true negative rate (TN) is defined as SPC=TN/N=TN/(FP+TN)=1−FPR. Positive prediction value (PPV) is defined as: PPV=TP/(TP+FP). Negative predictive value (NPV) is defined as NPV=TN/(TN+FN). The c-statistic is the area under the ROC curve, or "AUROC" (area under receiver operating characteristic curve) and ranges from 0.5 (no discrimination) to a theoretical maximum of 1 (perfect discrimination).

The term "oral cholate clearance" ($Cl_{oral}$) refers to clearance from the body of a subject of an orally administered cholate compound as measured by a blood or serum sample from the subject. Oral cholate clearance is used as a measure of portal blood flow. Orally administered cholic acid is absorbed across the epithelial lining cells of the small intestine, bound to albumin in the portal blood, and transported to the liver via the portal vein. Approximately 80% of cholic acid is extracted from the portal blood in its first pass through the liver. Cholic acid that escapes hepatic extraction exits the liver via hepatic veins that drain into the vena cava back to the heart, and is delivered to the systemic circulation. The area under the curve (AUC) of peripheral venous concentration versus time after oral administration of cholic acid quantifies the fraction of cholic acid escaping hepatic extraction and defines "oral cholate clearance".

The term "portal hepatic filtration rate", "portal HFR", "FLOW test" refers to oral cholate clearance (portal hepatic filtration rate; portal HFR) used as a measure of portal blood flow, or portal circulation, obtained from analysis of concentration of distinguishable cholate compound in at least 5 blood samples drawn from a subject over a period of, for example, about 90 minutes after oral administration of a distinguishable cholate compound, for example, a distinguishable cholate. The units of portal HFR value are typically expressed as mL/min/kg, where kg refers to kg body weight of the subject.

The term "STAT test" refers to an estimate of portal blood flow by analysis from one patient blood sample drawn at a defined period of time following oral administration of a differentiable cholate. In one aspect, the STAT test refers to analysis of a single blood sample drawn at a specific time point after oral administration of a differentiable cholate. In one specific aspect, the STAT test is a simplified convenient test intended for screening purposes that can reasonably estimate the portal blood flow (estimated flow rate) from a single blood sample taken 60 minutes after orally administered deuterated-cholate. The STAT test value is typically expressed as a concentration, for example, micromolar (uM) concentration.

The term "intravenous cholate clearance" ($Cl_{iv}$) refers to clearance of an intravenously administered cholate compound. Intravenously administered cholic acid, bound to albumin, distributes systemically and is delivered to the liver via both portal venous and hepatic arterial blood flow. The AUC of peripheral venous concentration versus time after intravenous administration of cholic acid is equivalent to 100% systemic delivery of cholic acid. The ratio of the AUCs of orally to intravenously administered cholic acid, corrected for administered doses, defines cholate shunt.

The term "Quantitative Liver Function Test" (QLFT), refers to assays that measure the liver's ability to metabolize or extract test compounds, can identify patients with impaired hepatic function at earlier stages of disease, and possibly define risk for cirrhosis, splenomegaly, and varices. One of these assays is the cholate shunt assay where the clearance of cholate is assessed by analyzing bodily fluid samples after exogenous cholate has been taken up by the body.

The term "Ishak Fibrosis Score" is used in reference to a scoring system that measures the degree of fibrosis (scarring) of the liver, which is caused by chronic necroinflammation. A score of 0 represents no fibrosis, and 6 is established fibrosis. Scores of 1 and 2 indicate mild degrees of portal fibrosis; stages 3 and 4 indicate moderate (bridging) fibrosis. A score of 5 indicates nodular formation and incomplete cirrhosis, and 6 is definite cirrhosis.

The term "Childs-Turcotte-Pugh (CTP) score" or "Child-Pugh score" refers to a classification system used to assess the prognosis of chronic liver disease as provided in Pugh et al., Transection of the oesophagus for bleeding oesophageal varices. Br J Surg 1973; 60:646-649, which is incorporated herein by reference. The CTP score includes five clinical measures of liver disease; each measure is scored 1-3, with 3 being the most severe derangement. The five scores are added to determine the CTP score. The five clinical measures include total bilirubin, serum albumin, prothrombin time international normalized ratio (PT INR), ascites, and hepatic encephalopathy. The CTP score is one scoring system used in stratifying the seriousness of end-stage liver disease. Chronic liver disease is classified into Child-Pugh class A to C, employing the added score. Child-Pugh class A refers to CTP score of 5-6. Child-Pugh class B refers to CTP score of 7-9. Child-Pugh class C refers to CTP score of 10-15. A website calculates post-operative mortality risk in patients with cirrhosis. mayoclinic.org/meld/mayomodel9.html.

The term "Model for End-Stage Liver Disease (MELD) refers to a scoring system used to assess the severity of chronic liver disease. MELD was developed to predict death within three months of surgery in patients who had undergone a transjugular intrahepatic portosystemic shunt (TIPS) procedure patients for liver transplantation. MELD is also used to determine prognosis and prioritizing for receipt of a liver transplant. The MELD uses a patient's values for serum bilirubin, serum creatinine, and international normalized ratio for prothrombin time (INR) to predict survival. The scoring system is used by the United Network for Organ Sharing (UNOS) and Eurotransplant for prioritizing allocation of liver transplants instead of the older Child-Pugh score. See UNOS (2009-01-28) "MELD/PELD calculator documentation", which is incorporated herein by reference. For example, in interpreting the MELD score in hospitalized patients, the 3 month mortality is: 71.3% mortality for a MELD score of 40 or more The term "standard sample" refers to a sample with a known concentration of an analyte used for comparative purposes when analyzing a sample containing an unknown concentration of analyte.

The term "Chronic Hepatitis C" (CHC) refers to a chronic liver disease caused by viral infection and resulting in liver inflammation, damage to the liver and cirrhosis. Hepatitis C is an infection caused by a blood-borne virus that attacks the liver and leads to inflammation. Many people infected with hepatitis C virus (HCV) do not exhibit symptoms until liver damage appears, sometimes years later, during routine medical tests.

The term "Alcoholic SteatoHepatitis" (ASH) refers to a chronic condition of inflammation of the liver which is caused by excessive drinking. Progressive inflammatory liver injury is associated with long-term heavy intake of ethanol and may progress to cirrhosis.

The term "Non-Alcoholic SteatoHepatitis" (NASH) refers to a serious chronic condition of liver inflammation, progressive from the less serious simple fatty liver condition called steatosis. Simple steatosis (alcoholic fatty liver) is an early and reversible consequence of excessive alcohol consumption. However, in certain cases the fat accumulation can be associated with inflammation and scarring in the liver. This more serious form of the disease is termed non-alcoholic steatohepatitis (NASH). NASH is associated with a much higher risk of liver fibrosis and cirrhosis than NAFLD. NAFLD may progress to NASH with fibrosis cirrhosis and hepatocellular carcinoma.

The term "Non-Alcoholic Fatty Liver Disease" (NAFLD) refers to a common chronic liver disease characterized in part by a fatty liver condition with associated risk factors of obesity, metabolic syndrome, and insulin resistance. Both NAFLD and NASH are often associated with obesity, diabetes mellitus and asymptomatic elevations of serum ALT and gamma-GT. Ultrasound monitoring can suggest the presence of a fatty infiltration of the liver; differentiation between NAFLD and NASH, typically requires a liver biopsy.

The term "Primary Sclerosing Cholangitis" (PSC) refers to a chronic liver disease caused by progressive inflammation and scarring of the bile ducts of the liver. Scarring of the bile ducts can block the flow of bile, causing cholestasis. The inflammation can lead to liver cirrhosis, liver failure and liver cancer. Chronic biliary obstruction causes portal tract fibrosis and ultimately biliary cirrhosis and liver failure. The definitive treatment is liver transplantation. Indications for transplantation include recurrent bacterial cholangitis, jaundice refractory to medical and endoscopic treatment, decompensated cirrhosis and complications of portal hypertension (PHTN). PSC progresses through chronic inflammation, fibrosis/cirrhosis, altered portal circulation, portal hypertension and portal-systemic shunting to varices-ascites and encephalopathy. Altered portal flow is an indication of clinical complications.

Other definitions are provided throughout the specification.

Computer/Processor

The detection, prognosis and/or diagnosis method employed in the STAT test can employ the use of a processor/computer system. For example, a general purpose computer system comprising a processor coupled to program memory storing computer program code to implement the method, to working memory, and to interfaces such as a conventional computer screen, keyboard, mouse, and printer, as well as other interfaces, such as a network interface, and software interfaces including a database interface find use one embodiment described herein.

The computer system accepts user input from a data input device, such as a keyboard, input data file, or network interface, or another system, such as the system interpreting, for example, the LC-MS or GC-MS data, and provides an output to an output device such as a printer, display, network interface, or data storage device. Input device, for example a network interface, receives an input comprising detection of distinguishable cholate compound measured from a processed blood or serum sample described herein and quantification of those compounds. The output device provides an output such as a display, including one or more numbers and/or a graph depicting the detection and/or quantification of the compounds.

Computer system is coupled to a data store which stores data generated by the methods described herein. This data is stored for each measurement and/or each subject; optionally a plurality of sets of each of these data types is stored corresponding to each subject. One or more computers/processors may be used, for example, as a separate machine, for example, coupled to computer system over a network, or may comprise a separate or integrated program running on computer system. Whichever method is employed these systems receive data and provide data regarding detection/diagnosis in return.

In embodiments, a method for selecting a treatment for a subject that has an abnormal level of distinguishable cholate compound in a blood or serum sample drawn at a single time point following oral administration comprises calculating an output score, using a computing device, by inputting the distinguishable cholate compound level into a function that provides a predictive relationship between cholate level and outcome, for subjects having a liver disease or disorder; and displaying the output score, using a computing device.

In embodiments, a STAT test value is obtained following oral administration of a distinguishable cholate compound to the subject, a single blood or serum sample is drawn at a specific time point following administration. In some embodiments, the STAT test value, expressed as concentration of distinguishable cholate compound in the sample is converted by using an equation into an estimated portal flow rate, or estimated portal HFR (FLOW) (expressed as mL/min/kg) in the subject. In embodiments, the equation is $y=0.9702x+0.0206$, where x is the log Hepquant FLOW and y is LOG Hepquant STAT.

In embodiments, the method further comprises determining whether the output score is greater than, or equal to, or less than a cutoff value, using a computing device; and displaying whether the subject is likely to experience a clinical outcome if the output score is greater than, or equal to, or less than a cutoff value.

In embodiments, a computing device, comprises a processing unit; and a system memory connected to the processing unit, the system memory including instructions that, when executed by the processing unit, cause the processing unit to: calculate a level of distinguishable cholate compound from a single blood sample from a subject into a function that provides a predictive relationship between distinguishable cholate level of the subject having a liver disease or dysfunction; and display the output score. In embodiments, the system memory includes instructions that when executed by the processing unit, cause the processing unit to determine whether the output score is greater than or equal to or less than a cutoff value; and displaying whether the subject is likely to experience a clinical outcome if the output score is greater than or equal to the cutoff value.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following examples are included to demonstrate preferred embodiments.

Example 1

STAT Test-Estimating Portal Flow from a Single Blood Draw

Figure 9:
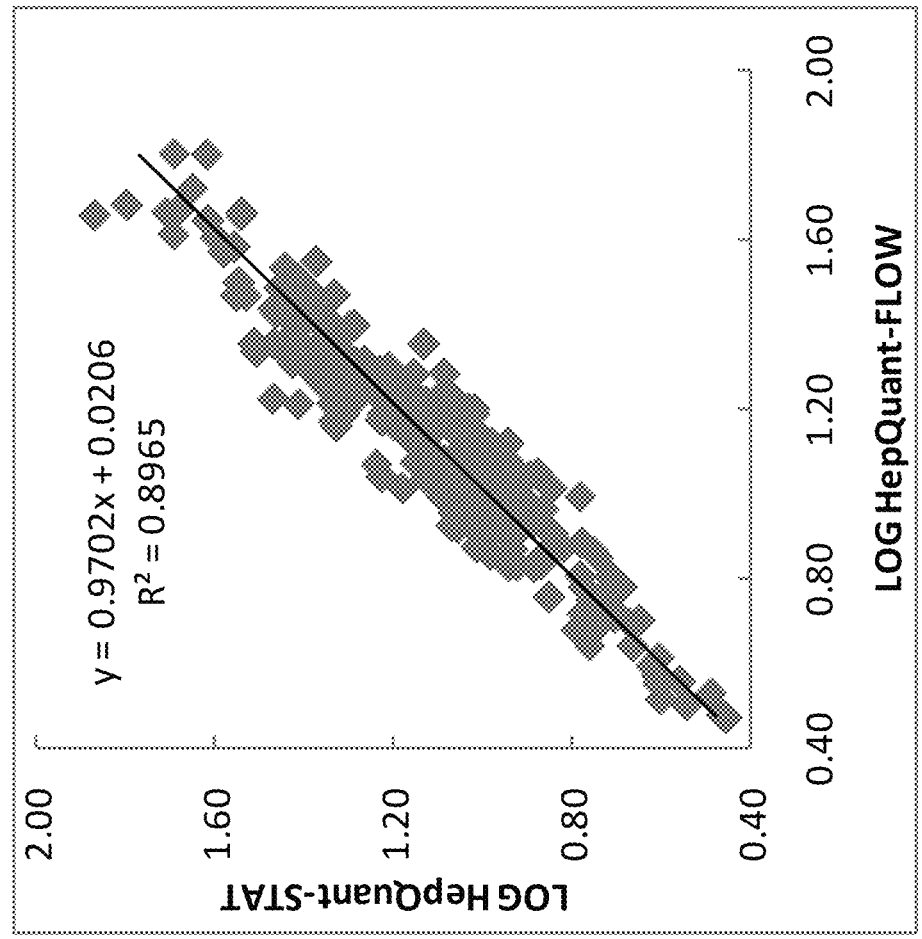
FIG. 9 shows correlation of log STAT test results at 60 min. vs. log Portal HFR (FLOW) test results for a group of CHC patients. An equation was derived that could transform the concentration (uM) at 60 min into an estimated portal flow (mL/min/kg). The equation is y=0.9702x+0.0206, where x is the LOG Portal HFR (FLOW) and y is LOG STAT.

The individual time point serum cholate concentrations from the portal HFR (FLOW) and SHUNT tests in HALT-C and Early CHC studies were carefully analyzed and differences at 45, 60, and 90 minutes were found to be highly significant (p<0.005). The concentration at 60 minutes had the best correlation ($r^2$=0.8) with the portal flow. An equation was derived that could transform the concentration (uM) at 60 min into an estimated portal flow (mL/min/kg) with 85% accuracy of the 5 point FLOW method. The equation is y=0.9702x+0.0206, where x is the LOG Portal HFR (FLOW) and y is LOG STAT. In the STAT test, the patient drinks an oral dose of distinguishable cholate compound, e.g., deuterated-cholate, and gives a single blood sample after 1 hour. The accuracy of the STAT test relative to the FLOW (Portal HFR) test is shown in FIG. 9.

Example 2

Efficacy of STAT (Estimated Portal Flow) in Detecting Hepatic Dysfunction

In the Early CHC study healthy controls had a portal flow of 34±14 ml/min/kg (mean±SD). Hepatic dysfunction was defined as a portal flow more than 1 SD below the control mean, a flow <20 ml/min/kg. In the early CHC group, about ½ the patients exhibited hepatic dysfunction. The estimated portal flows in the early CHC patients were calculated from the equation shown in FIG. 8 using their 60 min serum cholate level. The estimated flow could detect hepatic dysfunction with a sensitivity of 90%, a specificity of 85%, a positive predictive value (PPV) of 82%, and a negative predictive value (NPV) of 92%. These preliminary results demonstrate that a single blood sample after an oral cholate dose could be used to detect hepatic dysfunction in early stage CLD.

Furthermore, in the Early CHC study we analyzed the potential impact of STAT if used as a screening test. Currently adults are screened for liver disease in the primary care setting by ALT. In our analysis of the Early CHC study we found that addition of STAT to ALT could improve detection of patients with chronic hepatitis C. In early stage patients, ALT was abnormal in only 34%, STAT was abnormal in 48%, and 65% of the patients had either abnormal ALT or STAT. Screening with combination of ALT and STAT would double the detection rate for patients with liver disease due to chronic hepatitis C. Of course, when used in such a strategy, STAT would also detect patients with liver diseases other than chronic hepatitis C as well.

STAT also has test cutoffs that correlate with advanced liver disease. In patients with chronic hepatitis C and in patients with the chronic cholestatic liver disease, primary sclerosing cholangitis, STAT result with estimated FLOW of <10 mL/(kg min) correlated with risk for liver decompensation or clinical complications. In this situation, STAT would reflex to either FLOW or SHUNT to provide precise quantification of the portal circulation.

Example 3

Procedure for Performance of an Exemplary STAT Test

Supplies

PO (Per Oral) Test Compounds:
  $^2$H4-Cholate ([2,2,4,4-$^2$H]-Cholic Acid, 40 mg) (e.g. CDN Isotopes).
  Sodium bicarbonate (e.g. 600 mg).
Patient Testing Supplies:
  Serum/plasma transfer tubes and labels.
  10 cc syringe for drawing blood sample.
  7 cc red top and 7 cc gray top vacutainer tubes for serum sample collection.
  Needle discard bucket
  A drinking substance such as apple or grape juice for diluting oral test compounds.
Exemplary Test Compound Preparation
  One exemplary solution of an oral composition may contain 2,2,4,4-$^2$H -Cholate, and Sodium bicarbonate (e.g. 40 mg, and 600 mg, respectively). In one exemplary method, the day before the test, water can be added to about the 10 cc mark on a tube containing the oral test compounds to obtain the Oral Test Solution. Cap tube tightly and shake to mix. Swirl contents to get all the powder granules down into the water.
  On the test day pour dissolved Oral Test Solution into a container such as a urine cup. Rinse tube into urine cup with about 10 mls water. Prior to beginning the test, add a diluting liquid such as grape or apple juice (not citrus juice) to about the 40 ml mark on the urine cup containing the Oral Test Solution. Swirl gently to mix; do not shake or stir, or mixture may foam out of container. Have extra juice on hand for rinse.
Testing Procedure
  In one exemplary method the following procedure will be used. Optionally collect baseline serum sample (see Sample Collection) before test compound is administered.
Administration of Test Compounds.
  Start timer. Record T=0.0—have patient drink oral solution of cholate and juice. Rinse cup with a little more juice and have patient drink rinse. Record timer time.
Sample Collection
Blood
  Collect the intravenous blood sample from the patient at 60 minutes post cholate administration. Record timer time.
  Process blood samples and perform sample analysis by HPLC/MS (as outlined below for FLOW and SHUNT); or by GC/MS to determine the concentration of distinguishable cholate in the blood sample. The sample test result for a given patient at a specific date/time point can be compared to cutoff values established from, e.g., a control group, or alternatively each patient may serve as his/her own control over time.

Example 4

Procedure for Performance of SHUNT and Portal HFR (FLOW) Assays with Analysis by HPLC-MS Performance of Portal HFR (FLOW; Oral Cholate Clearance Test) and SHUNT (Cholate Shunt Test) assays are disclosed in US 2010/0055734 and US 2008/0279766, each of which is incorporated herein by reference.

Clinical Protocol. The deuterated-cholate (product# 614149) and $^{13}$C-cholate (product #605883) are purchased from Sigma-Isotec (Saint Louis, MO) and dissolved in sodium bicarbonate buffer. The inventor has held the INDs #65121 and 65123 on these compounds since 2002 and reports annually to the FDA. The $^{13}$C-cholate for injection is filtered, tested for sterility and pyrogens, and frozen in aliquots by a research pharmacist. After an overnight fast, each subject receives an indwelling intravenous catheter and a baseline venous blood sample is drawn. The subject drank the deuterated-cholate dose mixed with grape juice, and at the same time, the $^{13}$C-cholate mixed with albumin is administered IV. At time points of 5, 20, 45, 60, and 90 minutes, venous blood samples are drawn. After processing to serum, samples are transferred to the Clinical Testing Laboratory.

Laboratory Analyses. Patient serum samples are spiked with unlabeled cholate as internal standard and then the cholates are isolated by SPE and ether extraction. LCMS on C8 and Selected Ion Monitoring (SIM) are used to quantify the test compounds by the isotope dilution method. All analytical runs include appropriate standard curves and QC samples. The oral clearance (FLOW test result) and IV clearance are calculated from the serum concentrations at the 5 time points. The ratio of IV to oral clearance is the SHUNT test result. The oral clearance is estimated from only the 60 minute time point and used as the STAT test result.

Detailed Procedures are Provided Below.
Collection and Processing of Samples.
Reagents and Supplies.

The following reagents and supplies are utilized in the Cholate Shunt and Cholate Clearance Test procedures. If the patient is undergoing only the oral cholate clearance test, the IV Solution and 25% Human Albumin for injection are omitted.

IV Solution—20 mg 24-$^{13}$C -Cholic Acid in 5 cc 1 mEq/ml Sodium Bicarbonate
PO test compounds 2,2,4,4-$^{2}$H (40 mg) and Sodium Bicarbonate (600 mg)
25% Human Albumin for injection (5 ml) to be added to 24-$^{13}$C -Cholic Acid solution.
IV supplies, including 250 mls NS, indwelling catheter, 3-way stopcock.
10 cc syringes for administering IV test compounds
7 cc red top tubes for sample collection
3 ml crovials for serum storage
Needle discard bucket
Apple or Grape (non-citrus) juice for oral test compounds
Timer
Centrifuge
Transfer pipets Patient Preparation.

It is ascertained that the patient has no allergic reaction to latex. It is further ascertained that the patient has had nothing to eat or drink (NPO), except water, since midnight the night before the test day. The patient height and weight are measured and recorded. The patient is fitted with an IV with a three-way stopcock and normal saline to keep open (NS TKO) is placed before the test begins.

Cholate Compound Stock Solutions.

Test Compound Preparation.

The Oral Solution is utilized for either or both of the oral cholate clearance test and/or the cholate shunt assay. The oral solution including 2,2,4,4-$^{2}$H-Cholic acid (40 mg) and Sodium Bicarbonate (600 mg) is dissolved in about 10 cc water 24 hours prior to testing by mixing vigorously. The solution is stored in either the refrigerator or at room temperature. Just prior to administration, grape or apple (non-citrus) juice is added to the mixture. The juice solution is mixed well and poured into cup for patient to drink. The cup is rinsed with extra juice which is administered to the patient.

The IV Solution is utilized for either or both of the IV cholate clearance test and/or the cholate shunt assay. A formulation of 20 mg Cholic Acid-24-$^{13}$C in 5 cc 1 mEq/ml Sodium Bicarbonate is prepared by pharmacy staff. The Test dose is 20 mg Cholic Acid-24-$^{13}$C in 10 cc diluent. If vial is frozen, it is allowed to thaw completely. Just prior to beginning the test, the Cholic Acid-24-$^{23}$C solution is mixed with albumin as follows (this method prevents loss of test compound during mixing process). Draw up all of 24-$^{23}$C-Cholic Acid solution (about 5 cc) in a 10 cc syringe. Draw up 5 cc albumin in another 10 cc syringe. Detach needle from the 24$^{23}$C -cholate syringe and attach a 3-way stopcock. Detach needle from albumin syringe and inject albumin through stopcock into 24-$^{13}$C Cholate syringe. Draw a little air into the bile acid/albumin syringe and mix solutions gently by inverting syringe several times. Expel air.

Test Compound Administration.

Collect baseline samples before test compounds are given. The time these specimens are collected should be recorded on sample collection record sheet. Administration of test compounds is performed as follows. Start timer. Record 24 hour clock time as T=0. Record time. At T=1-3 minutes administer oral compounds. Have the patient drink the oral solution and juice. Rinse cup with more juice and have patient drink rinse. Record timer time. At T=4-5 minutes-using the 3-way stopcock administer the IV push of 20 mgs $^{13}$C Cholic acid in 5 mls 25% Human Albumin. Record timer time. Return line to NS through 3-way stopcock.

Specimen Collection.

Collect all samples via the 3-way stopcock with 0.5 ml discard before each sample to prevent dilution or cross-contamination of samples. Collect 5 ml red tops at the following times. (T=timer time).

a. T=10 minutes, collect 5 minute, record timer time;
b. T=25 minutes, collect 20 minute, record timer time;
c. T=50 minutes, collect 45 minute, record timer time;
d. T=65 minutes, collect 60 minute, record timer time;
e. T=95 minutes, collect 90 minute, record timer time.

Specimen Handling.

Red top tubes are allowed to clot at room temperature for at least 30 minutes. All blood tubes are spun for 10 minutes at 3000 rpm. Serum is removed to properly labeled vials and frozen at −20° C. until samples are transported.

Preparation of Cholate Compound Stock Solutions.

Accurate determination of cholate clearances and shunt is dependent on accurate calibration standards. Concentrations of cholic acid compounds in stock solutions must be accurate and reproducible. Very accurate (error <0.5%) portions of the cholic acid powders are weighed and glass weighing funnels and washes of 1 M NaHCO$_3$ are used to ensure quantitative transfer of the powder to the flask. Volumetric flasks are used to ensure accurate volumes so that the final concentrations of the primary stock solutions are accurate. Calibrated air displacement pipettes are used to dispense accurate volumes of the primary stock solutions that are brought to full volume in volumetric flasks to prepare secondary stock solutions that are also very accurate. Secondary stock solutions are used to prepare the standard curve samples, accuracy and precision samples, recovery samples, quality control samples, selectivity samples, and stability samples as described in the appropriate SOPs.

The following reagents are required.
1 M NaHCO$_3$
0.1 M NaHCO$_3$
0.1 M NaHCO$_3$/2% BSA
Methanol, LCMS grade
Water, CLRW grade (Clinical Laboratory Reagent Water)
Cholic Acid, purity 98%
Chenodeoxycholic Acid, purity 98%
[24-$^{13}$C]-Cholic Acid, 99 atom % $^{13}$C
[2,2,4,4-$^2$H]-Cholic Acid, 98 atom % $^2$H.

All primary stock solutions are prepared at a concentration of 250 uM using Table 2 below.

TABLE 2

Cholate compound primary stock solutions.

|  | cholic acid | 13-C cholic acid | 4-D cholic acid | chenodeoxcholic acid |
|---|---|---|---|---|
| MW | 408.56 | 409.59 | 412.60 | 392.56 |
| purity | 98.0% | 99.0% | 98.0% | 98.0% |
| volume | 100 ml | 100 ml | 100 ml | 100 ml |
| conc | 250 uM | 250 uM | 250 uM | 250 uM |
| weight | 10.42 mg | 10.34 mg | 10.53 mg | 10.01 mg |

Primary stock solutions are prepared separately in 0.1 M NaHCO$_3$ and in methanol as follows. Weigh out the appropriate amount of cholic acid compound (+/−0.05 mg) in a glass weighing funnel. Transfer the powder to a 100 ml volumetric flask. Use either methanol or 0.1M NaHCO$_3$ to rinse any residual powder from the funnel into the flask. Bring to a final volume of 100 ml with methanol and mix well. Label flask with an expiration of 1 month. Store at −20° C.

The unlabeled cholic acid is prepared as a 50 uM internal standard in either MeOH or 0.1 M NaHCO$_3$ as follows. Pipette 2.0 ml of the appropriate 250 uM CA primary standard into a 10 ml volumetric flask. Bring to a total volume of 10 ml with 0.1 M NaHCO$_3$ or methanol and mix well. Label flask with an expiration of 1 year. Store at 4° C.

[24-$^{13}$C]-Cholic Acid secondary stock solutions made in methanol are shown in Table 3. Each secondary stock solution into the appropriate 15 ml glass screw top test tube. Tubes are securely capped and sealed with several layers of parafilm and stored at −20° C.

TABLE 3

[24-$^{13}$C]-Cholic acid secondary stock solutions in methanol.

| final assay concentration uM | Secondary Stocks uM | 250 uM 13C-CA (m) ul | | Methanol ml | Total ml |
|---|---|---|---|---|---|
| 0.20 | B (m) 2.0 | 80 | + | 9.92 = | 10.00 |
| 1.00 | D (m) 10.0 | 400 | + | 9.60 = | 10.00 |
| 6.00 | F (m) 60.0 | 2400 | + | 7.60 = | 10.00 |
|  |  | 2880 |  | 27.12 | 30.00 |

[2,2,4,4-$^2$H]-Cholic Acid secondary stock solutions made in methanol are shown in Table 4. Each secondary stock solution into the appropriate 15 ml glass screw top test tube. Tubes are securely capped and sealed with several layers of parafilm and stored at −20° C.

TABLE 4

[2,2,4,4-$^2$H]-Cholic acid secondary stock solutions in methanol.

| final assay concentration uM | Secondary Stocks uM | 250 uM 4 D-CA (m) ul | | Methanol ml | Total ml |
|---|---|---|---|---|---|
| 0.30 | I (m) 3.0 | 120 | + | 9.88 = | 10.00 |
| 1.00 | K (m) 10.0 | 400 | + | 9.60 = | 10.00 |
| 3.00 | L (m) 30.0 | 1200 | + | 8.80 = | 10.00 |
|  |  | 1720 |  | 28.28 | 30.00 |

[24-$^{13}$C]-Cholic Acid secondary stock solutions made in 0.1 M NaHCO$_3$ and BSA are shown in Table 5. Each secondary stock solution is transferred into the appropriate 15 ml screw top plastic tube, capped, sealed with several layers of parafilm and stored at 4° C.

TABLE 5

[24-$^{13}$C]-Cholic acid secondary stock solutions in 0.1M NaHCO$_3$ and BSA.

| final assay concentration uM | Secondary Stocks | | 250 uM 13C-CA ul | | 0.1M NaHCO3 ml | | 2% BSA ml | | Total ml |
|---|---|---|---|---|---|---|---|---|---|
| 0.10 | A | 1.0 | 40 | + | 4.96 | + | 5.00 | = | 10.00 |
| 0.20 | B | 2.0 | 80 | + | 4.92 | + | 5.00 | = | 10.00 |
| 0.60 | C | 6.0 | 240 | + | 4.76 | + | 5.00 | = | 10.00 |
| 1.00 | D | 10.0 | 400 | + | 4.60 | + | 5.00 | = | 10.00 |
| 2.00 | E | 20.0 | 800 | + | 4.20 | + | 5.00 | = | 10.00 |
| 6.00 | F | 60.0 | 2400 | + | 2.60 | + | 5.00 | = | 10.00 |
| 10.00 | G | 100.0 | 4000 | + | 1.00 | + | 5.00 | = | 10.00 |
|  |  |  | 7960 |  | 27.04 |  | 35.00 |  | 70.00 |

[2,2,4,4-$^2$H]-Cholic Acid secondary stock solutions made in 0.1 M NaHCO$_3$ and BSA are shown in Table 6. Each secondary stock solution is transferred into the appropriate 15 ml screw top plastic tube, capped, sealed with several layers of parafilm and stored at 4° C.

TABLE 6

[2,2,4,4-$^2$H]-Cholic acid secondary stock solutions in 0.1M NaHCO$_3$ and BSA.

| final assay concentration uM | Secondary Stocks | Secondary Stocks uM | 250 uM 4D-CA ul | | 0.1M NaHCO3 ml | | 2% BSA ml | | Total ml |
|---|---|---|---|---|---|---|---|---|---|
| 0.10 | H | 1.0 | 40 | + | 4.96 | + | 5.00 | = | 10.00 |
| 0.30 | I | 3.0 | 120 | + | 4.88 | + | 5.00 | = | 10.00 |
| 0.50 | J | 5.0 | 200 | + | 4.80 | + | 5.00 | = | 10.00 |
| 1.00 | K | 10.0 | 400 | + | 4.60 | + | 5.00 | = | 10.00 |
| 3.00 | L | 30.0 | 1200 | + | 3.80 | + | 5.00 | = | 10.00 |
| 5.00 | M | 50.0 | 2000 | + | 3.00 | + | 5.00 | = | 10.00 |
| | | | 3960 | | 26.04 | | 35.00 | | 60.00 |

The secondary stock solutions as prepared above are utilized in preparation of accuracy and precision samples in human serum with unlabeled cholate as an internal standard. The secondary stock solutions are used in preparation of recovery samples with addition of unlabeled cholate as an internal standard.

In order to accurately measure patient liver function with the cholate shunt assay, the two different stable isotope cholate compounds must each be accurately quantified in patient serum. In order to do this, the accuracy, precision, and recovery of each of the two standard curves must be validated over their respective ranges of concentrations.

The accuracy and precision of an assay are assessed by running multiple replica samples at the lower limit of quantification (LLOQ), low, medium, and high range of concentrations. Accuracy is the closeness of the average measured value to the actual value. Precision is the reproducibility of the measured value as indicated by the CV. The recovery is assessed by comparing the detector response of the analyte extracted from serum relative to that of pure analyte measured at low, medium, and high concentrations.

Preparation of Quality Control Samples

The FDA provides guidance as to acceptable levels of accuracy and precision of analytical methods. See, for example, Bioanalytical Method Validation, May 2001, Section VI. Application of Validated Method to Routine Drug Analysis. Once the analytical method has been validated for routine use, its accuracy and precision should be monitored regularly to ensure that the method continues to perform satisfactorily. To achieve this objective, a number of QC samples are prepared separately and should be analyzed with processed test samples at intervals based on the total number of samples. The QC samples are run in duplicate at three concentrations (one near the lower limit of quantification (LLOQ) (i.e., 3× LLOQ), one in midrange, and one close to the high end of the range) and should be incorporated in each assay run. The number of QC samples (in multiples of three) will depend on the total number of samples in the run. The results of the QC samples provide the basis of accepting or rejecting the run. At least four of every six QC samples should be within 15% of their respective nominal value. Two of the six QC samples may be outside the 15% of their respective nominal value, but not both at the same concentration.

The QC samples must cover the high, middle, and low ranges of both standard curves. The QC samples are designed to closely simulate the actual concentrations of labeled compounds found in patient serum over the time course of the testing. The [24-$^{13}$C]-CA concentration is very high at the early time point and falls exponentially to medium and low concentrations. The [2,2,4,4-$^2$H]-CA concentration is very low at the early time point, rises to its highest value in the middle time points and then falls to a medium concentration.

Supplies

The following supplies are utilized to prepare the QC samples used in the Cholate Shunt and Cholate Clearance Test procedures. If the patient samples are undergoing only the oral cholate clearance test, the [24-$^{13}$C]-CA QC samples can be omitted.

Human Serum AB (Gemini Bio-Products #100-512)
Unlabeled Cholate Internal Standard Stock Solution (IS; 50 uM Cholic Acid in 0.1M NaHCO$_3$)
[24-$^{13}$C]-Cholic Acid and [2,2,4,4-$^2$H]-Cholic Acid Secondary Stock Solutions in 0.1 M NaHCO$_3$/1% BSA:
B 2.0 uM [24-$^{13}$C]-CA
D 10.0 uM [24-$^{13}$C]-CA
F 60.0 uM [24-$^{13}$C]-CA
I 3.0 uM [2,2,4,4-$^2$H]-CA
K 10.0 uM [2,2,4,4-$^2$H]-CA
L 30.0 uM [2,2,4,4-$^2$H]-CA
10 ml volumetric flasks
P1000 air displacement pipette and 1 ml tips
New, clean cryovials Procedure for Preparation of Quality Control Samples for Cholate Clearance and Assays.

The [24-$^{13}$C]-Cholic Acid and [2,2,4,4-$^2$H]-Cholic acid QC samples are prepared as follows. For each set of QC samples, label 3 clean 10 ml volumetric flasks as "QC 1", "QC 2", and "QC 3" as shown in Table 7. Larger volumetric flasks can be used to prepare larger batches. Use ¹/₁₀ the nominal volume of the larger flasks as the amount of secondary stock solution to add as indicated below.

TABLE 7

QC samples.

| Tubes | [24-$^{13}$C]-CA | [2,2,4,4-$^2$H]-CA |
|---|---|---|
| QC1 | 1.00 ml F | 1.00 ml I |
| QC2 | 1.00 ml D | 1.00 ml L |
| QC3 | 1.00 ml B | 1.00 ml K |

Using a P1000, add 1.0 ml of the appropriate [24-$^{13}$C]-CA stock solution and 1.0 ml of the appropriate [2,2,4,4-$^2$H]-CA stock solution to the appropriate flasks as indicated in Table 6. Bring each flask to an exact total of 10.0 ml with human serum. Securely cap each flask and mix well by inversion several times. Label 8 cryovials as "QC 1", 8 as "QC 2", and 8 as "QC 3". Aliquot 1.2 ml of each QC mixture into the appropriate vials. Store the QC samples frozen at −80° C. QC samples have an expiration of 1 year.

High Pressure Liquid Chromatography-Mass Spectroscopy (HPLC-MS) Sample Preparation In order to ensure accurate liver function testing, the labeled cholate test compounds must be isolated and identified from patients' serum samples. Cholate compounds are amphipathic molecules with both hydrophobic and hydrophilic regions. Cholates are also carboxylic acids that can exist in either an uncharged free acid form (cholic acid) or a charged carboxylic acid form (cholate) depending on pH. These properties can be exploited to isolate cholate compounds from serum. The use of HPLC/MS as opposed to GC/MS, allows analysis of cholate without sample derivitization. Alternatively, GC/MS can be used for sample analysis with derivitization by any technique known in the art, for example, by the method of Everson and Martucci, US 2008/0279766, incorporated herein by reference.

Reagents, Supplies and Equipment

The following reagents are prepared and used in the HPLC-MS sample preparation.

Water, CLRW grade (Clinical Laboratory Reagent Water)
Methanol, LCMS grade
Diethyl Ether, ACS grade
Unlabeled Cholic Acid Internal Standard (IS) Primary Stock Solution (50 uM CA in 0.1 M $NaHCO_3$)
Quality Control Samples (Prepared as Described Above)
1.0 N NaOH (dissolve 20 g NaOH in 500 ml water)
0.01 N NaOH (dilute 1.0 N NaOH 1 to 100 with water)
10% Methanol (add 100 ml Methanol to a 1 L cylinder and bring to 1.0 L with water)
90% Methanol (add 900 ml Methanol to a 1 L cylinder and bring to 1.0 L with water)
0.2 N HCl (add 1.0 ml ACS grade Concentrated HCl slowly with stirring to 57.0 ml water)
Mobile Phase (10 mM Ammonium Acetate/60% Methanol)
Disposable 16×100 and 13×100 test tubes
P1000 air displacement pipette and 1 ml tips
P100 air displacement pipette and 0.2 ml tips
Repeater Pipette
Vortex Mixer
SPE cartridges (Bond Elut LRC C18 OH, 500 mg, Varian, Inc)
Vacuum Manifold
Speed-Vac
Benchtop centrifuge
Speed-Vac vented to fume hood
Bath Sonicator
Repeater Dispensers for water, methanol, 10% methanol, and 90% methanol Remove patient serum samples and a set of QC samples (2 each of QC1, 2, and 3) from the freezer and allow them to thaw to room temperature. Personal protective equipment (PPE) including lab coat, gloves, eye protection must be worn. All eluates and equipment must be disinfected. Pipettes and tips that come in contact with the sample must be discarded into hazardous waste.

Label a set of test tubes (16×100) for each patient with that patient's initials and the time point code (5 min is 1, 20 min is 2, 45 min is 3, 60 min is 4, 90 min is 5). Using a P1000 pipette, transfer 0.50 ml of patient's serum from the appropriate collection tube into the appropriate test tube.

Label a set of test tubes (16×100) for each QC sample (QC1a, QC1b, QC2a, QC2b, QC3a, QC3b). Using a P1000, transfer 0.50 ml of each QC sample into the appropriate test tube.

Label 2 test tubes (13×100) as STD1 and STD2.

To each patient sample and each QC sample and each STD sample tube, add 50 ul of the Unlabeled Cholic Acid Internal Standard (IS) Primary Stock Solution using a Repeater Pipette.

Set aside the STD tubes for later acidification and ether extraction in step 21.

To each patient sample tube and QC sample tube add 1.0 ml of 0.01 N NaOH with a Repeater pipet and vortex 30 sec.

Label a set of SPE cartridges with one for each patient serum and QC sample to be processed.

In the hood add 5 ml Methanol with a repeater dispenser to each cartridge. This step may be done on a vacuum manifold with high vacuum or by gravity. This wets the resin bed with solvent. Once the top of the liquid reaches the top of the frit add the next solution. Avoid letting the cartridges run dry.

Add 10 ml Water with the repeater dispenser to each cartridge. This equilibrates the resin bed to prepare it for binding cholate compounds. This step may be done on the vacuum manifold on high vacuum or by gravity.

To each SPE cartridge add the appropriate sample. The cholate compounds will bind to the resin bed. To each sample test tube add a 1 ml water rinse with the repeater, vortex, and add this rinse to the appropriate cartridge. Allow the sample to run by gravity for 20 minutes or longer then may use low vacuum ≤3 inches Hg to pull sample through.

After the sample has completely entered the resin bed, add 2.5 ml Water to each SPE cartridge with the repeater dispenser. This washes the column resin bed. Use low vacuum ≤3 inches Hg.

To each SPE cartridge add 2.5 ml 10% Methanol with the repeater dispenser. This further washes the column resin bed. Use low vacuum ≤3 inches Hg.

Label a set of test tubes (13×100) with one for each patient sample and each QC sample.

Place each test tube in a rack and on top place its matching SPE cartridge.

To each SPE cartridge add 2.5 ml 90% Methanol with the repeater dispenser. This elutes the cholate compounds which are collected into the test tubes.

Place the test tubes in the Speed-Vac and centrifuge under vacuum with high heat for 45 min to reduce eluate volume and to remove methanol which interferes with ether extraction.

To each tube from the Speed-Vac and to each of the STD tubes, add 0.5 ml of 0.2 N HCl with the Eppendorf Repeater Pipette and vortex 30 sec. This acidification converts the cholate compounds into their free acid form for ether extraction.

In the fume hood, to each tube add 3 ml of diethyl ether and vortex vigorously for 30 sec. This extracts the free acid form of the cholate compounds into the ether phase.

Centrifuge 5 minutes at a minimum of 5000 rpm to accelerate phase separation.

Label another set of test tubes (13×100) one for each sample.

Carefully collect the upper ether layer and transfer to the new test tubes.

Place the ether extracts in the Speed-Vac vented to the fume hood and centrifuge under vacuum without heat until samples are dry. Alternatively, samples can be dried with a gentle stream of $N_2$ gas.

Add 100 ul Mobile Phase to dried samples, vortex 30 sec and sonicate.

Transfer samples to Agilent 1.5 ml vials and cap.

HPLC/MS Parameters and System Preparation
Reagents, Supplies and Equipment

The following reagents are prepared and used in the HPLC-MS sample analysis.
  Water, Clinical Laboratory Reagent Water (CLRW)
  Methanol LCMS grade
  10 mM Ammonium Acetate water
  10 mM Ammonium Acetate methanol
  Mobile Phase: 60% 10 mM Ammonium Acetate Methanol/40% 10 mM Ammonium
  Acetate
  Water
  Volumetric flasks, appropriate sizes
  Graduated cylinder The following instruments and supplies are used in the HPLC-MS sample analysis.
  Calibrated analytical balance
  HPLC/MS instrument: Agilent 1100 series Liquid Chromatograph Mass Spectrometer equipped with a G1956A multi-mode source, automatic sampler, HP Chemstation Software or equivalent.
  Agilent Eclipse XDB C8, 2.1×100 mm 3.5 um liquid chromatograph column
  Solvent Filter Degasser
  0.22 μm nylon filters The solvents and mobile phase are each prepared, filtered with a 0.22 μm nylon filter and degassed. Solvents and mobile phase each expire 48 hours after preparation.

The LCMS system is prepared and tuned; the column is stabilized at 40° C. and conditioned by running the mobile phase for 30 min. The samples are loaded to the autosampler. The column flow rate is 0.4 ml/min of isocratic mobile phase buffer; 60% 10 mM Ammonium Acetate Methanol/40% 10 mM Ammonium Acetate Water. 5 microliters of each sample is injected by the autosampler. The MS is run in multimode electrospray (MM-ES) ionization with atmospheric pressure chemical ionization (APCI) ionization. Selected ion monitoring is performed at 407.30, 408.30 and 411.30 m/z. Peaks are integrated by the system software. Three QC samples are assayed with each analytical run. The concentration of the QC samples must fall within 15% accuracy.

Data from selective ion monitoring of either or both intravenous and oral samples are used to generate individualized oral and intravenous clearance curves for the patient. The curves are integrated along their respective valid time ranges and an area is generated for each. Comparison of intravenous and oral cholate clearance curves allows determination of first-pass hepatic elimination or portal shunt. The liver shunt fraction calculated by the formula:

$$\text{ShuntFraction} = [\text{AUC}_{oral}/\text{AUC}_{IV}] * [\text{Dose}_{IV}/\text{Dose}_{oral}] * 100\%.$$

wherein AUC represents area under the curve and Dose represents the amount (in mg) of dose administered.

Example 5

Slow, Moderate, and Rapid Progressors: Three Distinct Categories of Patients with Primary Sclerosing Cholangitis Detected by Functional Assessment Using Cholate Testing The current example examined the relationships of Portal HFR and SHUNT to patient age to estimate approximate rate of PSC disease progression. Primary Sclerosing Cholangitis (PSC) exhibits inexorable progression but the rate of progression varies between patients. Cholate Testing can measure the Portal Hepatic Filtration Rate (HFR) and portal-systemic SHUNT, which correlate with varices, ascites, decompensation, and need for transplant (Gastroenterology 2012, 142: S911; Liver Transplantation 2012, 18: S233). Surprisingly, the relationships of Portal HFR (FLOW) and SHUNT to patient age were found to be useful to estimate the approximate rate of PSC disease progression. Cholate testing was employed to distinguish slow, moderate and rapid progressors.

Methods. PSC patients (n=42) and 32 healthy controls, ranging in age from 20 to 67, underwent Cholate Testing and medical histories were recorded. Patients were subjected to two cholate testing methods. Specifically, a first distinguishable cholate was administered orally and a second distinguishable cholate was administered intravenously. The orally administered cholate, 2,2,4,4-d4 cholate (40 mg dose), was taken up directly into the portal vein by specific enteric transporters. The intravenously administered cholate, 24-$^{13}$C-cholate (20 mg), was distributed systemically and enters the liver primarily through the hepatic artery. Specific hepatic transporters clear the dual cholates from the portal and systemic circulation. Peripheral blood samples were collected at 0, 5, 20, 45, 60 and 90 minutes following administration. The distinguishable cholates in each blood sample were assayed by LCMS methods. In this case the methods had been validated according to FDA guidelines for accuracy and precision. The values obtained from each sample were used to determine portal hepatic flow rate (portal HFR, FLOW) and SHUNT by the methods of Everson, US 2010/0055734, Methods for Diagnosis and Intervention of Hepatic Disorders, filed Sep. 11, 2009; and Everson et al., US2008/0279766, Methods for Diagnosis and Intervention of Hepatic Disorders, filed Jan. 26, 2006; each of which is incorporated herein by reference. Oral cholate-2,2,4,4-d4 targets the portal circulation, and its clearance defines Portal HFR. IV cholate-24-$^{13}$C clearance measures Systemic HFR. The ratio of Systemic to Portal HFR defines SHUNT. Reproducibility of duplicate testing was excellent with CVs of 10%; the averages of duplicate tests were used for analysis.

Figure 2:
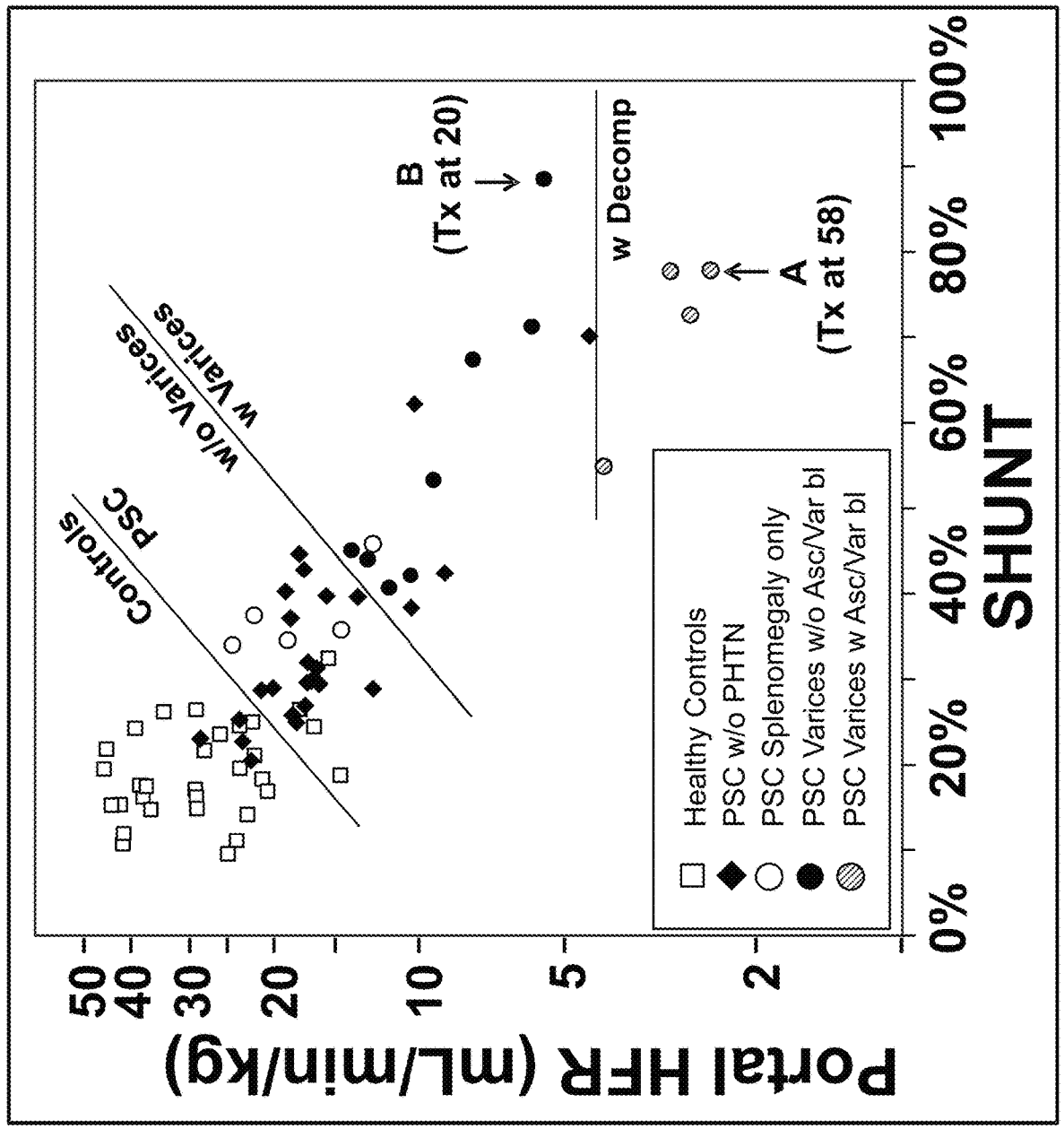
FIG. 2 shows Portal HFR vs. SHUNT test values can distinguish healthy controls from PSC patients without varices, PSC patients with varices and PSC patients with decompensation.

Results. In PSC patients Portal HFR decreased and SHUNT increased with age, compared to healthy controls. Examination of these age-related changes revealed 3 categories of PSC patients defined by drop in Portal HFR or increase in SHUNT—Slow, Moderate, and Rapid Progressors. Within each category the age-related decline in function was approximately linear. Slow Progressors (n=23, 61%) demonstrated modest age-related decline in Portal HFR or increase in SHUNT. If they developed portal hypertension (PHTN), manifestations occurred later in life—the 3 with splenomegaly were over age 45 and the 2 with varices were over age 62. Moderate Progressors (n=12, 32%) often developed portal hypertension (9 out of 12 patients) and experienced decline earlier in life—splenomegaly as early as age 30 and varices as early as age 32. Most of the Moderate Progressors over age 54 had ascites and/or variceal bleeding (4 out of 5 patients). Rapid Progressors (n=3, 8%) were relatively rare but these patients exhibited low Portal HFR and high SHUNT earlier than age 30. The patient A with the highest SHUNT in the category of Moderate Progressors received a liver transplant at age 58 while the patient B with the highest SHUNT in the category of Rapid Progressors received a liver transplant at age 20, as shown in FIGS. 2-4. FIG. 2 shows PSC patients segregated into 3 distinct groups based on their Portal HFR test values and age at the time of testing. FIG. 3 shows PSC patients segregated into 3 distinct groups based SHUNT test values and age at the time of testing. PSC Patients categorized as Slow Progressors had only modest changes in function compared to controls. PSC patients categorized as Moderate and Rapid Progressors exhibited more complications and at earlier ages.

Figure 5:
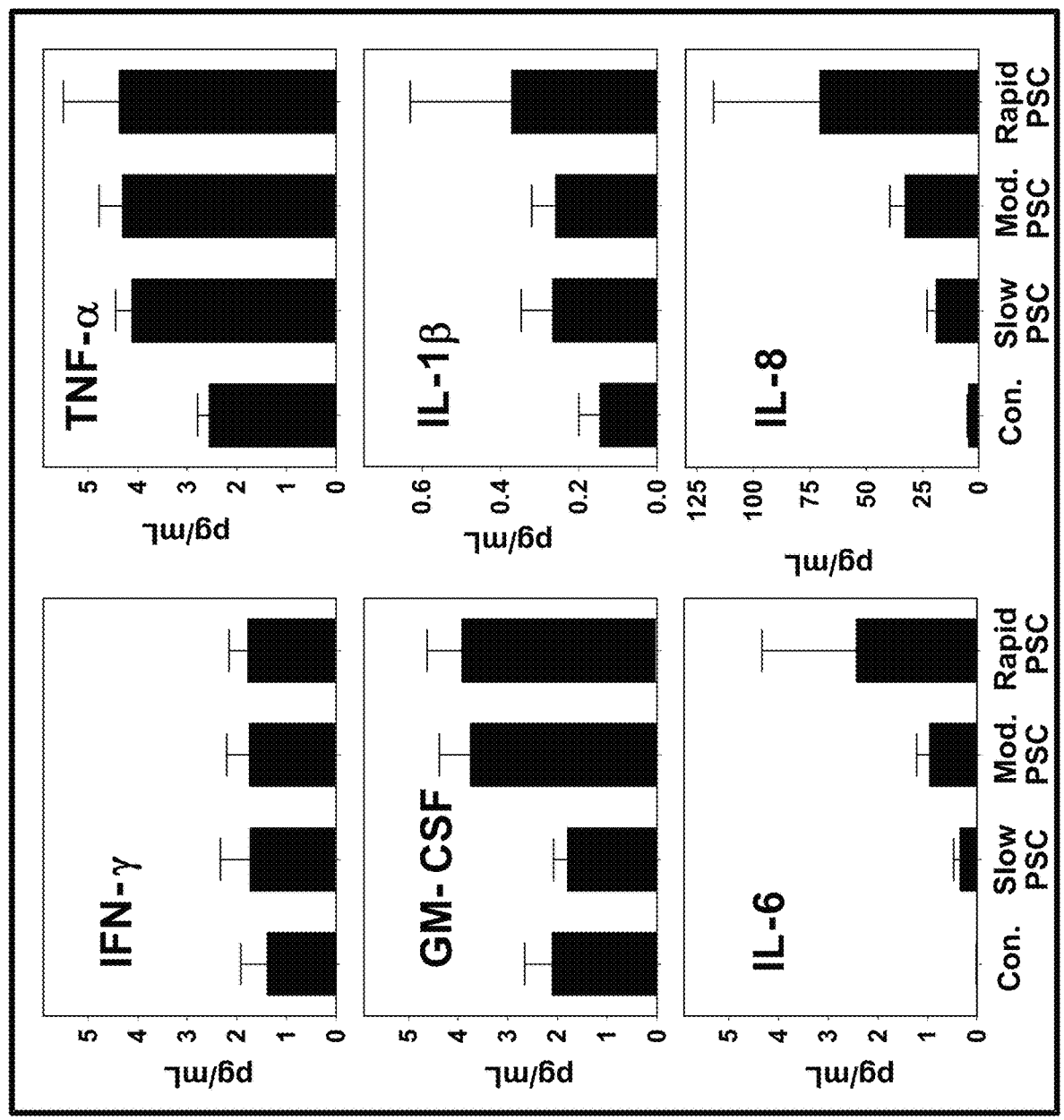
FIG. 5 shows pro-inflammatory cytokines IFN-γ, TNF-α, GM-CSF, IL-1β, IL-6 and IL-8 from healthy controls and patients with PSC categorized as Slow, Moderate and Rapid Progressors. Each category of patients exhibited a unique pattern of cytokines suggesting unique pathophysiological mechanisms.

Each category of patients exhibited a unique pattern of cytokines suggesting unique pathophysiological mechanisms, as shown in FIG. 5. IFN-γ did not change between controls and slow, moderate and rapid progressors. TNF-α was increased in each category of PSC patients compared to healthy controls. GM-CSF was increased in moderate and rapid progressors compared to controls and slow progressors. IL-1b appeared to trend higher in rapid progressors, but was not statistically significant. IL-6 was virtually undetected in healthy controls, while slow, moderate and rapid progressors exhibited a trend to escalating levels of IL-6. IL-8 was virtually undetected in healthy controls, while slow, moderate and rapid progressors exhibited a trend to escalating levels of IL-8.

Conclusions. Functional assessment by Cholate Testing identified 3 distinct categories of patients with PSC: Slow, Moderate, and Rapid Progressors. Differentiating categories of PSC patients by Cholate Testing could enhance investigation of unique pathophysiologic mechanisms of disease progression and aid development of appropriately targeted therapy.

Example 6

An Algorithm Using SHUNT and Portal HFR to Categorize PSC Patients

PSC patients are assigned to a subcategory of PSC based on their SHUNT and Portal HFR and their age at the time of testing by the following algorithm.

Figure 6:
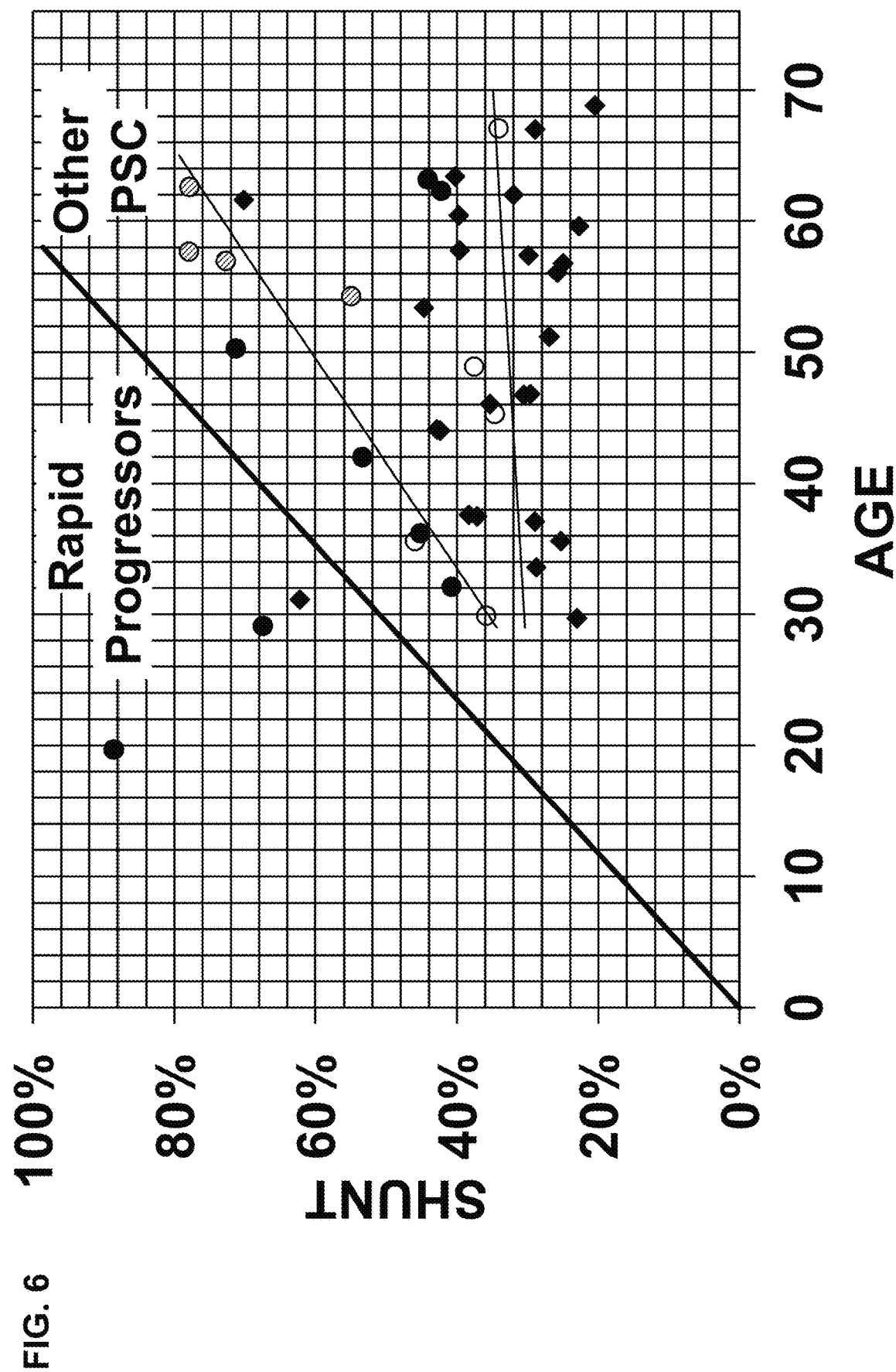
FIG. 6 shows SHUNT vs. age determines PSC patients categorized as Rapid Progressors. The line starting at 0 demarcates SHUNT/age of 1.7; patients above the line exhibiting SHUNT/age>1.7 are categorized as Rapid Progressors. Patients with SHUNT/1.7<1.7 are classified into other PSC categories.

Step 1 is based on SHUNT and age. If the patient's SHUNT (in percent) divided by their age (years) is greater than 1.7 then the patient is diagnosed as a Rapid Progressor. If this value is less than 1.7, then proceed to Step 2. FIG. 6 shows SHUNT vs Age Determines the Rapid Progressors. The line starting at age 0 demarcates a SHUNT/age of 1.7 and those above the line are Rapid Progressors and those below are other PSC categories.

Figure 7:
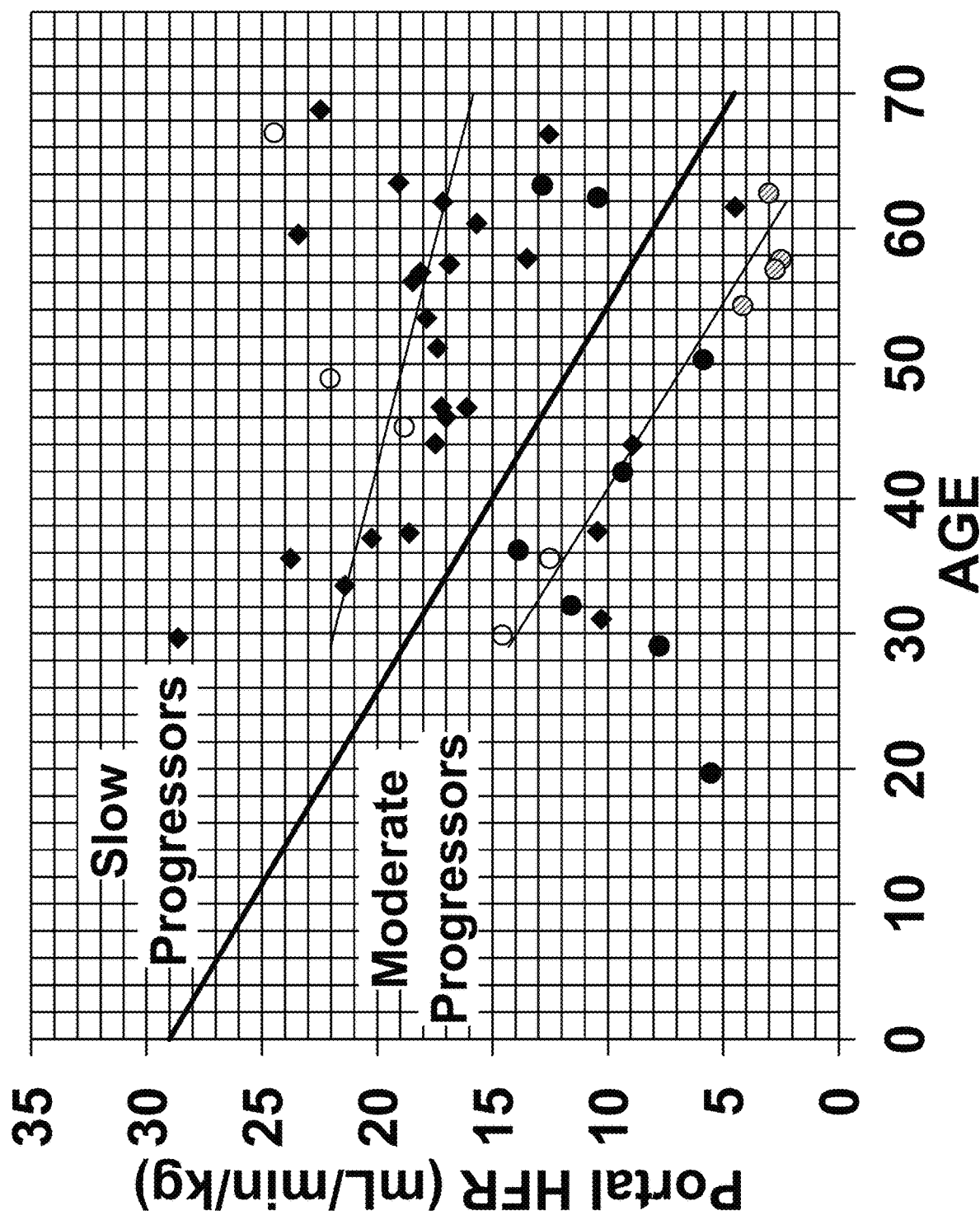
FIG. 7 shows Portal HFR vs. age for PSC patients that have not been classified as Rapid Progressors. The line starting at 0 demarcates a Portal HFR+[0.35+age] that is equal to 29. Patients with Portal HFR+[0.35+age] greater than 29 are categorized as Slow Progressors. Patients with Portal HFR+[0.35+age] less than 29 are categorized as Moderate Progressors.

Step 2 is based on Portal HFR and age. If the Portal HFR (in mL/min/kg)+[0.35×age (years)] is greater than 29 then the patient is diagnosed as a Slow Progressor. If this value is less than 29 then the patient is diagnosed as a Moderate Progressor. Those patients already diagnosed as a Rapid Progressor in Step 1 are not further evaluated in this manner by Portal HFR. FIG. 7 shows Portal HFR vs Age Determines the Slow and Moderate Progressors. The line starting at age 0 demarcates a Portal HFR+[0.35×age] that is equal to 29. Those patients above the line are the Slow Progressors and those patients below this line are the Moderate Progressors.

Example 7

A Method Using STAT to Categorize PSC Patients

Figure 8:
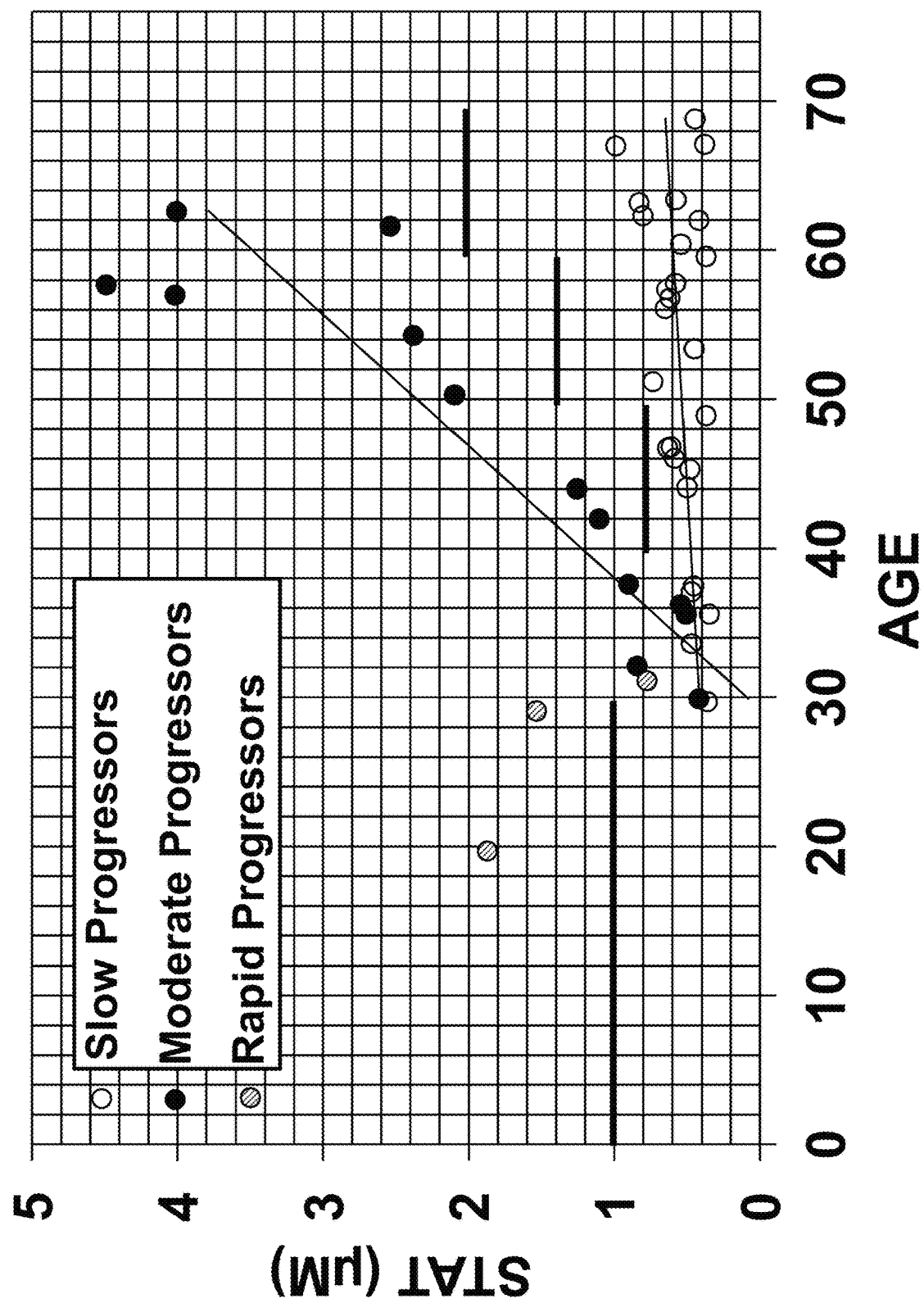
FIG. 8 shows STAT test values vs. Age for PSC patients. Most patients can be categorized using simple cut-offs, shown as dark lines on the plot of Slow, Moderate and Rapid Progressors. Patients between age 30 and 40 have overlapping STAT results and are not able to be categorized by this method.

The STAT test is a simplified screening test as described herein where the value is obtained from distinguishable cholate compound blood or serum concentration (in µM) obtained from a patient at a single time point (e.g., 60 minutes) after oral administration. The STAT test value can be used to estimate Portal blood flow. The STAT test value in PSC patients can be compared to a cut-off value to categorize PSC progression in most patients. Most PSC patients can be assigned to a subcategory of PSC based on simple STAT cutoffs and their age at the time of testing, as shown in FIG. 8. FIG. 8 shows STAT can categorize most PSC patients. Patients can be categorized using simple cutoffs shown as dark lines on this plot of Slow, Moderate, and Rapid Progressors. Patients between 30 and 40 have overlapping STAT results and are not able to be categorized by this method. If patients are less than 30 and have STAT >1 µM the patient is diagnosed as a Rapid Progressor. Patients in their 30s are not accurately categorized by STAT. For older patients, cut-off values are shown in Table 8.

TABLE 8

STAT test cut-off values for PSC Patients.

| PSC Patient Age | STAT cut-off (µM) | PSC Category |
|---|---|---|
| <30 yrs | >1 | Rapid Progressor |
| 30's | | N.A. |
| 40's | >0.8 | Moderate Progressor |
| | <0.8 | Slow Progressor |
| 50's | >1.4 | Moderate Progressor |
| | <1.4 | Slow Progressor |
| 60's | >2.0 | Moderate Progressor |
| | <2.0 | Slow Progressor |

Example 8

Development of a Disease Severity Index

Previously, the Portal HFR test or SHUNT test were each utilized separately in various cohorts of patients and normal controls to develop cut-offs for specific chronic liver diseases or conditions. As described herein, a disease severity index (DSI) is obtained from a DSI equation where the terms of the equation comprise one or more liver function test result values selected from SHUNT, Portal HFR, and/or Systemic HFR, where test result values are used as terms in a disease severity index equation to calculate a Disease Severity Index (DSI).

In one embodiment, the utility of the DSI in predicted response (sustained virologic response, SVR) of a group of CHC patients to pegylated interferon/ribavirin (PEG/RBV) treatment was investigated. The % of CHC patients that achieved SVR was calculated for groups of patients within specified ranges of DSI, as shown in Tables 9-11. A DSI equation was developed incorporating both the SHUNT and portal HFR test values. The DSI equation is shown below.

$$DSI = 9.84 \, (SHUNT) - 12.36 \, LOG_e \, (portal \, HFR) + 50.5$$

Applying the DSI equation to a group of healthy controls gave a mean score +/−SD of 10+/−3. The most functionally impaired patient, who required a transplant within 3 weeks of testing, had a score of 47. The highest score in a patient that might survive is expected to be about 50. Use of DSI compared to SHUNT or Portal HFR alone is shown in Tables 9-11, which show the % of CHC patients that achieved SVR calculated for groups of patients within specified ranges of SHUNT, Portal HFR, or DSI.

TABLE 9

SHUNT and SVR in CHC Patients.

| SHUNT | <25 | 25-35 | 35-45 | 45-60 | >60 | all |
|---|---|---|---|---|---|---|
| % SVR | 17% | 14% | 14% | 3% | 5% | 14% |
| SVR | 11 | 12 | 7 | 1 | 1 | 32 |
| N | 63 | 59 | 50 | 37 | 21 | 230 |

TABLE 10

Portal HFR and SVR in CHC Patients.

| HFR | >20 | 15-20 | 10-15 | 5-10 | <5 | all |
|---|---|---|---|---|---|---|
| % SVR | 15% | 21% | 17% | 7% | 0% | 14% |
| SVR | 5 | 11 | 12 | 4 | 0 | 32 |
| N | 34 | 52 | 70 | 59 | 15 | 230 |

TABLE 11

DSI and SVR in CHC Patients.

| DSI | 0-20 | 20-25 | 25-30 | 30-40 | 40-50 | all |
|---|---|---|---|---|---|---|
| % SVR | 19% | 16% | 15% | 0% | 0% | 14% |
| SVR | 17 | 10 | 5 | 0 | 0 | 32 |
| N | 89 | 62 | 33 | 37 | 9 | 230 |

In some embodiments, the DSI is used to predict response to an antiviral treatment, e.g., % of patients with CHC who will achieve SVR. In some embodiments, the DSI is used to predict the response to treatment, e.g., % of patients with CHC who will achieve SVR following treatment with PEG/RBV.

Example 9

Disease Severity Index to Assess Liver Related Outcomes

Nonalcoholic fatty liver disease (NAFLD) encompasses benign hepatic steatosis (fatty liver) and steatosis accompanied by inflammation, necrosis, and fibrosis (NASH) which may progress to cirrhosis and clinical complications. Although NASH is an aggressive necroinflammatory process, rates of progression of fibrosis and evolution to cirrhosis vary greatly between patient.

The slow rate of progression dictates that many years of observation and followup would be required to establish the natural history of NASH or to prove that a treatment or intervention reduces clinical outcomes. Long-term studies with the primary outcome of clinical complications are enormously costly and suffer from both patient and investigator attrition. Short-term studies using early markers or surrogates that correlate with clinical outcomes are desirable.

Until now, fibrosis stage on liver biopsy was considered the gold standard as the surrogate for clinical outcomes. Several studies have demonstrated that severity of fibrosis, but not steatosis, predicts future risk for clinical outcome.

An alternative to liver biopsy should be accurate, reproducible, well-tolerated, relatively inexpensive, and noninvasive. In addition, these alternative tests should correlate with fibrosis, independent of the degree of steatosis, and predict risk for clinical outcome. Quantitative liver function tests (QLFTs) were developed to address these needs. Nearly all QLFTs satisfy one or more criteria as alternatives to liver biopsy. Dual cholate clearance (SHUNT) satisfies all of these criteria. The NIH- and industry (Roche)-sponsored QLFT ancillary study of the Hepatitis C Antiviral Long-Term Treatment Against Cirrhosis (HALT-C) Trial evaluated the ability of QLFTs to predict clinical outcomes.

Patients (N=285) were studied with a battery of QLFTs (caffeine, antipyrine, lidocaine-MEGX, galactose, dual cholates, and SPECT liver-spleen scan) at baseline, 2 yr, and 4 yr, and followed for clinical outcomes (Child-Turcotte-Pugh (CTP) increase, varices, encephalopathy, ascites, liver related death) for up to 8.3 years (4.9±2.2 yrs, mean±SD). The likelihood of clinical outcome for those beyond the high-risk cutoff for each test was compared. Hazard ratios for baseline tests ranged from 6.5 for oral cholate to 2.2 for GEC, and pooled relative risk for serial tests ranged from 14.1 for oral cholate to 2.5 for MEGX. In additional publications and presentations, the dual cholate test was shown to not only predict clinical outcome, but also correlated with stage of fibrosis, risk for cirrhosis, risk for varices, and variceal size and tracked improvement in liver function after SVR and recovery from living liver donation.

Interestingly, in models of dual cholate predicting clinical outcome, histologic stage of fibrosis dropped from significance; therefore staging liver biopsy could surprisingly be avoided. Given the broad clinical associations, further investigation of the potential utility of dual cholate testing as an alternative to biopsy seemed warranted.

The initial development of dual cholate into a clinical test required simplification of clinical testing, revision of laboratory procedures, institution of quality controls, and validation of testing performance characteristics according to FDA guidelines for bioanalytical procedures and method.

A Data-Use Agreement with NIH and HALT-C was reached to re-examine and explore clinical relationships of the revised test. Three major parameters of liver function are defined by the test: Systemic Hepatic Filtration Rate (HFR) from clearance of intravenously administered cholate, Portal HFR from orally administered cholate, and SHUNT from the ratio of clearances. The disease severity index is a composite of all three variables. It was defined from the ability of these tests to predict risk for future clinical outcome in patients with fibrotic stages of chronic hepatitis C, as shown in Example 10.

Figure 10:
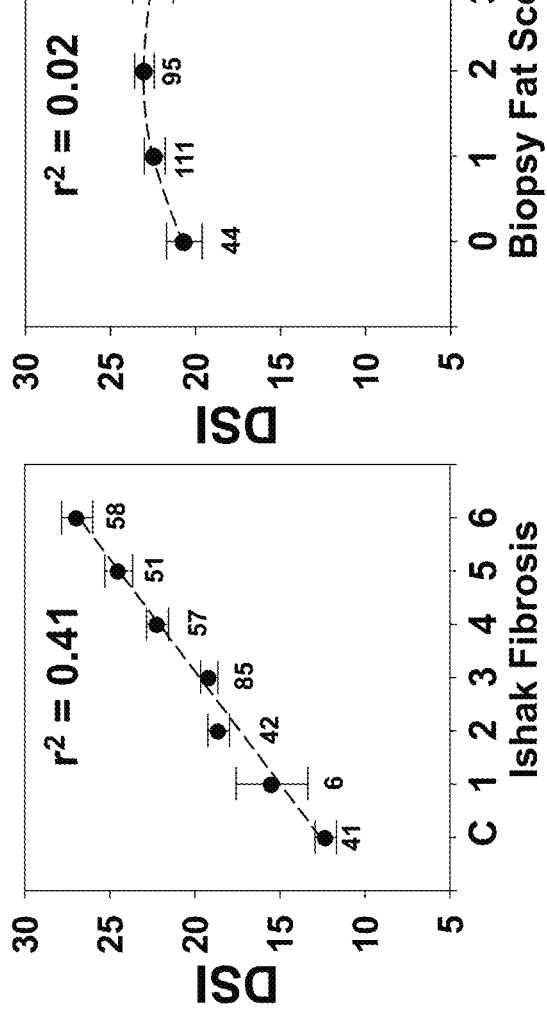
FIG. 10 shows DSI linearly correlates with Ishak fibrosis score (liver biopsy, left panel) but is not influenced by steatosis (biopsy fat score, right panel), as provided in Example 9.
Figure 11:
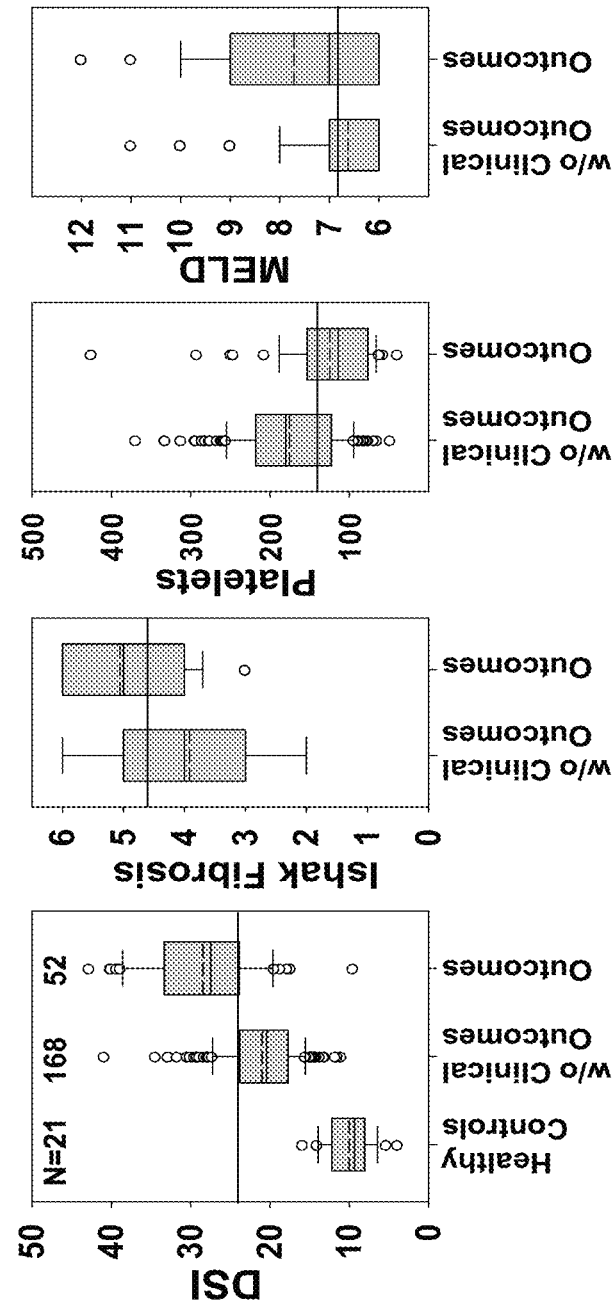
FIG. 11 shows performance of DSI in identifying the patients with future clinical outcomes as compared to that of Ishak fibrosis score (liver biopsy), platelet count (CBC), and MELD (Model for End-stage Liver Disease score). At the optimum cutoffs, DSI surprisingly outperformed other standard test methods including liver biopsy and MELD for prediction of future clinical outcomes. Specifically, DSI exhibited the highest sensitivity, specificity, PPV, and NPV when compared to liver biopsy, platelet count and MELD.

Using clinical outcome as the endpoint in HCV patients a disease severity index (DSI) was defined from the parameters of the test, as shown in Example 10. The DSI correlates with liver disease severity in HCV patients, PSC patients, and in NASH patients in a new study currently enrolling subjects. DSI is highly reproducible, correlates with fibrosis, and predicts clinical outcome. FIG. 10 demonstrates that DSI linearly correlates with fibrosis (left panel) but is not influenced by steatosis (biopsy fat score, right panel). The performance of DSI in identifying the patients with future clinical outcomes was compared to that of Ishak fibrosis score, platelet count, and MELD, (FIG. 11 and Table 12).

TABLE 12

Identifying Patients who will have Outcomes.

| Test | Parameter | C-statistic | Optimum Cut-off |
|---|---|---|---|
| Cholate | DSI | 0.83 | >23 |
| Biopsy | Ishak Fibrosis | 0.75 | >F4 |
| CBC | Platelets | 0.75 | <140 |
| Std Labs | MELD | 0.70 | >6 |

As shown in FIG. 11 and Table 12, at the optimum cutoffs DSI had the highest sensitivity, specificity, PPV, and NPV when compared to biopsy (Ishak fibrosis), CBC (platelets), or standard labs (MELD). QLFTs, particularly dual cholate, can be an accurate, reproducible, cost-effective, noninvasive alternative to liver biopsy as an endpoint in studies of natural history or for monitoring the effectiveness of treatment in NAFLD.

Example 10

Disease Severity Index Assessment of Liver Related Outcomes in Chronic Hepatitis C Cholate testing was performed at baseline in 224 chronic HCV patients (Ishak F2-F6) enrolled in the HALT-C trial, characterized by CTP scores of 5 or 6 and no prior history of clinical complications.

Specifically, archive serum was re-analyzed to determine cholate clearance curves for systemic Hepatic Filtration Rate (HFR) from clearance of intravenously administered cholate, Portal HFR from orally administered cholate, and SHUNT from the ratio of clearances using an improved LCMS method validated to FDA guidelines. Patients were followed for clinical outcomes for up to 8.3 years (4.9±2.2 years, mean±SD). Clinical outcomes (n=54) were defined as CTP progression, variceal hemorrhage, ascites, hepatic encephalopathy, or liver-related death.

Derivation of a Disease Severity Index (DSI) was performed using univariate Cox univariate Cox proportional hazard regression analysis as shown in Table 13.

TABLE 13

Univariate Cox Proportional Analysis Hazard Regression Analysis.

|  | Chi-Square |  | Chi-Square |
|---|---|---|---|
| SHUNT | 44.7 | $Log_e$ SHUNT | 34.8 |
| Portal HFR | 51.2 | $Log_e$ Portal HFR | 70.2 |
| Systemic HFR | 21.9 | $Log_e$ Systemic HFR | 29.8 |

The tests with the highest Chi-square were combined into a disease severity index to improve performance.

$$DSI = A(SHUNT) + B(\log_e \text{portal HFR}) + C(\log_e \text{systemic HFR}) + D.$$

A DSI equation was developed based on prediction of first clinical outcome in the HALT-C cohort:

$$DSI = 5.75 (SHUNT) - 7.22 (\log_e \text{Portal HFR}) - 8.45 (\log_e \text{Systemic HFR}) + 50$$

Figure 12:
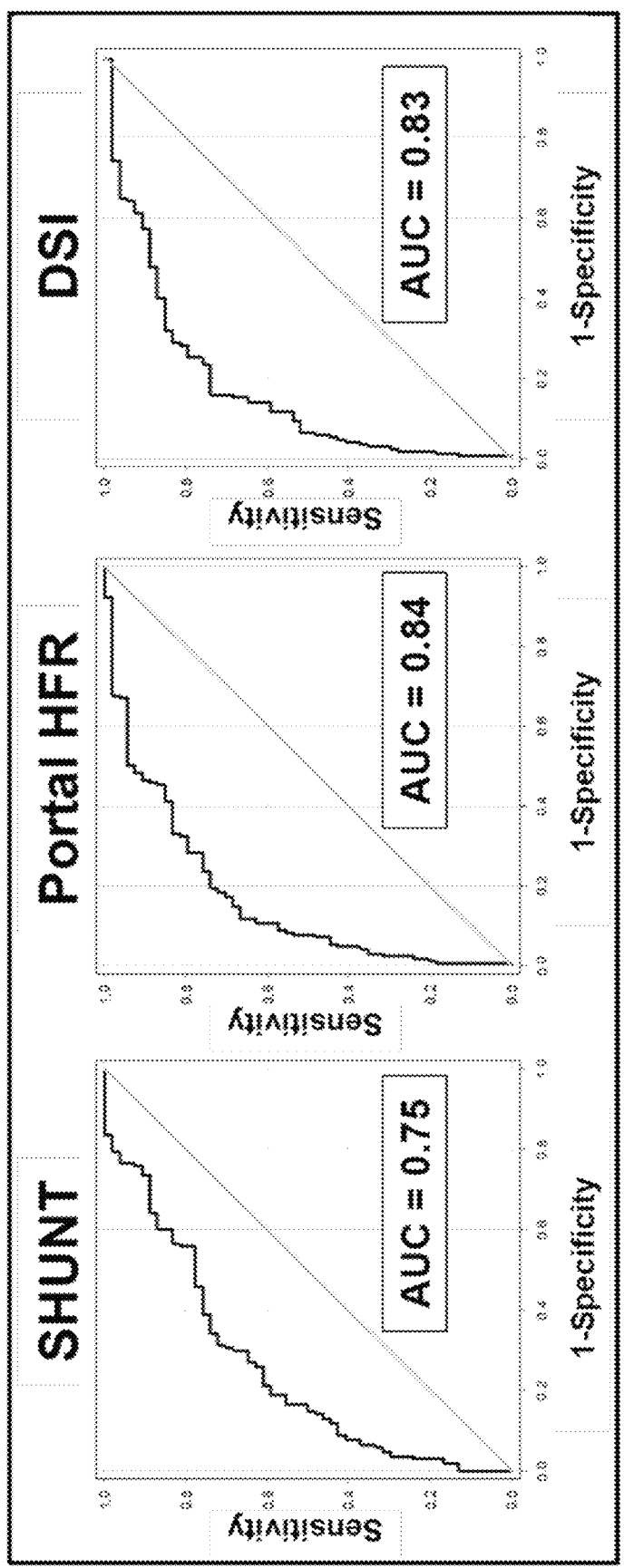
FIG. 12 shows ROC curves for predicting outcomes for SHUNT, portal HFR and DSI. Optimum cutoffs were determined as the point on each curve closest to the top-left corner.

ROC curves for predicting outcomes for SHUNT, Portal HFR and DSI were prepared and are shown in FIG. 12. Optimum cut-offs were determined as the point on each curve closest to the top-left corner as shown in FIG. 12.

Patients ranged from DSI9 (normal) to 40 (severe dysfunction). ROC curves showed that DSI could identify patients with medium/large varices, c-statistic 0.82, and could predict which patients would have clinical outcomes, c-statistic 0.83, and DSI>25 was the optimum cutoff for both. DSI>25 had a higher balanced accuracy than cirrhosis by biopsy (Ishak F5-F6) and the PPV for identifying medium/large varices increased 41% relative to biopsy and the PPV for predicting outcomes increased 47% (Table 14).

TABLE 14

Prognostic Test Performance.

| Test Cutoff | Sensitivity | Specificity | PPV | NPV | Balanced Accuracy |
|---|---|---|---|---|---|
| Biopsy (Ishak F5-F6) | 72% | 66% | 40% | 88% | 69% |
| SHUNT > 44% | 59% | 81% | 50% | 86% | 70% |
| Portal HFR < 9.7 mL/min/kg | 74% | 81% | 55% | 91% | 77% |
| DSI > 25 | 74% | 84% | 60% | 91% | 79% |

The prognostic test performance of each test system was evaluated and the highest sensitivity, specificity, PPV, NPV, and balanced accuracy were all achieved by the cholate test based DSI as shown in Table 14.

Figure 13:
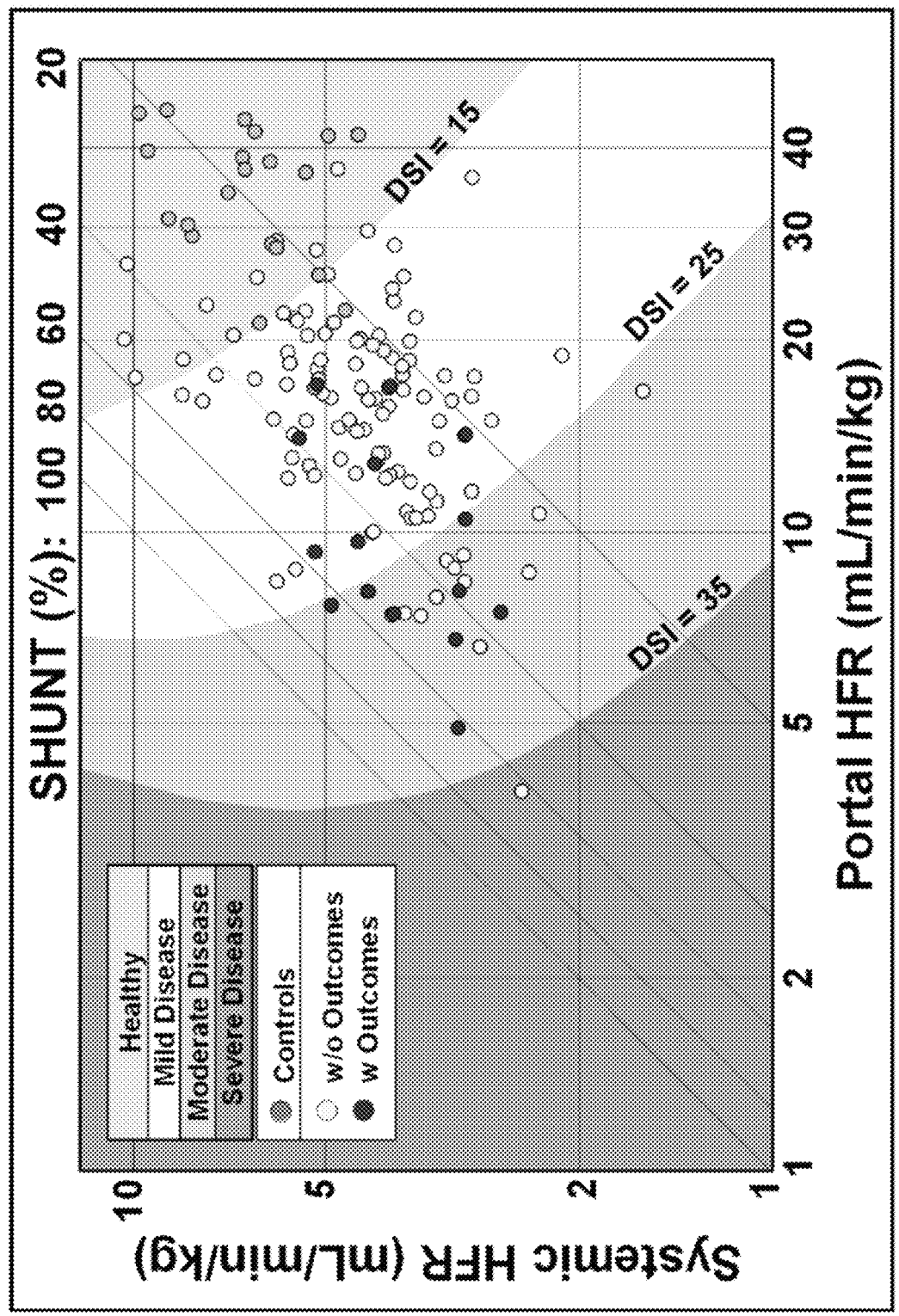
FIG. 13 shows a plot of cholate test results for non-cirrhotic chronic hepatitis C patients (Ishak F2,3,4; n=19, 63, 45) with mild disease, moderate disease and severe disease and test results of cholate based tests SHUNT (%), systemic HFR (mL/min/kg), portal HFR (mL/min/kg) and DSI. Portal HFR is plotted on the X axis and systemic HFR on the Y axis, SHUNT, the ratio of systemic to portal HFR is represented by the diagonal lines, DSI is displayed in shaded regions. Surprisingly, non-cirrhotic patients with high DSI have greater risk of outcomes as discussed in Example 10.

FIG. 13 shows a plot for non-cirrhotic patients (Ishak F2,3,4; n=19, 63, 45) with mild disease, moderate disease and severe disease test results of cholate based tests SHUNT (%), systemic HFR (mL/min/kg), portal HFR (mL/min/kg) and DSI according to this example. Black circles indicate patients with clinical outcomes, light grey circles indicate patients without clinical outcomes; and dark grey circles indicate normal healthy controls. Surprisingly, non-cirrhotic patients (Ishak F2, 3, 4) with high DSI have greater risk of outcomes.

Figure 14:
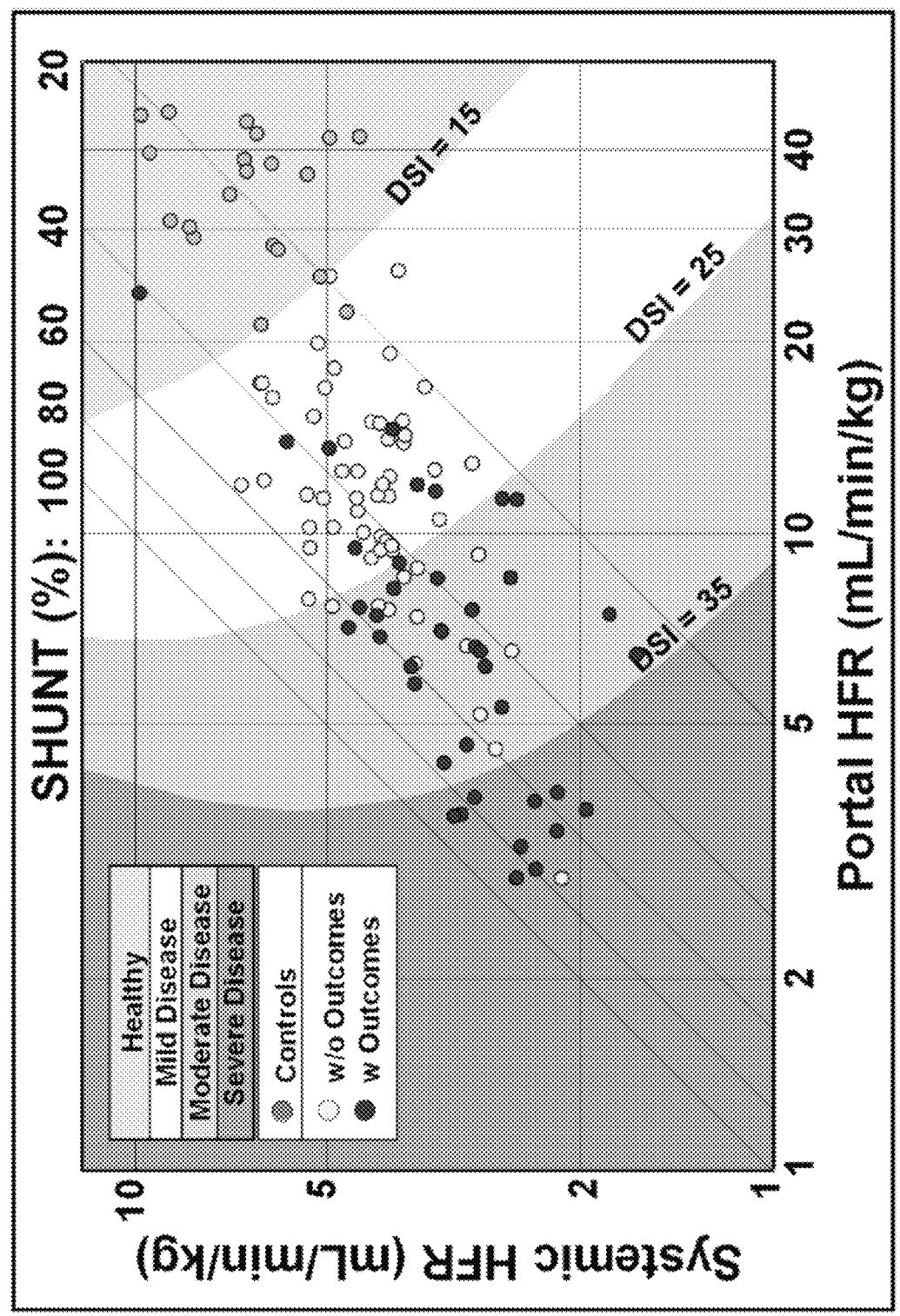
FIG. 14 shows a plot of cholate test results for cirrhotic chronic hepatitis C patients (Ishak F5, 6; n=48,49) with mild disease, moderate disease and severe disease test results of cholate based tests SHUNT (%), systemic HFR (mL/min/kg), portal HFR (mL/min/kg) and DSI. Portal HFR is plotted on the X axis and systemic HFR on the Y axis, SHUNT, the ratio of systemic to portal HFR is represented by the diagonal lines, DSI is displayed in shaded regions. Surprisingly, cirrhotic patients with low DSI have lower risk of outcomes as discussed in Example 10.

FIG. 14 shows a plot for cirrhotic patients (Ishak F5, 6; n=48,49) with mild disease, moderate disease and severe disease test results of cholate based tests SHUNT (%), systemic HFR (mL/min/kg), portal HFR (mL/min/kg) and DSI according to this example. Black circles indicate patients with clinical outcomes, light grey circles indicate patients without clinical outcomes; and dark grey circles indicate normal healthy controls. Surprisingly, cirrhotic patients (Ishak F5,6) with low DSI have a lower risk of clinical outcomes.

Remarkably, cholate tests could outperform biopsy diagnosed cirrhosis in predicting clinical outcomes in hepatitis C patients. The highest prognostic performance was achieved by combining cholate test results into a DSI. This example shows that dual cholate liver function test yielding a DSI could outperform histologic fibrosis stage in identifying patients with medium/large varices and in predicting clinical outcomes in chronic HCV patients.

Example 11

Disease Severity Index Assessment of Disease Severity in Primary Sclerosing Cholangitis (PSC)

Cholate testing was compared to MELD in the assessment of disease severity in a group of compensated or minimally decompensated patients with Primary Sclerosing Cholangitis (PSC).

20 healthy controls served as a reference for comparing the cholate test results in the PSC population. 43 PSC patients were enrolled that had been diagnosed by cholangiography Most were of middle age, male, and had low MELD, CTP, or Mayo PSC Risk Scores. The mean values for bilirubin, INR, albumin, and platelet count reflect the relatively compensated stage of their disease. Alkaline phosphatase was modestly elevated with a broad range. Specifically, the 43 PSC patients were avg. 48.4±12.9 yrs of age, 76% male, with avg. MELD scores of 9.5±4.3, avg. CTP scores of 6.0±1.5, avg. Mayo PSC risk score of 0.85±0.74, avg. bilirubin 1.8±1.8 mg/dL, avg. INR 1.2±0.6, avg. albumin 3.6±0.5, avg. platelet count 190±95×10$^{-3}$ uL-1, and avg. alkaline phosphatase of 206±196 IU/mL.

Patients were subjected to overnight fast and each patient was studied twice within two weeks to check reproducibility. Cholate tested was performed by simultaneous dual administration of 20 mg [24-$^{13}$C]-cholate mixed with HSA intravenously, and 40 mg [2,2,4,4-$^{2}$H]-cholate in juice orally. Blood samples were taken at 0, 5, 20, 45, 60, and 90 min following cholate administration. The serum samples were analyzed by HPLC/MS. Clearances (IV and PO), SHUNT, Disease Severity Index (DSI) were calculated from serum cholates. The cholate oral clearance and the cholate clearance after intravenous administration were calculated from the dose (40 mg for oral administration and 20 mg for intravenous administration) divided by the area under the concentration-time curves for each isotope (milligrams per minute per milliliter) and normalized for the body weight (kilograms), and the cholate shunt was the ratio of clearances for intravenously and orally administered isotopes. The DSI was calculated from the DSI equation developed based on prediction of first clinical outcome in the HALT-C cohort, as shown in Example 10.

$$DSI=5.75 \,(SHUNT)-7.22 \,(Log_e \,Portal \,HFR)-8.45 \,(Log_e \,Systemic \,HFR)+50.$$

Cholate testing demonstrated excellent reproducibility with very low variably from one testing date to another. Reproducibility data are shown in Table 15.

TABLE 15

Reproducibility of Cholate Testing

|  |  | SHUNT | Portal HFR | Systemic HFR |
|---|---|---|---|---|
| Correlation Coefficient | R$^2$ | 0.96 | 0.95 | 0.90 |
| Coefficient of Variation | CV | 10.1% | 10.7% | 9.7% |
| Intraclass Correlation Coefficient | ICC | 0.93 | 0.90 | 0.80 |

The correlation coefficients were excellent at 0.95 and 0.97. The average CV for HFR and SHUNT are 10%, and for STAT was 21%. As STAT is a one-time measurement rather than average of several points, we expected a higher CV. Importantly, there was no significant change in CV across the range of test results indicating excellent reproducibility across wide range of disease severity. The data show that cholate testing is reproducible.

The intra-class correlation measures variability of an individual over the range of all test results. The ICCs range between 0.9 to 0.94, indicating within individual variability is very low. To put this into context, ICC of 0.7-0.8 indicates strong agreement between tests.

DSI Identified PSC Patients with Varices or Decompensation.

Figure 15:
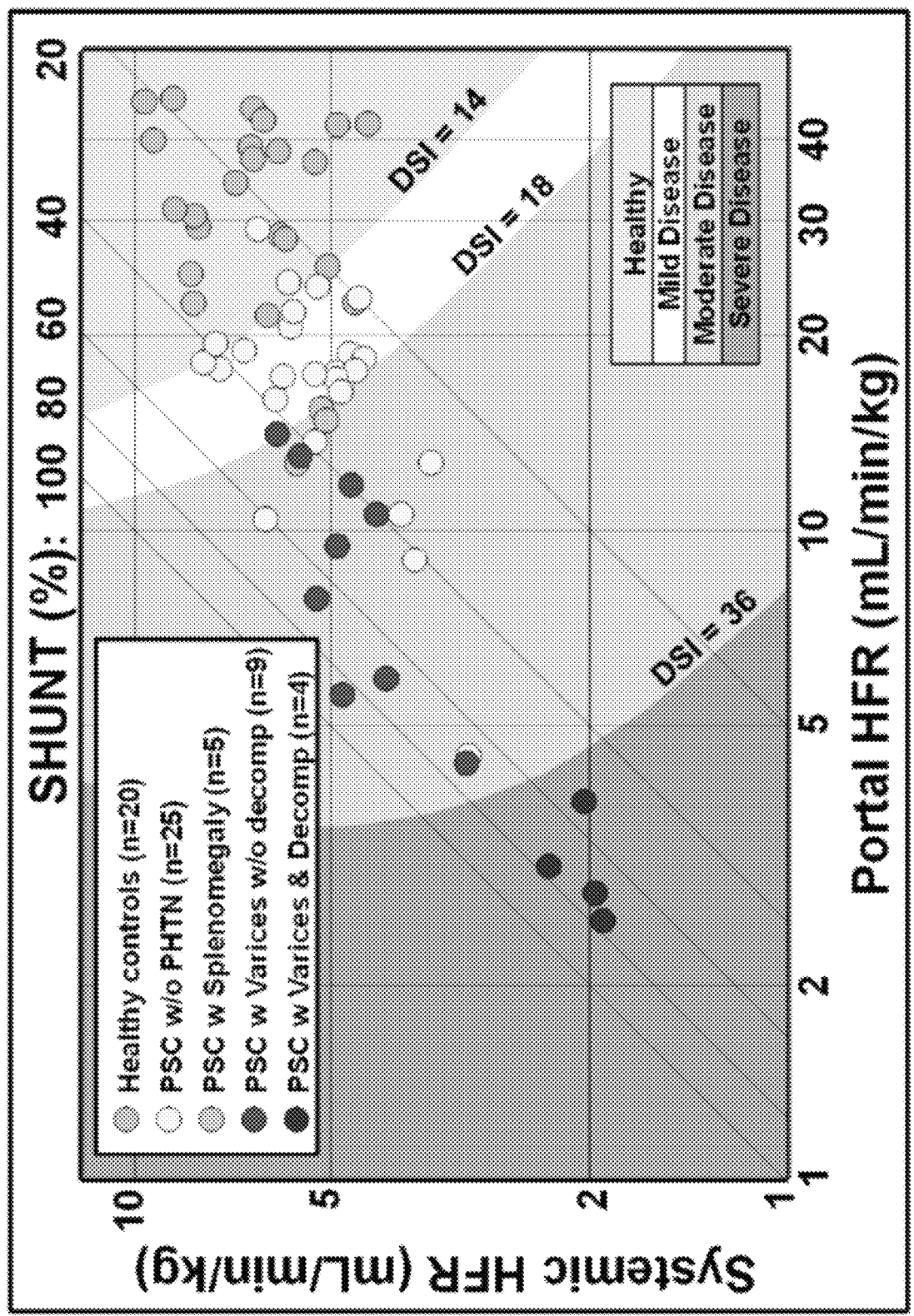
FIG. 15 shows a plot of cholate test results for primary sclerosing cholangitis patients and healthy controls. Portal HFR is plotted on the X axis and systemic HFR on the Y axis, SHUNT, the ratio of systemic to portal HFR is represented by the diagonal lines, DSI is displayed in shaded regions. Predictive DSI cutoffs for PSC disease, varices, and decompensation are shown at the interfaces between zones.

FIG. 15 shows a plot of cholate test results for DSC patients and healthy controls. Portal HFR is plotted on the X axis and systemic HFR on the Y axis. SHUNT, the ratio of systemic to portal HFR is represented by the diagonal lines. DSI is displayed in shaded regions—light grey zone in the upper right with a cutoff of DSI=14 shows DSI of healthy controls, the white zone with a cutoff of DSI=18 shows the DSI of mild disease, the medium grey zone with the cutoff of DSI=36 shows DSI of moderate disease, and the dark grey zone at the lower left shows DSI for the most severe disease. Predictive Cutoffs for PSC disease, varices, and decompensation are shown at the interfaces between zones.

Performance of the cholate cutoffs for defining patients at-risk for varices or decompensation are shown in Table 16.

TABLE 16

Performance of Cholate Cutoffs from PSC Patients.

| PSC Patients with | cutoff | Sens. | Spec. | PPV | NPV | Balanced Accuracy |
|---|---|---|---|---|---|---|
| Varices (n = 13) | DSI ≥ 18 | 100% | 70% | 59% | 100% | 85% |
| Decompensation (n = 4) | DSI ≥ 36 | 100% | 100% | 100% | 100% | 100% |

In healthy controls, DSI was 10±3. In PSC, DSI could identify patients with PHTN (ROC c-statistic 0.80) and varices (ROC c-statistic 0.93). A DSI≥18 was optimal (balanced accuracy 82%) for identifying PHTN and could also identify all patients with varices (100% sensitivity, 70% specificity, 59% PPV, 100% NPV). This cutoff marked the boundary between mild and moderate disease. All patients with DSI≥36, separating moderate and severe disease, either had medium varices or had suffered a variceal hemorrhage, and 75% had ascites. No patients with DSI<36 had ascites or variceal hemorrhage.

Figure 16:
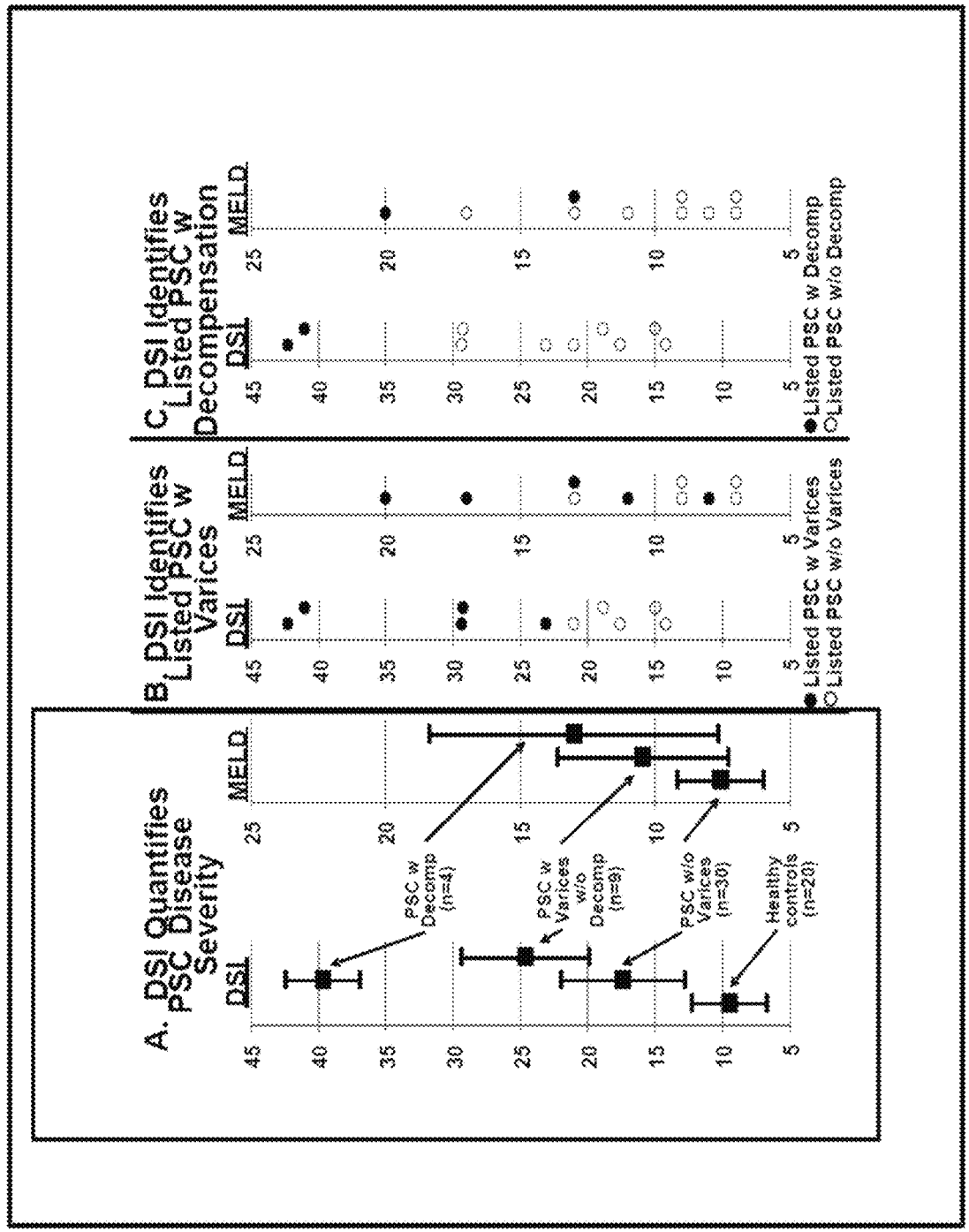
FIG. 16 shows a comparison of DSI values with MELD for PSC patients. Panel A shows a comparison of DSI with MELD for all the PSC patients. The DSI of healthy controls is also shown for reference. Panel B shows a DSI of approximately 20 clearly separates the PSC patients with varices from the PSC patients without varices. Panel C shows a DSI of approximately 35 clearly separates the PSC patients with decompensation from those without decompensation.

DSI quantifies PSC disease severity. As shown in FIG. 16, Panel A shows a comparison of DSI with MELD for all the PSC patients. The DSI of healthy controls is also shown for reference. DSI separates PSC patients from controls, PSC patients without clinical manifestations from healthy controls and PSC patients with varices. DSI identifies the sickest patents, who developed decompensation. In contrast, there was significant overlap in MELD scores between these groups of PSC patients. MELD could not distinguish the groups with any degree of certainty. Surprisingly, cholate testing DSI is superior to MELD in assessing disease severity in patients with primary sclerosing cholangitis.

FIG. 16 Panels B and C show DSI compared to MELD only in the listed patients-patients on the waiting list for liver transplant.

FIG. 16 Panel B shows a DSI of approximately 20 clearly separates the PSC patients with varices from the PSC patients without varices.

FIG. 16 Panel C shows a DSI of approximately 35 clearly separates the PSC patients with decompensation from those without decompensation.

In contrast, FIG. 16 Panels B and C show the overlap in MELD scores between these groups of PSC patients indicate MELD could not distinguish the patients with varices or the patients with decomp with any degree of certainty.

This example shows DSI is superior to MELD in assessing PSC disease severity and identifying patients at risk for varices or decompensation-especially in patients with lower MELD scores. DSI could be used to adjust priority for liver transplantation for PSC patients on the Waiting List.

Figure 17:
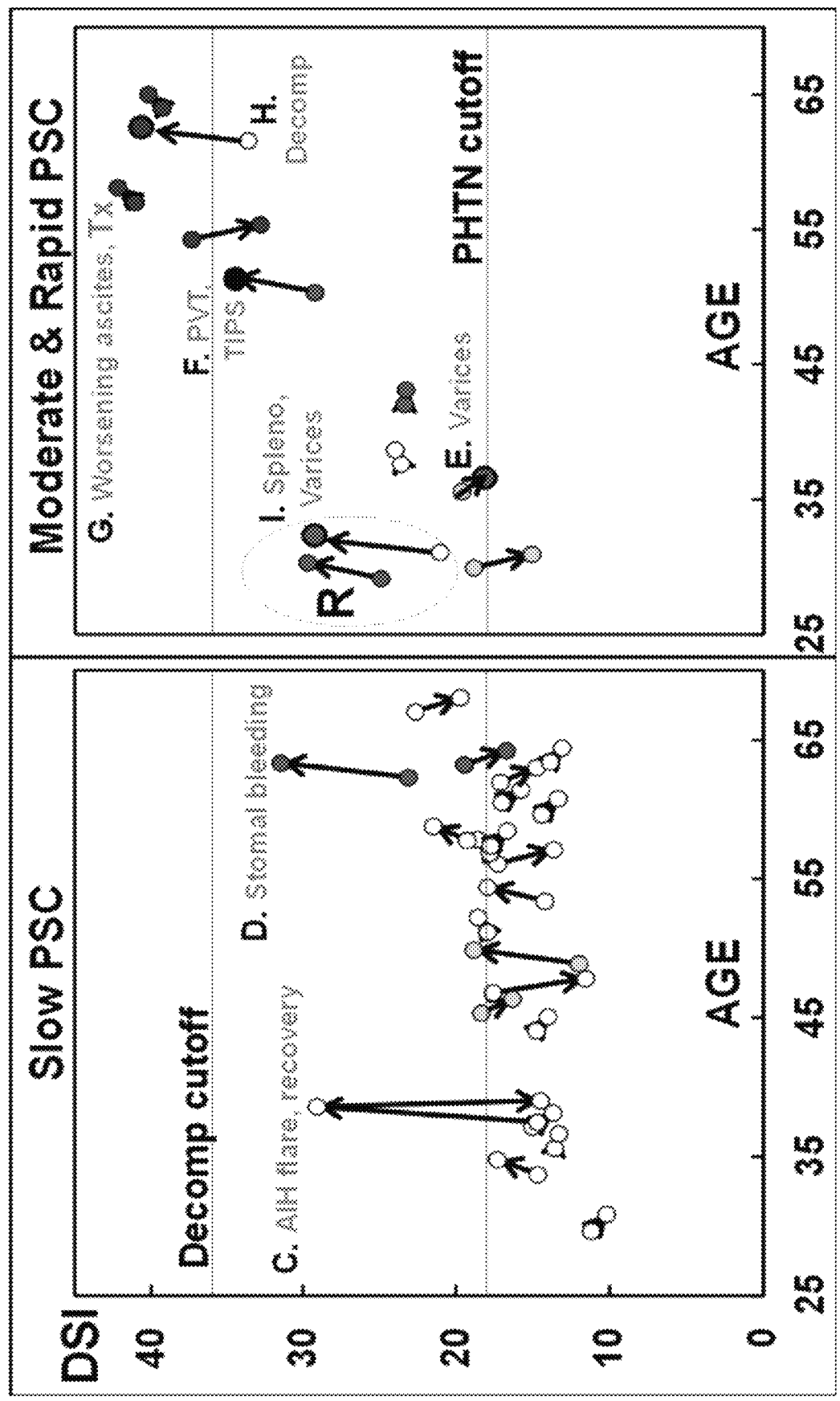
FIG. 17 shows changes in DSI and disease severity in PSC patients that were assessed after a 1 year follow-up. The change in DSI was plotted against the age of the patient. Patients with DSI values indicative of slow PSC progression are shown in the left panel where a cutoff=18 is indicative of PHTN. Patients with DSI values indicative of moderate and rapid PSC progression are shown in the right panel where a cutoff=36 is indicative of decompensation.

FIG. 17 shows changes in DSI and disease severity in PSC patients that were assessed after a 1 year follow-up. The change in DSI was plotted against the age of the patient as shown in FIG. 17. Serial DSI measurements defined category of disease severity. Patients slow PSC progression are shown in the left panel where a cutoff=18 is indicative of PHTN. Patients with moderate and rapid PSC progression are shown in the right panel where a DSI cutoff=35 is indicative of decompensation.

Example 12

Cholate Testing and Disease Severity Index Identification of Primary Sclerosing Cholangitis Waiting List Patients at Risk for Clinical Complications MELD may not be able to assess the risks for clinical complications in listed PSC patients compared to a disease severity index (DSI) based on dual cholate clearances and shunt. Cholate testing was compared to MELD in the assessment of disease severity in a group of patients with Primary Sclerosing Cholangitis (PSC) on the waiting list for liver transplantation.

Patients were tested as provided in Example 11. DSI was calculated as provided in Example 11. Of the 43 PSC patients tested, 10 were on the waiting list for LT. The PSC patients were compared to 20 healthy controls. A comparison of cholate test values, DSI and MELD for patients and healthy controls is shown in Table 17.

TABLE 17

Cholate and DSI values compared to MELD scores in PSC Patients and Healthy Controls.

| | n | SHUNT (%) | Portal HFR (mL/min/kg) | DSI | MELD Score |
|---|---|---|---|---|---|
| Healthy Controls | 20 | 20 ± 1 | 34.7 ± 1.7 | 9.7 ± 0.7 | |
| PSC Patients | 43 | 43 ± 3 $P < 0.001$ | 14.2 ± 1.0 $P < 0.001$ | 21.1 ± 1.2 $P < 0.001$ | 8.7 ± 0.5 |
| PSC not listed for LT | 33 | 40 ± 3 | 15.4 ± 1.1 | 19.8 ± 1.3 | 7.8 ± 0.3 |
| Listed PSC | 10 | 56 ± 7 $P < 0.01$ | 10.2 ± 1.8 $P < 0.05$ | 25.5 ± 3.1 $P < 0.05$ | 11.4 ± 1.4 $P < 0.001$ |
| Listed PSC w/o varices | 5 | 41 ± 6 | 15.0 ± 1.3 | 18.0 ± 1.1 | 9.0 ± 1.1 |
| Listed PSC w varices | 5 | 71 ± 8 | 5.4 ± 1.4 | 33.0 ± 3.7 | 13.8 ± 2.1 |
| | | $P < 0.005$ | $P < 0.05$ | $P < 0.005$ | ns |

Table 17 shows SHUNT, Portal HFR and DSI couls differentiate PSC patients from healthy controls, listed PSC patients from PSC patients not listed for liver transplant (LT), listed PSC patients with varices from those without varices. MELD could not differentiate those with varices.

Figure 18:
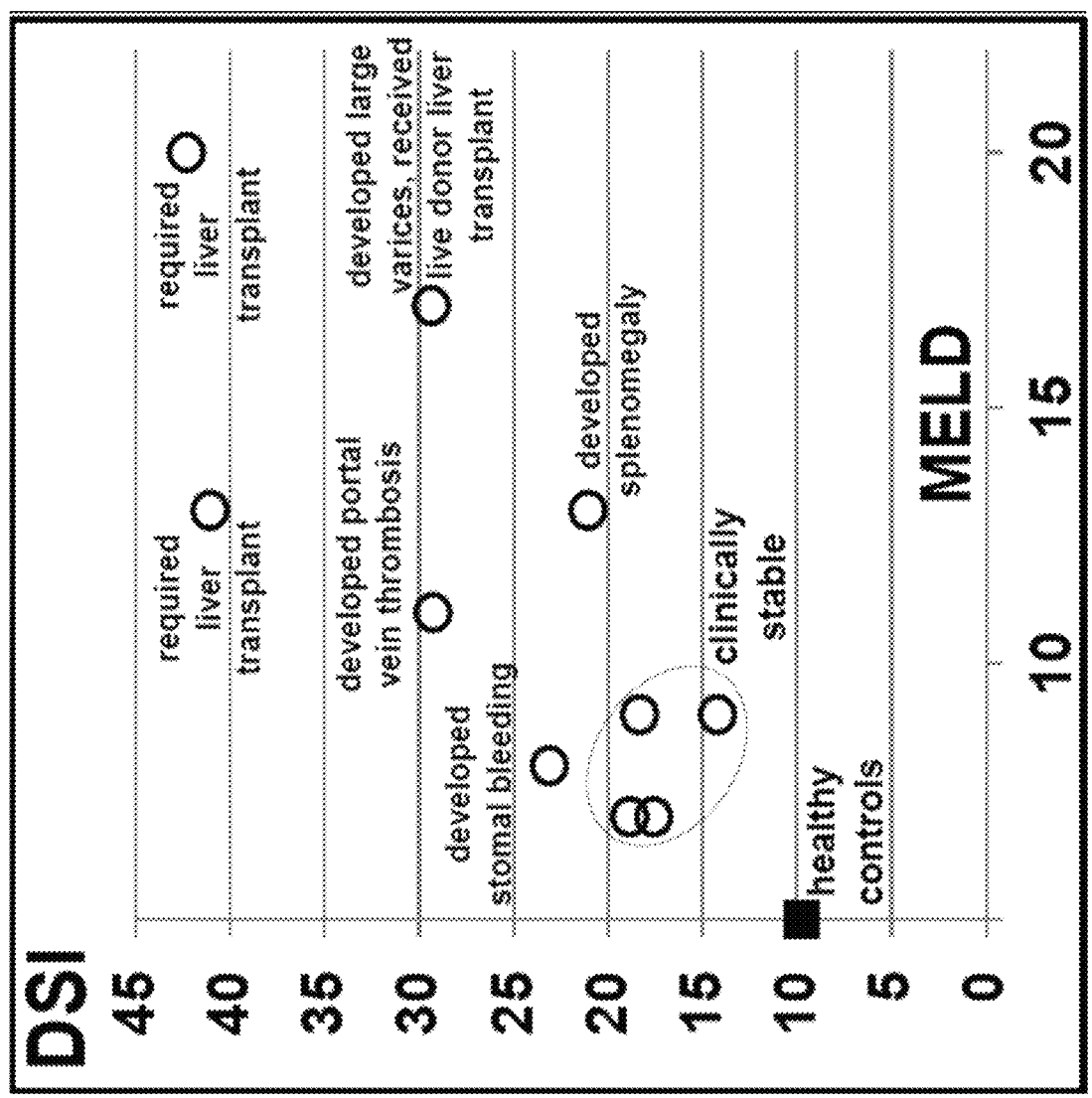
FIG. 18 shows a plot of DSI versus MELD scores in PSC patients on the waiting list for liver transplantation. DSI was superior to MELD in assessing risk for complications and priority for liver transplant in PSC patients. Despite low MELD scores, PSC patients with DSI>20 developed portal hypertension-related complications, and PSC patients with DSI>40 required liver transplantation.

FIG. 18 shows a plot of DSI versus MELD scores in PSC patients on the waiting list for liver transplantation. DSI was superior to MELD in assessing risk for complications and priority for liver transplant in PSC patients. Despite low MELD scores, PSC patients with DSI>20 developed portal hypertension-related complications, and PSC patients with DSI>40 required liver transplantation.

Example 13

Cholate Testing and Disease Severity Index Measurement of Functional Improvement After Sustained Virological Response in Chronic Hepatitis C Patients Chronic HCV patients with advanced fibrosis or cirrhosis are difficult to treat and cure. The aims of this study were to determine if liver function measured with Cholate Testing could predict sustained virological response (SVR) to peginterferon/ribavirin (PEG/RBV) and to measure the improvement in hepatic function in those achieving SVR.

230 chronic HCV patients (Ishak F2-6) enrolled in the HALT-C Trial, characterized by advanced fibrosis and failure of prior treatment with interferon-based treatment, were tested at baseline and then retreated with PEG/RBV. Patients achieving sustained virological response SVR (n=32, including 5 cirrhotics) and non-responders (NR) were retested at 2 yrs.

At baseline and after 2 years, patients were subjected to cholate testing by simultaneous dual administration of 20 mg [24-$^{13}$C]-cholate mixed with HSA intravenously, and 40 mg [2,2,4,4-$^2$H]-cholate in juice orally. Blood samples were taken at 0, 5, 20, 45, 60, and 90 min following cholate administration. The serum samples were analyzed by HPLC/MS, and clearances (IV and PO), SHUNT, Disease Severity Index (DSI) were calculated from serum cholates. The DSI was calculated from the DSI equation developed based on prediction of first clinical outcome in the HALT-C cohort, as shown in Example 10.

Figure 19:
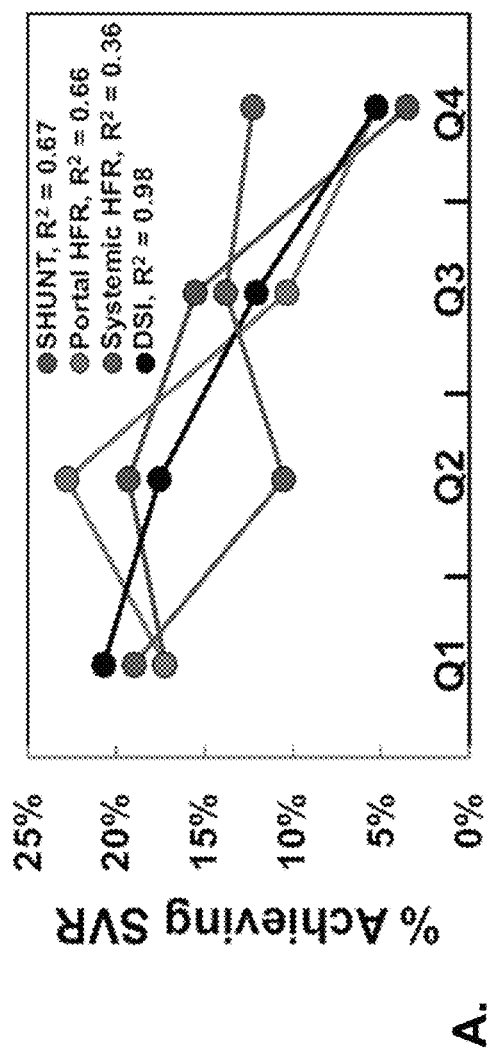
FIG. 19 panel A shows a graph of patients achieving SVR compared to quartiles for hepatic function. The probability of SVR correlated best with DSI.
Figure 19:
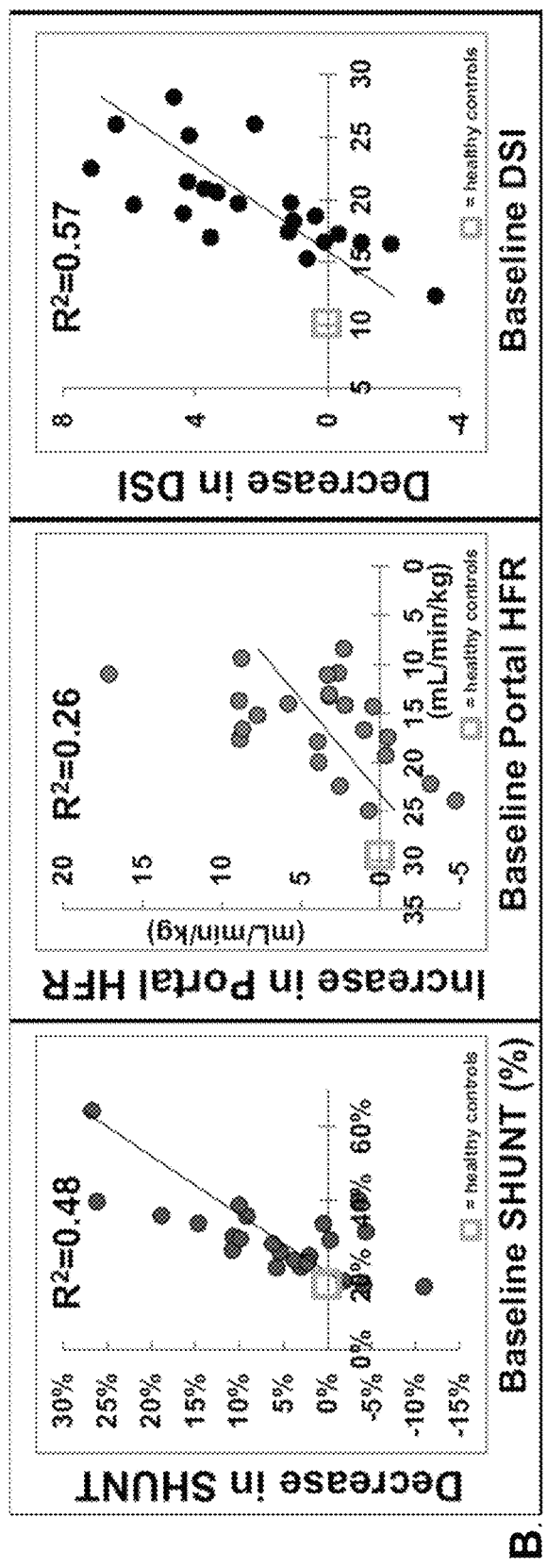

FIG. 19 panel A shows a graph of patients achieving SVR compared to quartiles for hepatic function. The probability of SVR correlated best with DSI.

As shown in Table 18, hepatic functional declined in non-responders (NR, n=80), and improved with SVR (n=23).

TABLE 18

Hepatic Function Change from Baseline in HCV Patients with and without SVR following Retreatment.

| Change (mean ± SEM) | NR | SVR | P |
|---|---|---|---|
| SHUNT (%) | 5.5 ± 1.9 | −6.1 ± 1.9 | $P < 0.01$ |
| Portal HFR (mL/min/kg) | −1.3 ± 0.6 | 4.1 ± 1.0 | $P < 0.0001$ |
| Systemic HFR (mL/min.kg) | −0.1 ± 0.1 | 0.0 ± 0.2 | ns |
| DSI | 1.8 ± 0.6 | −2.4 ± 0.6 | $P < 0.001$ |

FIG. 19, panel B shows hepatic functional improvement after SVR following retreatment of chronic HCV patients with PEG/RBV (peginterferon/ribavirin). More severe baseline impairment resulted in greater functional improvement after SVR when tested two years after baseline.

Non-invasive cholate liver function testing predicts the probability of achieving SVR when patients are retreated with PEG/RBV and quantifies significant improvements in function after SVR. The improvements in hepatic function after SVR are greater in those patients who had more severe baseline impairment.

Example 14

Development of a Disease Severity Index Equation

The aim of this study was to compare dual cholate liver function testing to histologic stage of fibrosis in identifying those chronic HCV patients who have medium/large varices and those who are at risk for future clinical outcomes.

Chronic HCV patients (n=220) enrolled in the HALTC trial had dual cholate testing, liver biopsy, endoscopic screening for varices, and were followed for 4.9±2.2 years for clinical outcomes. The patients had Ishak fibrosis scores of F2-6, CTP scores of 5 or 6, and no prior history of clinical complications. Medium or large esophageal varices were found in 22 patients. Clinical outcomes, defined as a 2 point CTP progression, variceal bleeding, ascites, hepatic encephalopathy, or liver related death, occurred in 52 patients.

Dual cholate testing was performed. Briefly, orally administered Cholate-2,2,4,4-d4 (40 mg) is taken up into the portal vein by specific ileal bile salt transporters. Intravenously administered Cholate-24-13C (20 mg) enters the liver primarily through the hepatic artery. Specific hepatic bile salt transporters clear the dual cholates from the portal and systemic circulation. Peripheral blood samples were taken from the patients at 0, 5, 20, 45, 60, and 90 minutes after simultaneous dosing and were assayed by an LCMS method validated to FDA guidelines for accuracy and precision. SHUNT, portal HFR and systemic HFR were calculated.

The AUC c-statistics and optimum cutoffs were determined from ROC curves, and test performance was evaluated by the balanced accuracy and Youden index (J). Performance of individual tests is shown in Table 19. Individual tests predict outcomes.

TABLE 19

Performance of Individualized Cholate Tests

|  | AUC C-statistic | Optimum cutoff | Sens. | Spec. | PPV | NPV | Balanced Accuracy | Youden Index (J) |
| --- | --- | --- | --- | --- | --- | --- | --- | --- |
| Portal HFR | 0.83 | 8.5 mL/min/kg | 65% | 88% | 62% | 89% | 76% | 0.53 |
| SHUNT | 0.75 | 46% | 58% | 82% | 50% | 86% | 70% | 0.40 |
| Systemic HFR | 0.73 | 3.6 mL/min/kg | 60% | 80% | 48% | 86% | 70% | 0.39 |

Each test and its Log transform was also evaluated by Hazard Regression as shown in Table 20.

TABLE 20

Univariate Cox Proportional Hazard Regression Analysis (Chi-square).

| Portal HFR | 51 | $\text{Log}_e$ Portal HFR | 70 |
| SHUNT | 45 | $\text{Log}_e$ SHUNT | 35 |
| Systemic HFR | 22 | $\text{Log}_e$ Systemic HFR | 30 |

The tests with the highest Chi-square were combined into a disease severity index to improve performance.

The test with highest Chi-square, $\text{Log}_e$ Portal HFR, was graphed against the second best, SHUNT, on a new feature space. The optimum linear classifier was:

$$Y_{(SHUNT)} = 1.24\, X_{(\text{Log}_e\, Portal\, HFR)} - 2.36$$

which defined the component weighting and the $DSI_2$.

$$DSI_2 = 1.24\, \text{Log}_e\, \text{Portal HFR} - \text{SHUNT}$$

TABLE 21

DSI2 Statistics.

|  | AUC C-statistic | Optimum cutoff | Sens. | Spec. | PPV | NPV | Balanced Accuracy | Youden Index (J) |
| --- | --- | --- | --- | --- | --- | --- | --- | --- |
| DSI2 | 0.82 | 2.36 | 73% | 83% | 57% | 91% | 78% | 0.56 |

$DSI_2$ had improved performance over the individual tests.

The $DSI_2$ was graphed against the $\text{Log}_e$ Systemic HFR on a new feature space. The optimum linear classifier was:

$$Y_{(\text{Log}_e\, Systemic\, HFR)} = -0.623\, X_{(DSI2)} + 3.03$$

defining the weighting of the $3^{rd}$ component and the $DSI_3$.

$$DSI_3 = \text{Log}_e\, \text{Systemic HFR} + 0.623\, DSI_2$$

TABLE 22

DSI3 Statistics.

|  | AUC C-statistic | Optimum cutoff | Sens. | Spec. | PPV | NPV | Balanced Accuracy | Youden Index (J) |
| --- | --- | --- | --- | --- | --- | --- | --- | --- |
| DSI3 | 0.83 | 3.03 | 87% | 72% | 49% | 95% | 79% | 0.59 |

$DSI_3$ had improved performance over $DSI_2$.

The $DSI_3$ was rearranged and constants added to have the best liver function anticipated as DSI=0, and the worst liver function as DSI=50.

$$DSI = 5.34\, \text{SHUNT} - 6.65\, \text{Log}_e\, \text{Portal HFR} - 8.57\, \text{Log}_e\, \text{Systemic HFR} + 44.66$$

The DSI equation identifies patients with medium/large varices. Specifically, using the DSI equation, a DSI>19 indicates high risk of medium to large varices; DSI10-19 is indicative of low risk of medium/large varices; and DSI of 0-10 is indicative of healthy liver function The DSI equation predicts future clinical outcomes in patients. Specifically, using the DSI equation, a DSI>19 indicates high risk of clinical outcomes; DSI10-19 is indicative of low risk of clinical outcomes; and DSI of 0-10 is indicative of healthy liver function.

A comparison of DSI to fibrosis stage on biopsy is shown in Tables 23 and 24.

TABLE 23

Identifying Patients with Medium/Large Varices.

| | AUC C-statistic | Optimum cutoff | Sens. | Spec. | PPV | NPV | Balanced Accuracy | Youden Index (J) |
|---|---|---|---|---|---|---|---|---|
| Biopsy Fibrosis stage | 0.79 | Cirrhosis (Ishak F5-F6) | 77% | 61% | 18% | 96% | 69% | 0.38 |
| Dual Cholate DSI | 0.82 | DSI > 19 | 86% | 65% | 21% | 98% | 76% | 0.51 |
| Improvement over Biopsy | 3% | | 12% | 6% | 18% | 2% | 9% | 33% |

TABLE 24

Identifying Future Clinical Outcomes.

| | AUC C-statistic | Optimum cutoff | Sens. | Spec. | PPV | NPV | Balanced Accuracy | Youden Index (J) |
|---|---|---|---|---|---|---|---|---|
| Biopsy Fibrosis stage | 0.75 | Cirrhosis (Ishak F5-F6) | 71% | 66% | 39% | 88% | 69% | 0.37 |
| Dual Cholate DSI | 0.83 | DSI > 19 | 87% | 72% | 49% | 95% | 79% | 0.59 |
| Improvement over Biopsy | 11% | | 22% | 9% | 24% | 7% | 16% | 57% |

As shown in Tables 23 and 24, DSI is better than histologic fibrosis stage at biopsy in all measures of performance for identifying future clinical outcomes.

We claim:

1. A method of predicting a response to a treatment of a chronic liver disease in a patient, comprising
   determining a baseline Disease Severity Index (DSI) value in the patient having a chronic liver disease prior to the treatment; and
   comparing the baseline DSI value in the patient to a DSI cutoff value, wherein a baseline DSI value in the patient below the DSI cutoff value indicates a higher predicted response rate to the treatment in the patient compared to a subject exhibiting a DSI value above the DSI cutoff value,
   wherein the determining of the baseline DSI value in the patient comprises
   performing a cholate liver function tests in the patient to obtain a portal hepatic filtration rate (portal HFR) value, a systemic hepatic filtration rate (systemic HFR) value, and optionally a cholate SHUNT test value; and
   deriving the disease severity index (DSI) values from the cholate test results,
   wherein the portal HFR test value in the patient is determined by a method comprising:
   (a) receiving a plurality of blood or serum samples collected from the patient having a chronic liver disease, following oral administration of a dose of a first distinguishable cholate compound (dose$_{oral}$) to the patient, wherein the samples have been collected from the patient over intervals of from two to seven time points spanning a period of time of no more than about 90 minutes after administration;
   (b) measuring concentration of the first distinguishable cholate compound in each sample comprising HPLC-MS;
   (c) generating an individualized oral clearance curve from the concentration of the first distinguishable cholate in each sample comprising using a computer algorithm curve fitting to a model distinguishable cholate clearance curve;
   (d) computing the area under the individualized oral clearance curve (AUC) (mg/mL/min) and dividing the dose (in mg) by AUC of the orally administered first distinguishable cholate compound to obtain the oral cholate compound clearance in the patient; and
   (e) dividing the oral cholate compound clearance by the weight of the patient in kg to obtain the portal HFR value in the patient (mL/min/kg); or,
   wherein the portal HFR value in the patient is estimated from a cholate STAT test value in the patient.

2. The method of claim 1, wherein the cutoff value was derived from DSI values in one or more normal healthy subjects, group of known subjects, or within the patient over time.

3. The method of claim 2, wherein the group of known subjects is selected from a group of healthy subjects, a group of subjects with chronic liver disease having a fibrosis stage; portal hypertension; Childs-Turcotte-Pugh (CTP) score A; CTP score B; CTP score C; Model for End-stage Liver Disease (MELD) score; primary sclerosing cholangitis (PSC) not listed for transplant; PSC listed for liver transplant; PSC listed for liver transplant without varices; PSC listed for liver transplant with varices; ascites; stomal bleeding; splenomegaly; varices; variceal hemorrhage; hepatic encephalopathy; decompensation; or liver related death.

4. The method of claim 3, wherein the fibrosis stage is determined by a method selected from the group consisting of liver biopsy; elastography; fibrosis serum biomarker; circulating proteins or fragments thereof; and nonalcoholic fatty liver disease (NAFLD) fibrosis score.

5. The method of claim 4, wherein the liver biopsy determines Ishak fibrosis score (liver biopsy) of F2 (mild portal fibrosis), F3, F4 (moderate bridging fibrosis), F5 (nodular formation and incomplete cirrhosis), or F6 (cirrhosis).

6. The method of claim 3, wherein the DSI cutoff value is selected from the group consisting of 14, 15, 18, 19, 20, 23, 25, 30, 35, 36, and 40.

7. The method of claim 1, wherein the chronic liver disease is selected from the group consisting of chronic hepatitis C (CHC), chronic hepatitis B, alcoholic liver disease, Alcoholic SteatoHepatitis (ASH), Non-Alcoholic Fatty Liver Disease (NAFLD), steatosis, Non-Alcoholic SteatoHepatitis (NASH), autoimmune liver disease, cryptogenic cirrhosis, hemochromatosis, Wilson's disease, alpha-1-antitrypsin deficiency, liver cancer, liver failure, cirrhosis, primary sclerosing cholangitis (PSC), and other cholestatic liver diseases.

8. The method of claim 7, wherein the chronic liver disease is selected from the group consisting of CHC, PSC, and NASH.

9. The method of claim 1, wherein the treatment is selected from the group consisting of antiviral treatment, antifibrotic treatment, antibiotics, immunosuppressive treatments, anti-cancer treatments, ursodeoxycholic acid, insulin sensitizing agents, interventional treatment, liver transplant, lifestyle changes, dietary restrictions, low glycemic index diet, antioxidants, vitamin supplements, transjugular intrahepatic portosystemic shunt (TIPS), catheter-directed thrombolysis, balloon dilation and stent placement, balloon-dilation and drainage, weight loss, exercise, and avoidance of alcohol.

10. The method of claim 1, wherein the portal HFR value, systemic HFR value, and/or SHUNT value are obtained on the same test day.

11. The method of claim 1, wherein the systemic HFR value in the patient is determined by a method comprising
(a) receiving a plurality of blood or serum samples collected from a patient having or at risk of a chronic liver disease, following intravenous administration of a dose of a second distinguishable cholate compound ($dose_{iv}$) to the patient, wherein the samples have been collected from the patient over intervals of from two to seven time points spanning a period of time of no more than about 90 minutes after administration;
(b) measuring concentration of the second distinguishable cholate compound in each sample comprising HPLC-MS;
(c) generating an individualized intravenous clearance curve from the concentration of the second distinguishable cholate compound in each sample comprising using a computer algorithm curve fitting to a model second distinguishable cholate clearance curve;
(d) computing the area under the individualized intravenous clearance curve (AUC) (mg/mL/min) and dividing the dose (in mg) by AUC of the intravenously administered second distinguishable cholate compound to obtain the intravenous cholate compound clearance in the patient; and
(e) dividing the intravenous cholate clearance by the weight of the patient in kg to obtain the systemic HFR value in the patient (mL/min/kg).

12. The method of claim 1, wherein the deriving of the baseline DSI value comprises
employing a disease severity index equation (DSI equation) to obtain a DSI value or mathematically transformed DSI value in the patient, wherein the DSI equation comprises one or more portal HFR or mathematically transformed portal HFR terms, one or more systemic HFR or mathematically derived systemic HFR terms, and a constant to obtain the baseline DSI value.

13. The method of claim 12, wherein the disease severity index (DSI) equation comprises $$DSI = A(\text{SHUNT}) + B(\log_e \text{portal } HFR) + C(\log_e \text{systemic } HFR) + D$$

wherein
SHUNT is SHUNT test value in the patient (%);
portal HFR is portal hepatic flow rate (HFR) test value in the patient as mL/min/kg, wherein kg is body weight of the patient;
systemic HFR is systemic HFR value in the patient as mL/min/kg, wherein kg is body weight of the patient;
A is a SHUNT coefficient;
B is a Portal HFR coefficient;
C is a Systemic HFR coefficient; and
D is the constant.

14. The method of claim 13, wherein the SHUNT coefficient A is a number from 0 to positive 25; the Portal HFR coefficient B is a number from 0 to negative 25; and the Systemic HFR coefficient C is a number from 0 to negative 25, and wherein at least one of A, B, and C is not 0.

15. The method of claim 13, wherein the constant D is a positive number between 5 and 125.

16. The method of claim 13, wherein the SHUNT test value in the patient is determined by a method comprising
(a) receiving a plurality of blood or serum samples collected at two to seven time points over no more than about 90 min from the patient having a chronic liver disease, following oral administration of a dose of a first distinguishable cholate compound ($dose_{oral}$) to the patient and simultaneous intravenous co-administration of a dose of a second distinguishable cholate compound ($dose_{iv}$) to the patient, wherein the samples have been collected over intervals spanning a period of time after administration;
(b) quantifying the concentration of the first and the second distinguishable cholate compounds in each sample comprising HPLC-MS;
(c) generating an individualized oral clearance curve from the concentration of the first distinguishable cholate compound in each sample comprising using a computer algorithm curve fitting to a model oral distinguishable cholate clearance curve and computing the area under the individualized oral clearance curve (AUCoral);
(d) generating an individualized intravenous clearance curve from the concentration of the second distinguishable cholate compound in each sample by use of a computer algorithm curve fitting to a model intravenous second distinguishable cholate clearance curve and computing the area under the individualized intravenous clearance curve (AUCiv); and
(e) calculating the shunt value in the patient using the formula:

$$AUC_{oral}/AUC_{iv} \times Dose_{iv}/Dose_{oral} \times 100\%.$$

17. The method of claim 16, wherein the first distinguishable cholate compound is a first stable isotope labeled cholate and the second distinguishable cholate compound is a second stable isotope labeled cholate.

18. The method of claim 17, wherein the first and second stable isotope labeled cholates are selected from 2,2,4,4-d4 cholate and 24-$^{13}$C-cholate.

19. The method of claim 16, wherein the samples have been collected from the patient at time points comprising about 0, about 5, about 20, about 45, about 60, and about 90 minutes after the administration.

20. The method of claim 1, further comprising performing an additional test or procedure selected from the group consisting of liver ultrasound monitoring; elastography; liver biopsy; histological assessment; biomarker or biomarker panel; metabolic test; Model for End Stage Liver Disease (MELD) score; and Childs-Turcotte-Pugh (CTP) score.

21. The method of claim 20, wherein the biomarker or biomarker panel is a clinical biochemistry laboratory assay selected from the group consisting of serum albumin; alanine transaminase; aspartate transaminase; alkaline phosphatase; total bilirubin; direct bilirubin; creatinine; gamma glutamyl transpeptidase; complete blood count (CBC); platelet count; hematocrit; 5' Nucleotidase; and prothrombin time-international normalized ratio (PT-INR).

22. The method of claim 20, wherein the biomarker or biomarker panel is a fibrosis test selected from the group consisting of fibrosis serum biomarker; circulating proteins or fragments thereof; Ishak fibrosis score; fibrotest biochemical markers score; and nonalcoholic fatty liver disease (NAFLD) fibrosis score.

23. The method of claim 20, wherein the biomarker or biomarker panel comprises a pattern of pro-inflammatory cytokines.

24. The method of claim 23, wherein the pro-inflammatory cytokines are selected from the group consisting of IFN-γ, TNF-α, GM-CSF, IL-1β, IL-6, and IL-8.

25. The method of claim 1, wherein the STAT test value in the patient is obtained by a method comprising
(a) receiving a single blood or serum sample collected from the patient, following oral administration of a dose of a distinguishable cholate compound (dose$_{oral}$), wherein the sample has been collected from the patient at a specific time point within 20-180 minutes after administration; and
(b) measuring concentration of the distinguishable cholate compound (uM) in the sample.

26. The method of claim 25, further comprising
(c) transforming the distinguishable cholate compound concentration (uM) into an estimated portal flow (mL/min/kg) comprising $y=0.9702x+0.0206$, wherein x is the LOG Portal HFR (FLOW);
y is LOG STAT; and
kg is body weight of patient.

* * * * *